United States Patent
Schwartz et al.

(10) Patent No.: US 6,248,765 B1
(45) Date of Patent: Jun. 19, 2001

(54) IMIDAZOLE DERIVATIVES AS HISTAMINE RECEPTOR H3 (ANT) AGONISTS

(75) Inventors: Jean-Charles Schwartz, Paris; Jean-Michel Arrang, Gif sur Yvette; Monique Garbarg, Paris; Agnes Quemener, Paris; Jeanne-Marie Lecomte, Paris; Xavier Ligneau, Paris, all of (FR); Walter G. Schunack, Berlin (DE); Holger Stark, Berlin (DE); Katja Purand, Berlin (DE); Annette Huls, Berlin (DE); Reidemeister Sybille, Berlin (DE); Athmani Salah, Glasgow; Charon Robbin Ganellin, Hertfordshire, both of (GB); Nadia Pelloux-Leon, Meylan (FR); Wasyl Tertiux, Hertfordshire (GB); Michael C. O. Krause; Sadek Bassem, both of Berlin (DE)

(73) Assignees: Institut National de la Sante et de la Recherche Medical; Societe Civile Bioprojet, both of (FR)

( * ) Notice: Subject to any disclaimer, the term of this patent is extended or adjusted under 35 U.S.C. 154(b) by 40 days.

(21) Appl. No.: 08/750,163

(22) PCT Filed: Mar. 21, 1996

(86) PCT No.: PCT/FR96/00432

§ 371 Date: Jan. 1, 1997

§ 102(e) Date: Jan. 1, 1997

(87) PCT Pub. No.: WO96/29315

PCT Pub. Date: Sep. 26, 1996

(30) Foreign Application Priority Data

Mar. 21, 1995 (FR) .................................................. 95 03267

(51) Int. Cl.$^7$ ....................... A61K 21/425; C07D 207/30; C07D 207/323

(52) U.S. Cl. ........................ 514/365; 548/560; 548/561; 548/562; 548/563; 548/564

(58) Field of Search ............................ 514/365; 548/560, 548/564, 561, 562, 563

(56) References Cited

FOREIGN PATENT DOCUMENTS

2686084 * 7/1993 (FR) .

OTHER PUBLICATIONS

Chemical Abstracts 123:160553, Schlicker, 1995.*
Chemical Abstracts 121:272809, Ligneau, 1994.*

* cited by examiner

Primary Examiner—D. Margaret Seaman
(74) Attorney, Agent, or Firm—Bierman, Muserlian and Lucas

(57) ABSTRACT

Novel imidazole derivatives as histamine receptor $H_3$ antagonists and/or agonists, preparation thereof and therapeutical uses thereof. Chemical compounds for use as histamine receptor $H_3$ agonists, partial agonists or antagonists, having general formula (Ia) or (Ib), the use thereof for making drugs, and methods for revealing the agonist, partial agonist or antagonist activity of such compounds in vivo, are disclosed.

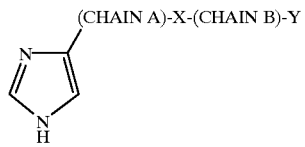

(Ia)

93 Claims, No Drawings

IMIDAZOLE DERIVATIVES AS HISTAMINE RECEPTOR H3 (ANT) AGONISTS

This application is a 371 of PCT/FR96/00432, filed Mar. 21, 1996.

The present invention relates to new imidazole derivatives, to their preparation and also to their therapeutic applications as chemical compounds which are histamine $H_3$ receptor antagonists, agonists or partial agonists.

Histamine, in a known manner, an aminated base derived from histidine by decarboxylation, causes smooth muscle contraction, a secondary hypotension and phenomena resembling anaphylactic shock (oedema, urticaria, etc.) in man and in animals.

Histamine is also a chemical mediator released by some histaminergic cells.

Hence the interest which exists, in particular in the medical field, in being able to control histamine release, in particular in the case of disease, is readily understood.

This effect may be obtained by stimulation of the $H_3$ receptors (presynaptic autoreceptors), whereas blockade of the latter induces, on the contrary, an increase in histamine release, in particular at the cerebral histaminic neurons (Nature, 1983, 302:832). Moreover, it has become apparent more recently that the $H_3$ receptors also have a role as presynaptic heteroreceptors and, as such, they control, for example, the release of pro-inflammatory peptides in some tissues; their stimulation by $H_3$ agonists will enable anti-inflammatory, anti-asthmatic and antimigraine effects to be produced and will make it possible to combat glaucoma, sleep-associated problems, Alzheimer's disease, schizophrenia, depression, hypertension, dysfunctions of a sexual nature, and the like.

The $H_3$ receptors have been defined pharmacologically by evaluating the effect of stimulating them on the release of endogenous histamine from slices of rat brain (Nature 1987, 327: 117–123). In addition, other models of studies of the effectors of the $H_3$ receptor have been proposed since then (Physiol. Rev. 1991, 71: 1–51), but not all these models readily enable the effect of partial agonists of low intrinsic activity to be demonstrated, it being possible for the latter to be readily taken for antagonists. In point of fact, these partial agonists may be employed as medicinal products for indications similar to those of pure agonists, and not for indications for which antagonists are reserved. It is hence extremely important for the applications to make this distinction in a preclinical phase.

Moreover, Patent Application WO 93/14070 describes imidazole compounds displaying histamine $H_3$ receptor-antagonist properties, controlling the release and synthesis of histamine.

It is the purpose of the present invention to select, from the family of imidazole compounds described in the said Patent Application WO 93/14070, groups of compounds or compounds which are noteworthy for their high activity with respect to histamine $H_3$ receptors while being generally especially well suited as a result of their pharmacological properties to the preparation of medicinal products.

Moreover, the inventors of the present invention have developed a sensitive biological test enabling an agonist displaying low intrinsic activity to be clearly differentiated from a pure antagonist. They have, as a result, identified partial agonists having strong biological activity in vivo from among compounds which, on the basis of their chemical structure and their traditional test, were predicted to be antagonists. They have also synthesized imidazole derivatives having a stronger $H_3$ antagonist activity, in particular in vivo, than that of the compounds known hitherto, and this is likely to decrease the toxic effects or even the side-effects at the therapeutic doses, and accordingly to facilitate their clinical use.

Hence the present invention relates to chemical compounds which are histamine $H_3$ receptor agonists, partial agonists or antagonists, corresponding to the general formula:

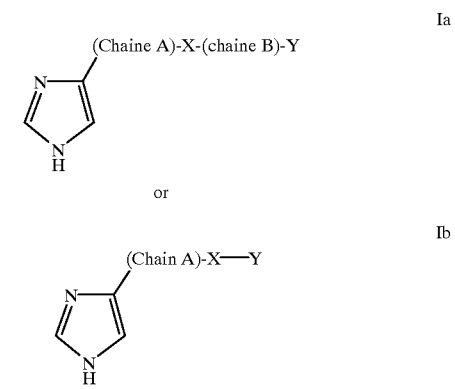

in which:
the chain A represents an unbranched, branched or unsaturated alkyl group —$(CH_2)_n$— where n is an integer which can vary between 1 and 8 and preferably between 1 and 4; an unbranched or branched alkene group comprising from 1 to 8 carbon atoms and preferably 1 to 4 carbon atoms; an unbranched or branched alkyne group comprising from 1 to 4 carbon atoms;

the group X represents —OCONH—; —OCON(alkyl)-; —OCON(alkene)-; —OCO—; —OCSNH—; —$CH_2$—; —O—; —$OCH_2CO$—; —S—; —CO—; —CS—; amine; alkene;

the chain B represents an unbranched, branched or unsaturated lower alkyl comprising from 1 to 8 carbon atoms and preferably 1 to 5 carbon atoms; —$(CH_2)_n$(hetero atom)— where the hetero atom is preferably a sulphur or oxygen atom; n being an integer which can vary between 0 and 5, preferably between 0 and 4;

the group Y represents a phenyl group, unsubstituted or mono- or polysubstituted with one or more identical or different substituents selbcted from halogen atoms, $OCF_3$, CHO, $CF_3$, $SO_2N(alkyl)_2$, $SO_2N(CH_3)_2$, $NO_2$, S(alkyl), S(aryl), $SCH_2$(phenyl), an unbranched or branched alkene, an unbranched or branched alkyne optionally substituted with a trialkylsilyl radical, —O(alkyl), —O(aryl), —$CH_2CN$, a ketone, an aldehyde, a sulphone, an acetal, an alcohol, a lower alkyl, —CH=CH—CHO, —C(alkyl)=N—OH, —C(alkyl)=N—O(alkyl) and other keto derivatives, —CH=NOH, —CH=NO(alkyl), and other aldehyde derivatives, —C(alkyl)=NH—NH—$CONH_2$, an O-phenyl or —$OCH_2$(phenyl) group, —C(cycloalkyl)=NOH, —C(cycloalkyl)=N—O(alkyl), an optionally substituted heterocycle;

a heterocycle comprising a sulphur hetero atom; a cycloalkyl; a bicyclic group and preferably a norbornyl group; a phenyl ring fused to a heterocycle comprising a nitrogen hetero atom or to a carbocycle or a heterocycle bearing a keto function; an unbranched or branched lower alkyl comprising from 1 to 8 carbon atoms; an unbranched or branched alkyne comprising from 1 to 8 carbon atoms and preferably 1 to 5 carbon atoms; a linear or branched alkyl mono- or polysubstituted with phenyl groups which are either unsubstituted or mono- or polysubstituted; a phenyl alkyl ketone in which the alkyl group is branched or unbranched or cyclic; a substituted or unsubstituted benzophenone; a substituted or unsubstituted, unbranched or branched or cyclic phenyl alcohol; an unbranched or branched alkene; a piperidyl group; a phenylcycloalkyl group; a polycyclic group, in particular a fluorenyl group, a naphthyl or polyhydronaphthyl group or an indanyl group; a phenol group; a ketone or keto derivative; a diphenyl group; a phenoxyphenyl group; a benzyloxyphenyl group;
as well as their pharmaceutically acceptable salts, their hydrates, their hydrated salts, the polymorphic crystalline structures and the tautomeric forms of these compounds.

The antagonist, the agonist or partial agonist activity of these compounds may be readily verified by biological test methods, in particular those defined in the present invention.

The subject of the invention is also, by way of new compounds, those compounds of formulae Ia and Ib not known in the prior art, including Patent Application WO 93/14070.

According to the invention, group X representing an amine is understood to mean a secondary or tertiary amine.

The alkyl, alkene, alkyne, keto, aldehyde, cycloalkyl, S-alkyl, O-alkyl, phenyl alcohol and phenyl-cycloalkyl groups mentioned above as well as in the remainder of the description and the claims of the present patent comprise from 1 to 8 carbon atoms, and preferably 1 to 5.

Likewise, keto derivatives are understood to mean any oxime, alkyloxime, hydrazone, acetal, aminal, ketal, thione, carbazone or semicarbazone group and the thio analogues of these derivatives.

Likewise, by mono- or polysubstituted phenyl and/or benzophenone groups, it is understood to mean that these groups are substituted with one or more identical or different substituents selected from halogen atoms, $OCF_3$, CHO, $CF_3$, $SO_2N(alkyl)_2$, $SO_2N(CH_3)_2$, $NO_2$, S(alkyl), S(aryl), $SCH_2$(phenyl), an unbranched or branched alkene, an unbranched or branched alkyne optionally substituted with a trialkylsilyl radical, —O(alkyl), —O(aryl), —$CH_2CN$, a ketone, an aldehyde, a sulphone, an acetal, an alcohol, a lower alkyl, —CH=CH—CHO, —C(alkyl)=N—OH, —C(alkyl)=N—O(alkyl) and other keto derivatives, —CH=NOH, —CH=NO(alkyl), and other aldehyde derivatives, —C(alkyl)=NH—NH—$CONH_2$, an O-phenyl or —$OCH_2$(phenyl) group, —C(cycloalkyl)=NOH, —C(cycloalkyl)=N—O(alkyl), an optionally substituted heterocycle.

The keto substituent is preferably selected from a linear- or branched-chain aliphatic ketone, it being possible for the said chain to comprise from 1 to 8 carbon atoms and optionally to bear a hydroxyl group, a cycloalkyl ketone, an aryl alkyl ketone or aryl alkenyl ketone in which the aryl group is unsubstituted or mono- or polysubstituted, or a heteroaryl ketone in which the heteroaryl unit is preferably monocyclic.

The acetal substituent preferably consists of an aliphatic acetal comprising from 1 to 8 carbon atoms and optionally bearing a hydroxyl radical.

Group Y representing a ketone is understood to mean, in particular, a ketone substituted with an alkyl or aryl group, it being possible for these groups to be substituted or unsubstituted.

As regards the heterocycles, these comprise from 1 to 3 hetero atoms, preferably sulphur, oxygen or nitrogen atoms.

The heterocycle substituent is preferably selected from an oxadiazole or an imidazole.

The present invention also relates to the addition salts formed by the compounds of formula Ia and Ib with pharmaceutically acceptable acids. The pharmaceutically acceptable salts comprise the non-toxic salts of inorganic or organic acids such as the hydrochloride, hydrobromide or maleate.

The present invention also encompasses the hydrates of the compounds of formula Ia or Ib, the hydrated salts of these compounds and the polymorphic crystalline structures. It should, moreover, be noted that the structure of the compounds according to the invention as illustrated by the formulae Ia and Ib represents only one of the possible tautomeric forms of these compounds, and that the latter may occur in other tautomeric forms. Hence the present invention also encompasses all the possible tautomeric forms of the compounds in question, whether these tautomers occur in isolated form or in the form of mixtures.

The compounds of formula Ia or Ib can exist in one or more isomeric forms, depending on the number of asymmetric centres in the molecule. Hence the invention relates both to all the optical isomers and to the racemic mixtures thereof and the corresponding diastereomers. The separation of the diastereoisomers and/or optical isomers may be performed according to methods known per se.

A preferred group of compounds according to the present invention is the group composed of the chemical compounds in which the chain A is a $(CH_2)_3$ group; X is an O or OCONH group; the chain B is a group $(CH_2)_n$ where n=0, 2 or 3; and Y is a cyclopentyl group, —$CH(CH_3)_2$, —CH(phenyl)$_2$, —$C(CH_3)_3$ or a phenyl group: p-substituted with —$COC_3H_7$, —$OCH_2$, —CO(cyclopropyl), —$C(CH_3)$=N—OH, —C(cyclopropyl)=NOH, —$C(CH_3)$=$NOCH_3$ or —C(cyclopropyl)=N—$OCH_3$, or m-substituted with —$COCH_3$ or —$CF_3$.

A preferred group of compounds according to the invention is composed of the chemical compounds corresponding to the formula (Ib) in which Y represents a mono- or polysubstituted phenyl group.

The present invention also relates to chemical compounds which are histamine $H_3$ receptor agonists or partial agonists and which correspond to the general formula (Ib) in which:

A represents —$(CH_2)_n$— where n is an integer which can vary between 1 and 8, preferably between 2 and 4, or —$CH_2CH(CH_3)$—;

X represents an oxygen atom; sulphur atom or —OCONH—; amine;

Y represents a branched or unbranched lower alkyl optionally mono- or polysubstituted with phenyl groups; an aryl radical such as a phenyl group substituted with a lower alkyl, $CF_3$, $NO_2$, $OCF_3$, an alcohol, an aldehyde, a ketone, —C(alkyl)=N—OH;

as well as their pharmaceutically acceptable salts, their hydrates, their hydrated salts, the polymorphic crystalline structures and the tautomeric forms of these compounds.

Such compounds may be used for the purpose of manufacturing a medicinal product which acts as $H_3$ receptor agonist or partial agonist, enabling the synthesis and/or release of histamine or of other neurotransmitters such as neuropeptides or noradrenaline in human or animal tissues to be inhibited by virtue of its action.

The compounds which are partial agonists are of special interest in that they provide for a normalization of transmissions without maximum activation or complete blockade of the $H_3$ receptor, as occurs, respectively, with complete agonists and with antagonists.

The said compounds may also be used in the form of pharmaceutical composition comprising a therapeutically effective amount of such a chemical compound (or of several, combined or otherwise), in a pharmaceutically acceptable excipient, intended for an agonist or partial agonist action on the said histamine receptors.

A preferred group of compounds which are agonists or partial agonists according to the present invention is the group composed of the chemical compounds in which: the chain A is a group $(CH_2)_n$ where n=2, 3 or 4; X is an O, S or OCONH group; and Y is a —$C(CH_3)_3$ or —$CH(phenyl)_2$ group or a phenyl group m-substituted with a —$COCH_3$, —$CF_3$, —$OCF_3$ or —$CH(CH_3)_2$ group.

Among these, preferred compounds which are partial agonists according to the present invention correspond, in particular, to Examples 1, 3, 5, 6, 7, 8, 10, 11, 12, 13, 14, 16, 17, 110, 111, 154 and 157 described below in the present description.

The compound of Example 6 is especially preferred.

Another preferred group of compounds which are agonists or partial agonists according to the present invention is the group composed of the compounds of formulae (Ib) in which A is —$(CH_2)_3$—, X is an amine group and Y represents a phenyl group which is substituted, especially meta-substituted, preferably with a $CF_3$, $COCH_3$ or $C_2H_5$ group.

Among these, preferred compounds which are agonists correspond, in particular, to Examples 154 and 156, the compound of Example 154 being especially preferred.

The subject of the present invention is also chemical compounds which are histamine $H_3$ receptor antagonists, corresponding to the general formula (Ia) or (Ib) in which:

the chain A represents an unbranched alkyl group —$(CH_2)_n$— where n is an integer which can vary between 1 and 8, preferably between 1 and 4; an unbranched alkene group comprising from 1 to 4 carbon atoms;

the group X represents —OCONH—; —OCON(alkyl)-; —OCON(alkene)-; —OCO—; —OCSNH—; —$CH_2$—; —O—; —$OCH_2CO$—; —CO—; —S—; amine; alkene;

the chain B represents an unbranched or branched lower alkyl comprising from 1 to 8 carbon atoms; —$(CH_2)_n$ (hetero atom)-, where the hetero atom is preferably an oxygen or sulphur atom (where n is an integer which can vary between 0 and 4);

the group Y represents a phenyl group, unsubstituted or mono- or polysubstituted with one or more identical or different substituents selected from halogen atoms, a linear or branched alkyl, $CF_3$, $SO_2N(alkyl)_2$, S(alkyl), S(aryl), $SCH_2(phenyl)$, $SO_2N(CH_3)_2$, $SCH_3$, an unbranched or branched alkene, an unbranched or branched alkyne optionally substituted with a trialkylsilyl radical, $OCH_3$, $NO_2$, $OCF_3$, a ketone, an alcohol, a sulphone, an acetal, $CH_2CN$, an aldehyde, —(alkyl)C=NOH, —CH=N—O(alkyl), —(alkyl)C=NO(alkyl), —C(alkyl)=N—$NHCONH_2$, —CH=CH—CHO, —O(alkyl), —O(aryl), —CH=NOH; —$OCH_2$(phenyl), optionally substituted heterocycle;

a heterocycle comprising a sulphur hetero atom; a cycloalkyl; a bicyclic group, preferably a norbornyl group; a phenyl ring fused to a heterocycle comprising a nitrogen hetero atom or to a carbocycle or to a heterocycle bearing a keto function; an unbranched or branched alkyl comprising from 1 to 8 carbon atoms; an alkyl polysubstituted with phenyl groups which are either unsubstituted or mono- or polysubstituted; a phenyl alkyl ketone in which the alkyl group is branched or unbranched or cyclic; a substituted or unsubstituted benzophenone; a substituted or unsubstituted, unbranched or branched or cyclic phenyl alcohol; an unbranched or branched alkyne; an unbranched or branched alkene; a piperidyl group; a phenylcycloalkyl; a polycyclic group, in particular a fluorenyl group, a naphthyl or polyhydronaphthyl group or an indanyl group; a phenol group; a ketone or keto derivative; a diphenyl group; a phenoxyphenyl group; a benzyloxyphenyl group; as well as their pharmaceutically acceptable salts, their hydrates, their hydrated salts, the polymorphic crystalline structures and the tautomeric forms of these compounds.

Such compounds may be used for the purpose of manufacturing a medicinal product which acts as histamine $H_3$ receptor antagonist, enabling the synthesis and/or release of histamine or of other neurotransmitters such as neuropeptides or noradrenaline in human or animal tissues to be promoted by virtue of its action.

The said compounds may also be used in the form of pharmaceutical composition comprising a therapeutically effective amount of such a chemical compound (or of several, combined or otherwise), in a pharmaceutically acceptable excipient, intended for an antagonist action on the said histamine receptors.

A preferred group of compounds which are antagonists according to the present invention is the group composed of the chemical compounds in which the chain A is a —$(CH_2)_3$— group; X is an O or OCONH group; the chain B is a —$(CH_2)_2$— or —$(CH_2)_3$— group; and Y is a cyclopentyl group or a phenyl group p-substituted with —CO(cyclopropyl), —$COC_3H_7$, —$OCH_3$, —CHOH(cyclopropyl), —$C(CH_3)$=N—OH, —C(cyclopropyl)=N—OH, —$C(CH_3)$=N—$OCH_3$ or —C(cyclopropyl)=N—$OCH_3$.

Another preferred group of compounds which are antagonists is composed of the chemical compounds corresponding to the formula (Ib) in which Y represents a phenyl group at least monosubstituted with a ketone, an oxime, an acetal, a sulphone, an optionally substituted oxadiazole group or an unsaturated aliphatic group, in particular a linear or branched alkyne group optionally substituted with a trialkylsilyl radical.

Among these compounds, those for which Y represents a phenyl group disubstituted with, as the other substituent, a group preferably selected from halogen atoms and a lower alkyl group are preferred.

Yet another preferred group of compounds which are antagonists is composed of the chemical compounds corresponding to the formula (Ib) in which Y represents a phenyl group fused to a carbocycle bearing a keto function.

Yet another preferred group of compounds which are antagonists is composed of the chemical compounds corresponding to the formula (Ib) in which Y represents a phenyl group fused to a heterocycle bearing a keto function.

Among the compounds of which the above mentioned groups are composed, those in which A represents a —$(CH_2)_3$— group and X represents —O— are especially preferred.

Among these compounds, preferred compounds which are antagonists according to the present invention correspond, in particular, to Examples 30, 68, 78, 81, 82, 85, 88, 92, 93, 95, 112, 115, 122, 125, 126, 127, 128, 129, 134, 135, 136, 138, 139, 141, 142, 143, 144, 145, 146, 147, 149, 16G, 163, 166, 174, 175 and 176.

The compound of Example 81 is especially preferred.

The compounds of Examples 25, 107 and 108 are not preferred.

The examples which are given in Table I below, without implied limitation, illustrate the present invention.

The compounds of Examples 1 to 20, 110, 111 and 154 to 159 are agonists or partial agonists for the said receptors, and Examples 21 to 109, 112 to 153 and 160 to 183 are antagonists for the said receptors.

TABLE I

| Example | Chain A | X | Chain B | Y |
|---|---|---|---|---|
| 1 | $(CH_2)_3$ | OCONH | / | $—C(CH_3)_3$ |
| 2 | $(CH_2)_3$ | OCONH | / | CH(C6H5)2 with methyl |
| 3 | $(CH_2)_3$ | OCONH | / | CH(C6H5)2 with ethyl |
| 4 | $(CH_2)_2$ | OCONH | / | CH(C6H5)2 with ethyl |
| 5 | $(CH_2)_3$ | O | / | $—(CH_2)_2—CH(CH_3)_2$ |
| 6 | $(CH_2)_3$ | O | / | $—(CH_2)_2—C(CH_3)_3$ |
| 7 | $(CH_2)_3$ | O | / | $—(CH_2)_3—CH(CH_3)_2$ |
| 8 | $(CH_2)_3$ | O | / | 3-methyl-5-CF3 phenyl (m-methyl, CF3) |
| 9 | $(CH_2)_3$ | O | / | m-methyl, NO2 phenyl |
| 10 | $(CH_2)_2$ | S | / | 3,5-dimethyl-CF3 phenyl |
| 11 | $(CH_2)_3$ | O | / | m-methyl, OCF3 phenyl |
| 12 | $(CH_2)_3$ | O | / | m-methyl, iPr phenyl |

TABLE I-continued
| | | | | |
|---|---|---|---|---|
| 13 | (CH$_2$)$_3$ | O | / | 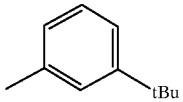 |
| 14 | (CH$_2$)$_3$ | O | / | 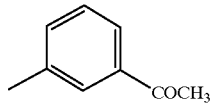 |
| 15 | (CH$_2$)$_3$ | O | / | 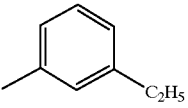 |
| 16 | (CH$_2$)$_4$ | O | / | 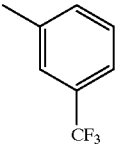 |
| 17 | (CH$_2$)$_4$ | O | / | 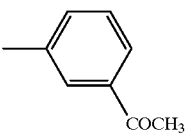 |
| 18 | (CH$_2$)$_3$ | O | / | 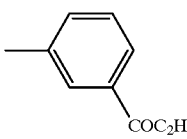 |
| 19 | (CH$_2$)$_3$ | O | / | 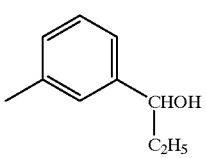 |
| 20 | (CH$_2$)$_3$ | O | / | 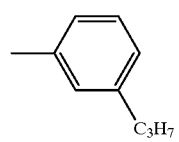 |
| 21 | (CH$_2$)$_3$ | O | / | 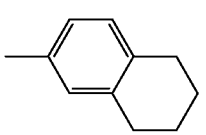 |
| 22 | (CH$_2$)$_3$ | O | / | 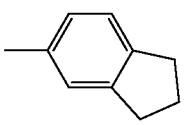 |

TABLE I-continued

| | | | | |
|---|---|---|---|---|
| 23 | (CH$_2$)$_3$ | O | / | 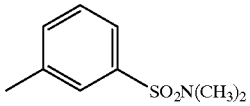 |
| 24 | (CH$_2$)$_3$ | O | / | 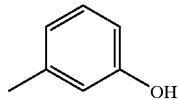 |
| 25 | (CH$_2$)$_3$ | O | / | 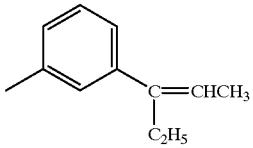 |
| 26 | (CH$_2$)$_3$ | O | / | 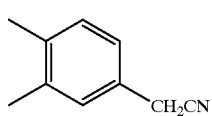 |
| 27 | (CH$_2$)$_3$ | O | / | 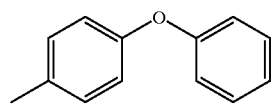 |
| 28 | (CH$_2$)$_3$ | OCONH | / | —(CH$_2$)$_2$CH$_3$ |
| 29 | (CH$_2$)$_3$ | OCONH | / | —(CH$_2$)$_3$CH$_3$ |
| 30 | (CH$_2$)$_3$ | OCONH | / | —(CH$_2$)$_4$CH$_3$ |
| 31 | (CH$_2$)$_3$ | OCONH | / | —(CH$_2$)$_5$CH$_3$ |
| 32 | (CH$_2$)$_3$ | OCONH | / | —(CH$_2$)$_6$CH$_3$ |
| 33 | (CH$_2$)$_3$ | OCONH | / | —(CH$_2$)$_7$CH$_3$ |
| 34 | (CH$_2$)$_3$ | OCONH | / | 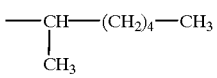 |
| 35 | (CH$_2$)$_3$ | OCONH | / | 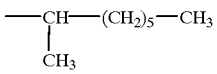 |
| 36 | (CH$_2$)$_3$ | OCONH | / | —(CH$_2$)$_2$CH(CH$_3$)$_2$ |
| 37 | (CH$_2$)$_3$ | OCONH | / | 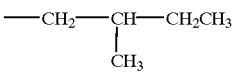 |
| 38 | (CH$_2$)$_3$ | OCONH | / | 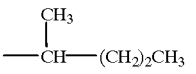 |
| 39 | (CH$_2$)$_3$ | OCON(propyl) | / | —(CH$_2$)$_2$CH$_3$ |
| 40 | (CH$_2$)$_3$ | OCON(allyl) | / | —CH$_2$—CH=CH$_2$ |
| 41 | (CH$_2$)$_3$ | OCO | / | 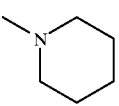 |

TABLE I-continued
| | | | | |
|---|---|---|---|---|
| 42 | (CH$_2$)$_3$ | OCONH | / | 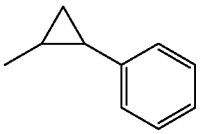 |
| 43 | (CH$_2$)$_2$ | OCONH | CH$_2$ | 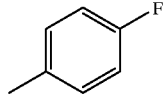 |
| 44 | (CH$_2$)$_3$ | OCONH | CH$_2$—CH—CH$_3$ | 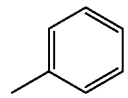 |
| 45 | (CH$_2$)$_3$ | OCONH | CH$_2$ | 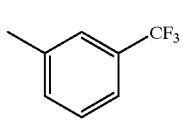 |
| 46 | (CH$_2$)$_3$ | OCONH | / | 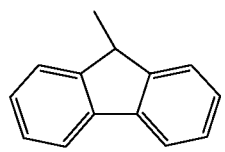 |
| 47 | (CH$_2$)$_3$ | OCONH | / | 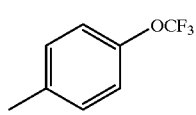 |
| 48 | (CH$_2$)$_3$ | OCONH | CH$_2$ | 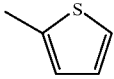 |
| 49 | (CH$_2$)$_3$ | OCSNH | / | 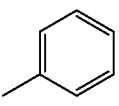 |
| 50 | (CH$_2$)$_2$ | CO | / | 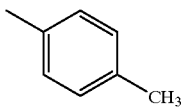 |
| 51 | CH=CH—CH$_2$ | CH$_2$ | / | 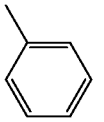 |
| 52 | (CH$_2$)$_2$ | CH$_2$ | CH$_2$ | 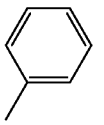 |
| 53 | CH$_2$ | O | CH$_2$ | 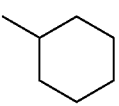 |

TABLE I-continued
| | | | | |
|---|---|---|---|---|
| 54 | CH$_2$ | O | CH$_2$ | 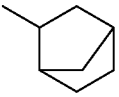 |
| 55 | (CH$_2$)$_3$ | O | (CH$_2$)$_3$ | 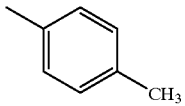 |
| 56 | (CH$_2$)$_3$ | O | CH$_2$ | 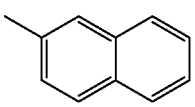 |
| 57 | (CH$_2$)$_3$ | O | CH$_2$ | 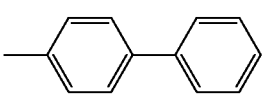 |
| 58 | (CH$_2$)$_3$ | O | (CH$_2$)$_3$ | 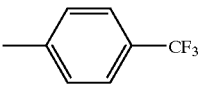 |
| 59 | (CH$_2$)$_3$ | O | CH$_2$ | 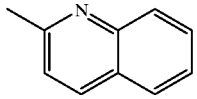 |
| 60 | (CH$_2$)$_3$ | O | (CH$_2$)$_3$ | 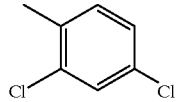 |
| 61 | (CH$_2$)$_3$ | O | (CH$_2$)$_2$ | 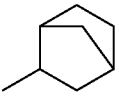 |
| 62 | (CH$_2$)$_3$ | O | (CH$_2$)$_3$ | 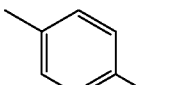 |
| 63 | (CH$_2$)$_3$ | O | (CH$_2$)$_2$ | 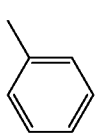 |
| 64 | (CH$_2$)$_3$ | O | / | (CH$_2$)$_6$—CH$_3$ |
| 65 | (CH$_2$)$_3$ | O | / | CH$_2$—CH(CH$_3$)$_2$ |
| 66 | (CH$_2$)$_3$ | O | (CH$_2$)$_2$ | 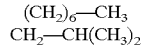 |
| 67 | (CH$_2$)$_3$ | O | / | (CH$_2$)$_3$—C≡CH |
| 68 | (CH$_2$)$_3$ | O | (CH$_2$)$_2$O |  |

TABLE I-continued

| | | | | |
|---|---|---|---|---|
| 69 | (CH₂)₃ | O | CH₂ | 4-(methylthio)phenyl (p-CH₃-C₆H₄-SCH₃) |
| 70 | CH=CHCH₂ | O | (CH₂)₃ | 4-fluoro-methylphenyl (p-CH₃-C₆H₄-F) |
| 71 | (CH₂)₃ | O | / | diphenylmethyl (CH(C₆H₅)₂ with CH₃) |
| 72 | (CH₂)₃ | O | / | 1-(4-fluorophenyl)-1-phenylethyl |
| 73 | (CH₂)₃ | O | / | 1,1-bis(4-fluorophenyl)ethyl |
| 74 | (CH₂)₃ | OCH₂CO | / | methylphenyl |
| 75 | (CH₂)₃ | OCH₂CO | / | 3-nitro-methylphenyl |
| 76 | (CH₂)₃ | O | / | 4-(4-methylphenyl)butan-2-one |
| 77 | (CH₂)₃ | O | / | 4-methylbenzaldehyde |
| 78 | (CH₂)₃ | O | / | 4′-methylacetophenone |

TABLE I-continued
| | | | | |
|---|---|---|---|---|
| 79 | (CH₂)₃ | O | / | 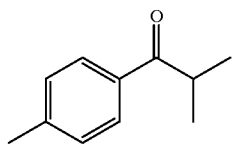 |
| 80 | (CH₂)₃ | O | / | 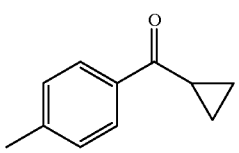 |
| 81 | (CH₂)₃ | O | / | 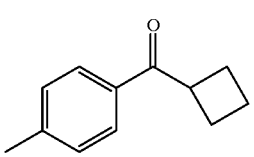 |
| 82 | (CH₂)₃ | O | / | 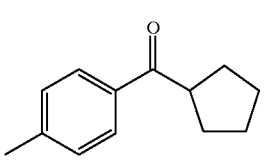 |
| 83 | (CH₂)₃ | O | / | 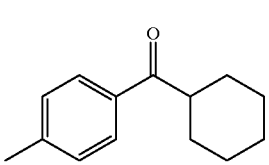 |
| 84 | (CH₂)₃ | O | / | 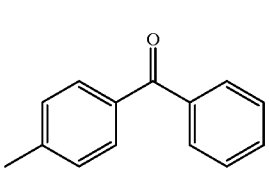 |
| 85 | (CH₂)₃ | O | / | 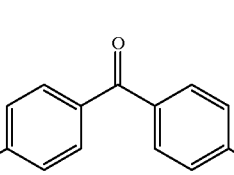 |
| 86 | (CH₂)₃ | O | / | 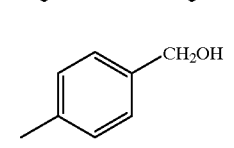 |
| 87 | (CH₂)₃ | O | / | 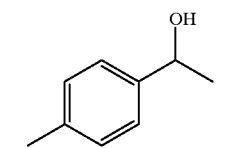 |
| 88 | (CH₂)₃ | O | / |  |

TABLE I-continued

| | | | | |
|---|---|---|---|---|
| 89 | (CH$_2$)$_3$ | O | / | 4-methylphenyl-CH(OH)-CH(CH$_3$)$_2$ |
| 90 | (CH$_2$)$_3$ | O | / | 4-methylphenyl-CH(OH)-cyclopropyl |
| 91 | (CH$_2$)$_3$ | O | / | 4-methylphenyl-CO-CH$_2$CH$_2$CH$_3$ |
| 92 | (CH$_2$)$_3$ | O | / | 4-methylphenyl-C(=NOH)-CH$_3$ |
| 93 | (CH$_2$)$_3$ | O | / | 4-methylphenyl-C(=NOCH$_3$)-CH$_3$ |
| 94 | (CH$_2$)$_3$ | O | / | 4-methylphenyl-CH$_2$-CO-CH$_3$ |
| 95 | (CH$_2$)$_3$ | O | / | 4-methylphenyl-O-CH$_3$ |
| 96 | (CH$_2$)$_3$ | OCONH | / | 4-methylphenyl-CO-CH$_3$ |
| 97 | (CH$_2$)$_3$ | OCONH | / | 3-methylphenyl-CO-CH$_3$ |
| 98 | (CH$_2$)$_3$ | O | / | —(CH$_2$)$_2$CO CH$_3$ |
| 99 | (CH$_2$)$_3$ | O | (CH$_2$)$_2$O | CH$_3$ |

TABLE I-continued
| | | | | |
|---|---|---|---|---|
| 100 | (CH$_2$)$_3$ | O | (CH$_2$)$_3$ | 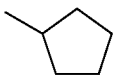 |
| 101 | (CH$_2$)$_3$ | OCONH | / | —CH(CH$_3$)$_2$ |
| 102 | (CH$_2$)$_3$ | OCONH | / | 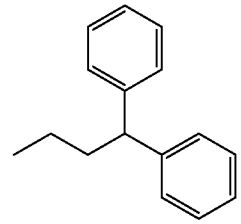 |
| 103 | (CH$_2$)$_2$ | CH$_2$ | (CH$_2$)$_5$ | CH$_3$ |
| 104 | (CH$_2$)$_3$ | O | / | 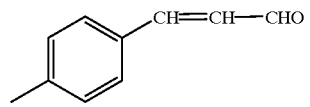 |
| 105 | (CH$_2$)$_3$ | O | / | 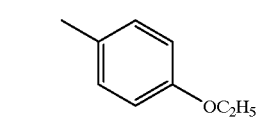 |
| 106 | (CH$_2$)$_2$ | O | / | 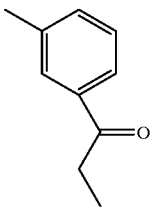 |
| 107 | (CH$_2$)$_3$ | O | / | 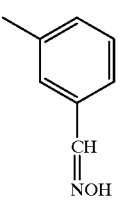 |
| 108 | (CH$_2$)$_3$ | O | / | 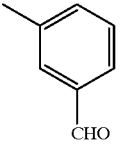 |
| 109 | (CH$_2$)$_3$ | O | / | 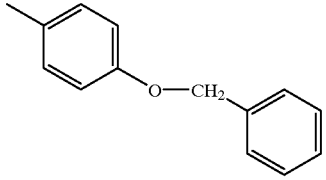 |
| 110 | (CH$_2$)$_3$ | OCONH | / | —C(CH$_3$)$_2$—C$_2$H$_5$ |
| 111 | (CH$_2$)$_3$ | OCONH | CH$_2$ | —C(CH$_3$)$_3$ |
| 112 | (CH$_2$)$_3$ | OCONH | CH$_2$ | —CH=CH$_2$ |

TABLE I-continued
| | | | | |
|---|---|---|---|---|
| 113 | (CH$_2$)$_3$ | OCONH | / | 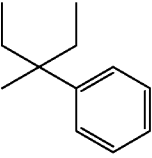 |
| 114 | (CH$_2$)$_3$ | OCONH | / | 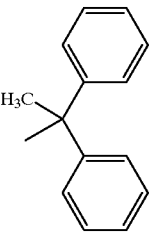 |
| 115 | (CH$_2$)$_3$ | OCONH | / | 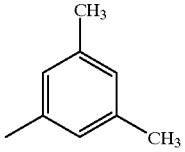 |
| 116 | (CH$_2$)$_2$ | O | / | —C(CH$_3$)$_3$ |
| 117 | (CH$_2$)$_3$ | O | / | —C(CH$_3$)$_3$ |
| 118 | (CH$_2$)$_3$ | O | CH$_2$ | —CH=CH$_2$ |
| 119 | (CH$_2$)$_3$ | O | (CH$_2$)$_3$ | —CH=CH$_2$ |
| 120 | (CH$_2$)$_3$ | O | CH$_2$ | —C≡CH |
| 121 | (CH$_2$)$_3$ | O | / | 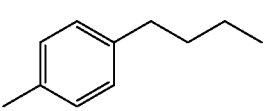 |
| 122 | (CH$_2$)$_3$ | O | / | 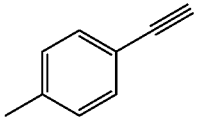 |
| 123 | (CH$_2$)$_3$ | O | / | 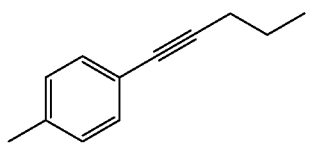 |
| 124 | (CH$_2$)$_3$ | O | / | 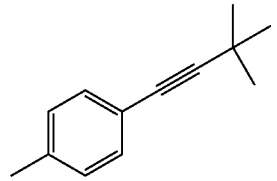 |
| 125 | (CH$_2$)$_3$ | O | (CH$_2$)$_3$ | 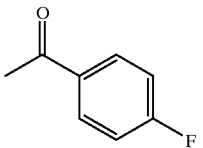 |

TABLE I-continued
| 126 | (CH₂)₂ | O | / | 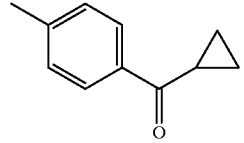 |
| 127 | (CH₂)₃ | O | / | 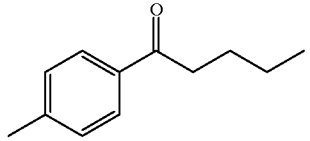 |
| 128 | (CH₂)₃ | O | / | 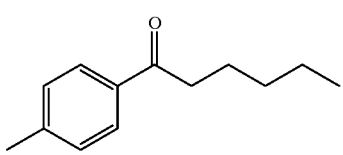 |
| 129 | (CH₂)₃ | O | / | 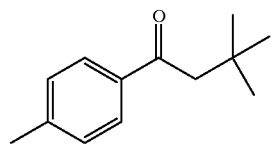 |
| 130 | (CH₂)₃ | O | / | 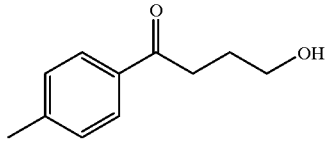 |
| 131 | (CH₂)₃ | O | / | 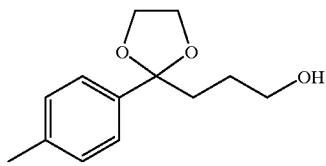 |
| 132 | (CH₂)₃ | O | / | 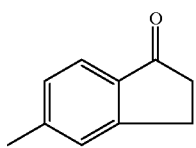 |
| 133 | (CH₂)₃ | O | / | 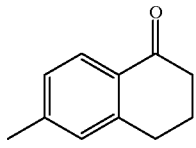 |
| 134 | (CH₂)₃ | O | / | 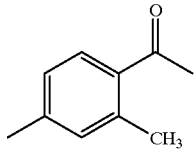 |

TABLE I-continued

| | | | | |
|---|---|---|---|---|
| 135 | (CH₂)₃ | O | / | 2-fluoro-4-methylphenyl methyl ketone |
| 136 | (CH₂)₃ | O | / | 1-(2-fluoro-4-methylphenyl)propan-1-one |
| 137 | (CH₂)₃ | O | / | (4-methylphenyl)(thiophen-2-yl)methanone |
| 138 | (CH₂)₃ | O | / | 4-methylbenzaldehyde oxime |
| 139 | (CH₂)₃ | O | / | 1-(4-methylphenyl)propan-1-one oxime |
| 140 | (CH₂)₃ | O | / | 1-(4-methylphenyl)butan-1-one oxime |
| 141 | (CH₂)₃ | O | / | 1-(4-methylphenyl)pentan-1-one oxime |
| 142 | (CH₂)₃ | O | / | 1-(4-methylphenyl)hexan-1-one oxime |
| 143 | (CH₂)₃ | O | / | cyclopropyl(4-methylphenyl)methanone oxime |

TABLE I-continued

| # | | | | Structure |
|---|---|---|---|---|
| 144 | (CH₂)₃ | O | / | 1-(4-methyl-2-methylphenyl)ethanone oxime |
| 145 | (CH₂)₃ | O | / | 1-(2-fluoro-4-methylphenyl)ethanone oxime |
| 146 | (CH₂)₃ | O | / | 4-methylbenzaldehyde O-methyl oxime |
| 147 | (CH₂)₃ | O | / | 1-(4-methylphenyl)ethanone semicarbazone |
| 148 | (CH₂)₃ | O | / | 6-methyl-1,3-benzoxathiol-2(3H)-one |
| 149 | (CH₂)₃ | O | / | 2-methyl-5-(4-methylphenyl)-4H-1,3,4-oxadiazine |
| 150 | (CH₂)₃ | O | / | 1-fluoro-4-[(4-methylphenyl)peroxy]benzene |
| 151 | (CH₂)₃ | O | / | 1-(4-methylphenyl)-3-phenyl-2-propen-1-one |
| 152 | (CH₂)₃ | O | / | 1-(4-methylphenyl)heptan-1-one |
| 153 | (CH₂)₃ | O | / | 1-(4-methylphenyl)-2-phenylethanone |

TABLE I-continued

| Example | Chain A | X | Chain B | Y: ⟨phenyl⟩-R with R: |
|---------|---------|---|---------|----------------------|
| 154 | (CH$_2$)$_3$ | NH | / | 3-CF$_3$ |
| 155 | (CH$_2$)$_3$ | | | |
| 156 | (CH$_2$)$_3$ | NH | / | 3-C$_2$H$_5$ |
| 157 | (CH$_2$)$_2$ | S | / | 3-COCH$_3$ |
| 158 | (CH$_2$)$_3$ | O | / | 3-C(=NOH)CH$_3$ |
| 159 | CH$_2$CH(CH$_3$) | S | / | 3-CF$_3$ |
| 160 | (CH$_2$)$_2$ | O | / | 4-CH$_3$ |
| 161 | (CH$_2$)$_2$ | O | / | 4-COC$_2$H$_5$ |
| 162 | (CH$_2$)$_3$ | O | / | 4-CH(CH$_3$)C$_2$H$_5$ |
| 163 | (CH$_2$)$_3$ | O | / | 4-C$_2$H$_5$ |
| 164 | (CH$_2$)$_3$ | O | / | 4-(1-imidazolyl) |
| 165 | (CH$_2$)$_3$ | O | / | 4-SO$_2$N(CH$_3$)$_2$ |
| 166 | (CH$_2$)$_3$ | O | / | 4-SCH$_3$ |
| 167 | (CH$_2$)$_3$ | O | / | 4-SCH$_2$Ph |
| 168 | (CH$_2$)$_3$ | S | / | 3-COCH$_3$ |
| 169 | (CH$_2$)$_3$ | NH | / | 4-C$_2$H$_5$ |
| 170 | (CH$_2$)$_3$ | NH | / | 4-Cl |

| Example | Chain A | X | Chain B | Y |
|---------|---------|---|---------|---|
| 171 | (CH$_2$)$_3$ | O | / | 4-(trimethylsilylethynyl)phenyl |
| 172 | (C$_2$)$_3$ | O | / | 4-(propynyl)phenyl |
| 173 | (CH$_2$)$_3$ | O | / | 4-isopropylphenyl |
| 174 | (CH$_2$)$_3$ | O | / | CH$_3$ |
| 175 | (CH$_2$)$_3$ | O | CH$_2$ | CH$_3$ |
| 176 | (CH$_2$)$_3$ | O | (CH$_2$)$_2$ | CH$_3$ |
| 177 | (CH$_2$)$_3$ | O | / | cyclopropyl |

TABLE I-continued

| 178 | (CH₂)₃ | O | CH₂ |  |
| --- | --- | --- | --- | --- |
| 179 | (CH₂)₃ | CH₂ | (CH₂)₂ | 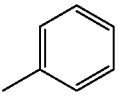 |
| 180 | (CH₂)₃ | OCONH | / | 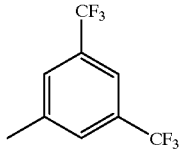 |
| 181 | (CH₂)₃ | OCONH | CHC(CH₃)₃—CH₂ | 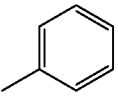 |
| 182 | (CH₂)₃ | OCONH | CH | (C₂H₅)₂ |
| 183 | (CH₂)₂ | CH=CH | (CH₂)₂ | 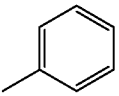 |

The different routes or method of synthesis of the compounds in Table I are detailed below.

Methods of Synthesis of Compounds having a Structural Component

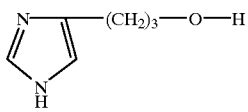

Synthesis of 1-(triphenylmethyl)-4-(3-hydroxypropyl)-imidazole

In a reaction flask equipped for hydrogenation, 10 g of urocanic acid (72.4 mmol) are dissolved in 200 ml of water. 1 g of Pd/C (10%) are added and hydrogenation is performed at 50° C. for 4 hours. The catalyst is filtered off and the water evaporated off, giving 3-(4-imidazolyl)propionic acid which appears in the form of a white powder (8.8 g; 86%); m.p.: 209–211° C. (3-Imidazol-4-yl)propionic acid (6 g, 42 mmol) is dissolved in absolute ethanol (204 ml), and a catalytic amount of concentrated sulphuric acid (2 ml) is added. The resulting mixture is heated to reflux for 16 hours. The solvent is evaporated off, which gives an oily residue which is dissolved in 45 ml of water. The solution is neutralized with sodium hydrogencarbonate, and 4-(3-carboethoxypropyl)-1H-imidazole is extracted with ethyl acetate; an oil (5.1 g; 72%) is obtained. The 4-(3-carboethoxypropyl)-1H-imidazole (5.4 g, 32 mmol) is dissolved in 4 ml of anhydrous dimethylformamide. 3.4 g of triethylamine (33.6 mmol) and 9.3 g of triphenylmethyl chloride (33.6 mmol) are added, and the mixture is stirred at room temperature under nitrogen for 4 hours. The mixture is poured onto crushed ice (60 g), which gives a white precipitate which is recrystallized from diethyl ether (9.2 g; 70%), giving 1-(triphenylmethyl)-4-(3-carboethoxypropyl)-1H-imidazole; m.p.: 134° C.

The above ester (7.5 g; 18.3 mmol), dissolved in freshly distilled THF (75 ml), is added dropwise to a solution of 0.8 g of lithium aluminium hydride (21 mmol) in freshly distilled THF (45 ml) in the cold and with stirring. Stirring is continued at room temperature for 12 hours, and the lithium aluminium hydride is then decomposed by adding saturated sodium sulphate solution dropwise. The resulting complex is filtered off, and the THF is dried over magnesium sulphate, giving an oil which is reduced in ethyl acetate to give 1-(triphenylmethyl)-4-(3-hydroxypropyl)-1H-imidazole in the form of a white powder (5.8 g; 87%); m.p.: 130° C.

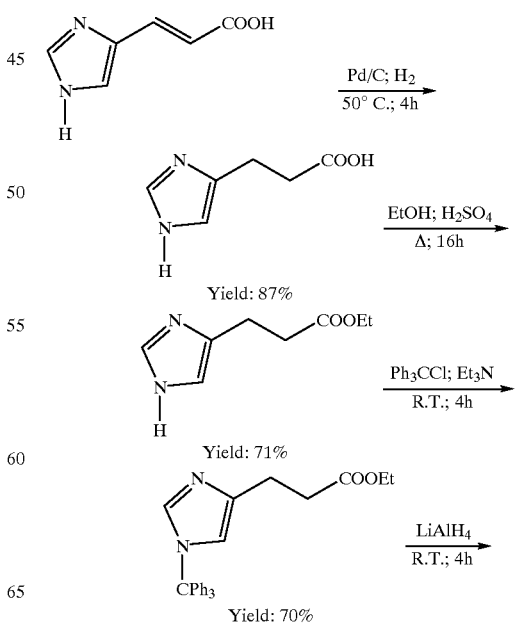

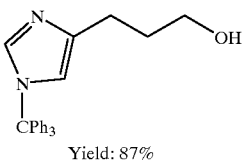

Yield: 87%

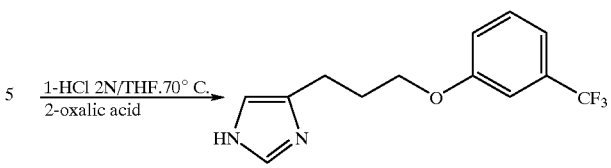

Method A

4-(3-(3-Trifluoromethylphenoxy)propyl)-1H-imidazole oxalate 300 mg of 1-(triphenylmethyl)-4-(3-hydroxypropyl)-1H-imidazole (0.81 mmol) are dissolved in 8 ml of freshly distilled THF. 277 mg of triphenylphosphine (1.06 mmol) and 145 mg m-trifluoromethylphenol are added thereto, and the resulting mixture is cooled and stirred for 5 minutes under nitrogen. Diethyl azodicarboxylate (184 mg; 1.06 mmol), dissolved in freshly distilled THF (4 ml), is added gradually to the reaction mixture and while stirring continuously at room temperature for 12 hours. After removal of the solvent in vacuo, column chromatography (SiO$_2$; first eluent: petroleum spirit; second eluent: petroleum spirit/diethyl ether (50:50)) performed on the crude reaction mixture gives a white powder which is reduced in petroleum ether to give an oil of 1-(triphenylmethyl)-4-[3-(trifluoromethylphenoxy)-propyl]-1H-imidazole. The latter (210 mg; 0.41 mmol) is heated at 70° C. for 3 hours in THF (5 ml) and 2N HCl (12 ml). The THF is removed under reduced pressure and Ph$_3$COH is extracted with diethyl ether. The aqueous phase is neutralized with potassium carbonate and the product is extracted into diethyl ether or chloroform. This solution is dried and evaporated, giving an oil which is dissolved in 2-propanol. Oxalic acid (1.5 equivalents) is added and the abovementioned product (on addition of diethyl ether) in the form of the oxalate, m.p.: 204–208° C.

The appropriate substituted phenols to be used in method A are obtained on the market, except for the following compounds which are synthesized (but which are known compounds):

- 3-propanoylphenol (m.p.: 78–80° C.) for Example 18 (lit. T. Geoffrey, P. Bruneau, G. C. Crawley, M. P. Edwards, S. J. Foster, J. F. Girodeau, J. F. Kingston and R. M. McMillan, J. Med. Chem. 1991, 34, 2176)
- 3-(1-hydroxypropyl)phenol (m.p.: 106–108) for Example 19 (lit. Geoffrey et al., vide supra)
- 3-propylphenol (b.p.: 125° C. at 24 mm Hg) for Example 20 (lit. C. F. Carvalho and M. V. Sargent, J. Chem. Soc. Perk. Trans. 1. 1984, 1621–1627)

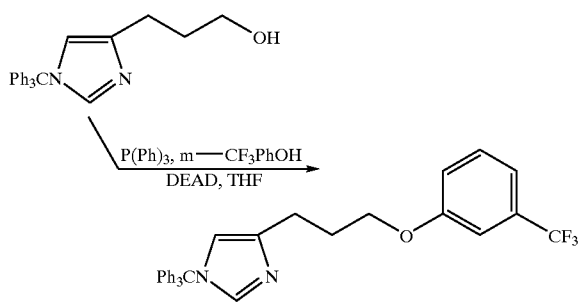

Method B

4-[2-(3-Trifluoromethylphenyl)thioethyl]-1H-imidazole oxalate 0.18 g (4.5 mmol) of sodium hydride (60% suspension in mineral oil) is added gradually to a cold solution of 3-trifluoromethylthiophenol (1.6; 8.9 mmol) in dimethylformamide. The mixture is stirred under nitrogen at room temperature for 1 hour. 0.15 g of 4-(2-chloroethyl)-1H-imidazole (0.89 mmol) and 0.010 g of tetrabutylammonium iodide are added and the mixture is stirred at 80° C. for 1 hour. The solvent is evaporated off and the oily residue is reduced with diethyl ether and then filtered. The product is then extracted from the filtrate with dilute HCl. The aqueous phase is washed again with diethyl ether and then alkalized with potassium carbonate, the product is extracted with chloroform to give an oil which is subjected to column chromatography (SiO$_2$; first eluent: chloroform; second eluent: chloroform/methanol (97:3)), and the product is then converted to an oxalate salt; m.p.: 158–160° C.

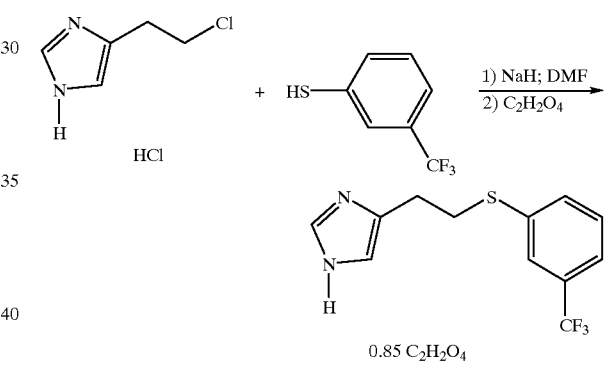

Method C

4-[4-(3-Ethanoylphenoxy)butyl]-1H-imidazole oxalate 2.87 g of 3-ethanoylphenol (21 mmol) in anhydrous DMF (30 ml) is cooled to 5° C. (ice bath) under an argon atmosphere, and 0.37 g of sodium hydride (60% suspension in mineral oil; 9.25 mmol) are then added. The mixture is stirred at 5° C. for 10 minutes and then at 20° C. for 2 hours. 0.70 g of 2-(t-butyldimethylsilyl)-5-(4-chlorobutyl)-1-(dimethylsulphamoyl)imidazole (1.85 mmol) (synthesized as described by R. C. Vollinga, W. M. P. B. Menge and H. Timmerman, Rec., Trav., Chem. Pays-Bas, 1993, 112, 123–125) and 45 mg of tetrabutylammonium iodide are added and the mixture is heated at 80° C. under argon for 3 days, then cooled to 20° C. and diluted with diethyl ether until the solution becomes cloudy. The resulting solid is filtered off and the filtrate evaporated to dryness in vacuo, giving a dark orange oil. The latter is subjected to column chromatography (SiO$_2$; using an ethyl acetate/methanol mixture in the ratio 9:1) to give 1-(N,N-dimethylsulphamoyl)-5-[4(3-ethanoylphenoxy)butyl]imidazole in the form of a yellow oil.

This oil (0.408 g, 1.17 mmol) is heated. under reflux in 30 ml of 2M HCl for 12 hours, then cooled, washed with diethyl ether, alkalized with potassium carbonate and extracted (3×50 ml) with chloroform. The combined chloroform extracts are dried (MgSO$_4$) and evaporated, giving the free base in the form of a yellow oil (0.28 g), which is converted to oxalate salt in ethanol (10 ml) using 1.5 molar equivalents of oxalic acid (in 10 ml ethanol). The resulting solid is collected, reduced with EtOH and recrystallized from EtOH, giving the desired product. M.p.: 168–170° C.

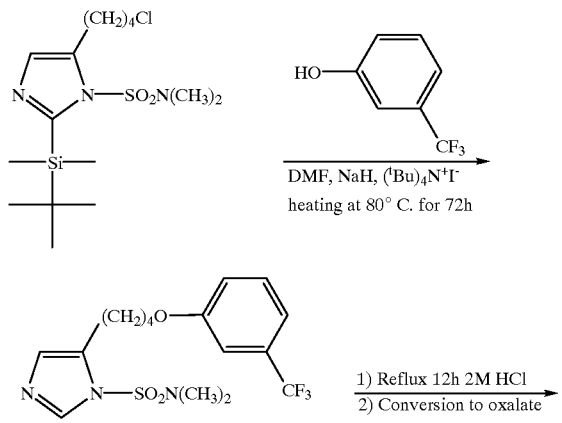

0.71 g of diethyl azodicarboxylate (4.07 mmol, 1.5 equiv.), dissolved in 10 ml of freshly distilled THF, is added gradually to the reaction mixture, and continuous stirring is maintained for 16 hours at 20° C. After removal of the solvent under reduced pressure, the resulting oil is subjected to column chromatography (SiO$_2$; ethyl acetate/hexane, 3:7), giving a yellow oil. This oil (0.5 g; 9.96 mmol) in ethanol (15 ml) and 5% potassium hydroxide (10 ml) are heated under reflux for 30 min. The mixture is acidified with 2N HCl (cooled on an ice bath) and extracted with chloroform: the organic extract is dried and the solvent removed under reduced pressure, leaving an oil. This oil is purified by column chromatography (SiO$_2$; chloroform), then dissolved in 8 ml of THF and heated at 80° C. for 5 hours in 2N HCl (12 ml). After cooling, the THF is removed under reduced pressure and Ph$_3$COH is extracted with diethyl ether. The aqueous phase is neutralized with potassium carbonate solution and the product is extracted with chloroform (3×100 ml). The combined chloroform extracts are dried (MgSO$_4$) and evaporated under reduced pressure to give an oil, which is dissolved in 2-propanol (2 ml) and converted to oxalate using 1.5 equivalents of oxalic acid and precipitating the product by adding diethyl ether; m.p.: 138–140° C.

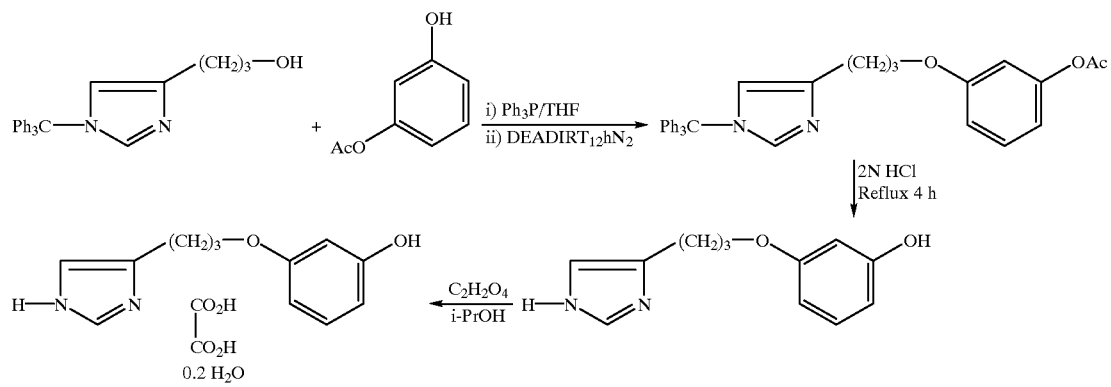

-continued

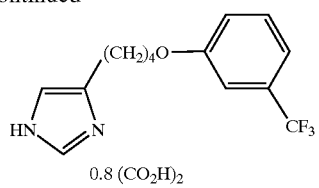

Method D

Preparation of 4-[3-(3-hydroxyphenoxy)propyl]-1H-imidazole oxalate

A mixture of resorcinol monoacetate (0.41 g, 2.71 mmol), 1-(triphenylaethyl-4-(3-hydroxypropyl)-1H-imidazole (1 g; 2.71 mmol) and triphenylphospine (1.06 g, 4.07 mmol, 1.5 equivalents) in anhydrous THF (30 ml) is cooled and stirred for 10 minutes under nitrogen.

Method E

4-{3-[3-(2-Penten-3-yl)phenoxy]propyl}-1H-imidazole trifluoroacetate 3-(3-Hydroxy-3-pentanyl)phenol, m.p. 78–80° C., is synthesized as described by M. Satomura in Japanese Patent No. 04 82867 A2 (Chem. Abstr., 1992, 117, 130911).

A mixture of this phenol (0.3 g, 1.66 mmol), 1-(triphenylmethyl)-4-(3-hydroxypropyl)imidazole (0.61 g, 1.66 mmol) and triphenylphosphine (0.65 g; 2.5 mmol; 1.5 equiv.) in 30 ml of anhydrous THF is cooled and stirred for 10 minutes under nitrogen. 0.57 g of diethyl azodicarboxylate (2.5 mmol; 1.5 equiv.), dissolved in 10 ml of freshly distilled THF, is added slowly to the reaction mixture and stirred continuously at room temperature for 16 hours. After removal of the solvent under reduced pressure, the resulting oil is purified by column chromatography (SiO$_2$; eluent: ethyl acetate/hexane 3:7).

The purified oil is dissolved in THF (8 ml) and heated with 2N HCl at 80° C. for 5 hours.

After cooling, the THF is removed under reduced pressure and Ph$_3$COH is extracted with diethyl ether. The aqueous phase is neutralized with potassium carbonate solution and the product is extracted into chloroform (3×100 ml). The combined chloroform extracts are dried and evaporated under reduced pressure to give an oil. This oil in 2 ml of 2-propanol is converted to oxalate and precipitated with diethyl ether. The solid product is collected and purified by preparative HPLC to give the trifluoroacetate salt in the form of white crystals, m.p.: 169–171° C. from 2-propanol.

$^1$H NMR and HPLC show that the compound contains 2 isomers (E/Z) in the ratio 4:1.

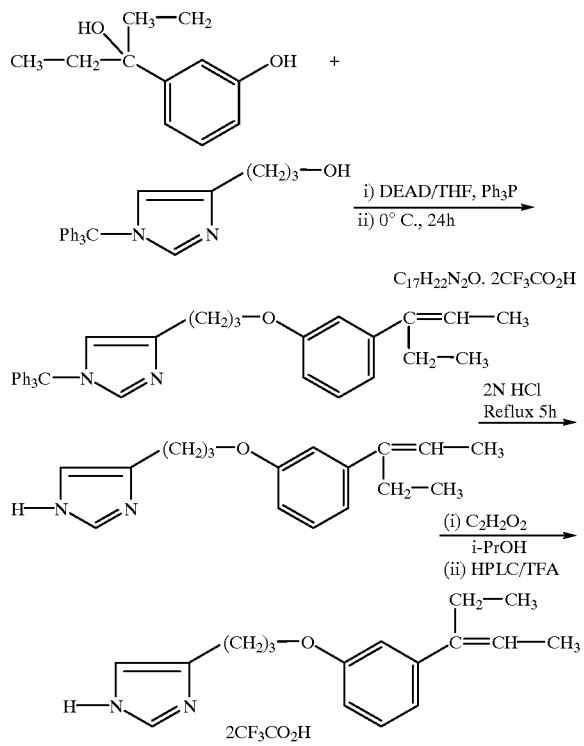

This compound is purified by preparative HPLC and two isomers are obtained in the ration 4:1 (E/Z)

Method F 6 ml of 1.5M n-butyllithium in THF at −78° C. are added slowly to 2 g of a solution, cooled and stirred under nitrogen at −78° C., of 2-(tert-butyldimethylsilyl)-1-(dimethylsulphamoyl)imidazole (6.92 mmol) in 20 ml of anhydrous THF. The mixture is then allowed to warm to 0° C. A solution of ethylene oxide (3 g; 0.068 mol; 10 equiv.) in 10 ml of anhydrous THF is added slowly at 0° C., and the mixture is stirred overnight at room temperature. The reaction mixture is poured into 50 ml of water and the THF is evacuated under reduced pressure. The product is extracted with CHCl$_3$ (3×150 ml), dried (Na$_2$SO$_4$) and concentrated in vacuo, leaving a brown oil. The latter is purified by means of a chromatography column (silica gel) using diethyl ether/ 40–60° C. petroleum ether (1:1) as eluent, giving the doubly protected hydroxyethyl compound (1.2 g; 52% yield).

A solution of 2-(tert-butyldimethylsilyl)-1-(dimethylsulphamoyl)-5-(2-hydroxyethyl)imidazole (0.7 g, 2.10 mmol), triphenylphosphine (0.82 g, 3.15 mmol) and 3-propanoylphenol (0.32 g, 2.10 mmol) in 20 ml of anhydrous THF is cooled and stirred under nitrogen at 0° C. A solution of diethyl azodicarboxylate (DEAD) (0.55 g, 3.15 mmol) in 10 ml of anhydrous THF is then added dropwise at 0° C., and the mixture is stirred at 0° C. for 10 minutes and then removed under reduced pressure and the resulting oil is purified on a chromatography column (silica gel) using an ethyl acetate/hexane (3:7) eluent to give 2-(tert-butyldimethylsilyl)-1-(dimethyl-sulphamoyl)-5-[3-(3-propanoylphenoxyethyl]imidazole.

The above compound (0.3 g; 6.72×10$^{-4}$) is heated at 80° C. with 2N HCl (12 ml) for 4 h. After cooling, the THF is removed under reduced pressure. The aqueous phase is washed with diethyl ether (3×100 ml), then alkalized with potassium carbonate and extracted (3×) with chloroform. The combined chloroform extracts are dried (MgSO$_4$) and then evaporated, giving an oil, which is dissolved in 2-propanol (2 ml) and treated with an excess of oxalic acid (1.5 equiv.) in 2-propanol (2 ml). The product is precipitated by adding diethyl ether, collected by filtration and washed with diethyl ether. Crystallization from ethanol gives pure 4-[2-(3-propanolphenoxy)ethyl]-1H-imidazole oxale. M.p.: 148–150° C.

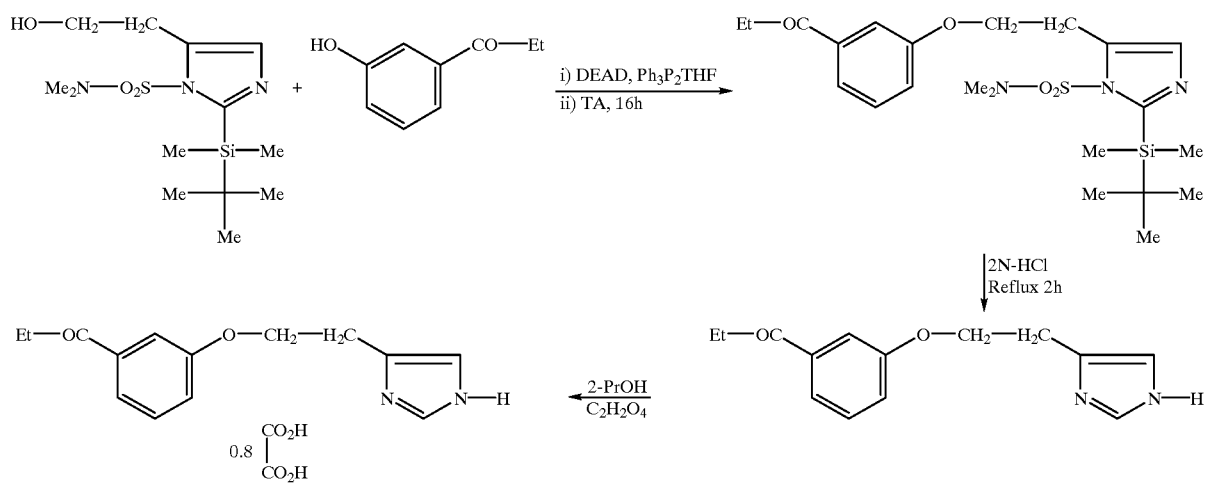

TA=RT
2N HCl [remove hyphen]

Method of Synthesis of Compounds having a Structural Component

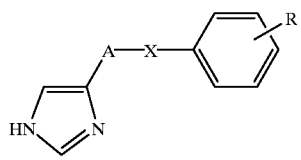

with A=—(CH$_2$)$_3$— and X=—NH—
Method G
4-[3-(3-Trifluoromethylphenylamino)propyl]-1H-imidazole oxalate A mixture of 1 g (2.72 mmol) of 1-(triphenylmethyl)-4-[3-hydroxypropyl]imidazole, 0.55 g (4.07 mmol; 1.5 equivalents) of morpholine oxide and 1.36 g of powdered 4 Å molecular sieve in an anhydrous mixture of acetonitrile and dichloromethane (10:4) is stirred at room temperature under nitrogen. 0.047 g (0.135 mmol; 5 mol %) of tetrapropylammonium perruthenate (VII) is added in a single portion and the mixture is stirred at room temperature for 48 hours. The reaction mixture is filtered through silica gel (preloaded with ethyl acetate) and the filtrate is evaporated under reduced pressure. The oil obtained is purified by chromatography on a column of silica gel with diethyl ether as eluent to yield 3-(1-triphenylmethyl-4-imidazolyl) propionaldehyde.

0.5 g (1.36 mmol) of the above aldehyde is heated with 0.22 g (1.36 mmol) of 3-trifluoromethylaniline in 50 ml of anhydrous toluene at 50° C. for 30 minutes. The solvent is driven off under reduced pressure to leave 0.6 g (86%) of an oil, which is dissolved in methanol, cooled to 0° C. and then treated with 1.06 g (0.027 mol; 20 equivalents) of sodium borohydride added slowly at 0° C. The mixture is stirred at room temperature overnight, the solvent is then driven off under reduced pressure, 20 ml of water are added and the mixture is extracted with chloroform. The chloroform extracts are dried (MgSO$_4$) and the solvent is evaporated off under reduced pressure to leave an oil, which is purified by chromatography on a column of silica gel (eluent: diethyl ether) to yield 0.4 g of 1-triphenylmethyl-4-[3-(3-trifluoromethylphenylamino)propyl]imidazole in the form of a colourless oil. The latter (0.35 g; 6.85 mmol) in 8 ml of tetrahydrofuran and 12 ml of 2M HCl is heated at 80° C. for 5 hours. The tetrahydrofuran is evaporated off under reduced pressure and Ph$_3$COH is extracted with diethyl ether. The aqueous layer is neutralized with potassium carbonate and the product is extracted into chloroform. The chloroform solution is dried and evaporated to yield a brown oil, which is purified by chromatography on a column of silica gel with an ethyl acetate/methanol (5:1) mixture as eluent. The oil obtained is dissolved in 4 ml of 2-propanol and treated with a solution of 1.5 equivalents of oxalic acid in 3 ml of 2-propanol, and the mixture is cooled for 4 hours. The precipitate which is formed on addition of diethyl ether is collected and washed with ether to yield the desired oxalate in the form of a white solid, m.p. 150–151° C.

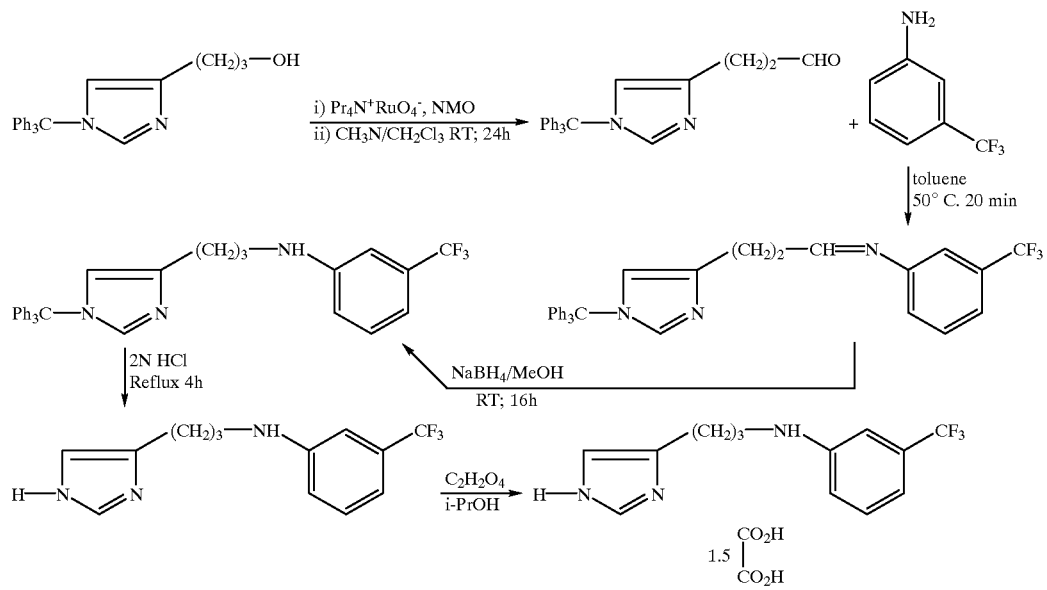

Method of Synthesis of Compounds having a Structural Component

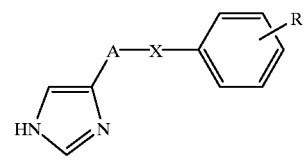

with A=—CH$_2$—CH(CH$_3$)— and X=—S—
Method H
4-[2-(3-Trifluoromethylphenylthio)propyl]-1H-imidazole oxalate 5.426 g (18.7 mmol) of 1-(N,N-dimethylsulphamoyl)-2-tert-butyldimothylsilylimidazole are dissolved in 100 ml of freshly distilled THF under nitrogen and cooled to −78° C., and a solution of n-butyl-lithium in hexane (2.5M; 15 ml; 37.5 mmol) is added dropwise over a period of 10 min. The mixture is stirred for 30 min at −78° C. The solution is warmed to 0° C. with rapid stirring, and a solution of 3.0 ml (2.49 g; 42.9 mmol) of propylene oxide in 20 ml of freshly distilled THF is added dropwise over a period of 15 min. The mixture is stirred for 18 hours with heating at 20° C., and the mixture is then hydrolysed by adding 100 ml of saturated NH$_4$Cl solution. The THF is removed under reduced pressure and the mixture obtained is extracted three times with 100 ml of dichloromethane. The organic layers are combined, dried (MgSO$_4$) and evaporated under reduced pressure to yield an oil, which is subjected to column chromatography with diethyl ether as eluent to yield 1-(N,N-dimethylsulphamoyl)-2-tert-butyldimethylsilyl-5-(2-hydroxypropyl)imidazole in the form of a viscous yellow oil.

The above oil (11.28 g; 32.5 mmol) is dissolved in 50 ml of anhydrous carbon tetrachloride, and 9.18 g (35.0 mmol) of anhydrous triphenylphosphine in 50 ml of anhydrous carbon tetrachloride are added. The mixture is stirred under a nitrogen atmosphere at 50° C. and then brought to reflux for 16 hours. The solvent is evaporated off in vacuo, and the solid obtained is subjected to column chromatography with dichloromethane on silica gel to yield 1-(N,N-dimethylsulphamoyl)-2-tert-butyldimethylsilyl-5-(2-chloropropyl)imidazole in the form of a pale yellow oil which solidifies, m.p. 51–53° C.

3-Trifluoromethylthiophenol (0.298 g; 1.67 mmol) is dissolved in 20 ml of anhydrous DMF and cooled to 0° C. under a nitrogen atmosphere, and NaH (60% dispersion in mineral oil; 0.0393 g; 1.638 mmol) is added in small portions. The reaction mixture is stirred at 0° C. for 15 min and then at 20° C. for a further 1.5 h, and 0.293 g (0.80 mmol) of 1-(N,N-dimethylsulphamoyl)-2-tert-butyldimethylsilyl-5-(2-chloropropyl) imidazole dissolved in 5 ml of DMF and 10 mg of n-Bu$_4$NI are added and the mixture is heated at 80° C. for 3 days. The solvent is driven off under reduced pressure to yield a brown oil, which is treated with 100 ml of water and extracted 3 times with 40 ml of dichloromethane. The extracts are dried (MgSO$_4$) and concentrated, and the oil obtained is subjected to column chromatography using 2:1 and 1:1 petroleum spirit/ethyl acetate, then dissolved in 10 ml of 2M HCl and heated at 100° C. under reflux for 3 hours. The reaction mixture is then alkalized by adding 10% NaOH (pH approximately 11) and is extracted 3 times with 40 ml of dichloromethane. The extracts are dried (MgSO$_4$) and evaporated to form a clear oil, which is subjected to column chromatography with ethyl acetate as eluent and converted to the oxalate of the desired product in 2-propanol, m.p. 166–168° C.

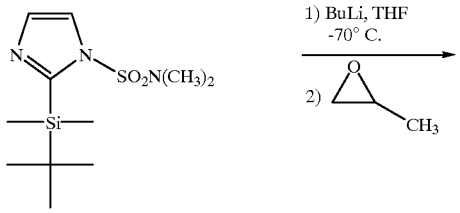

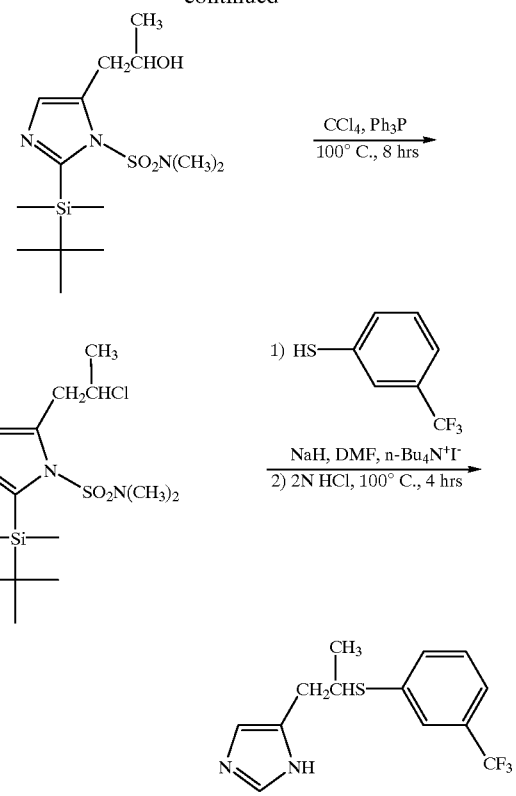

Synthesis of the Compounds 1 to 7 and 28 to 183 and Summary for the Compounds 8 to 27

Examples of Compounds According to the Present Invention

The compounds 1 to 20, 110, 111 and 154 to 159 are agonists or partial agonists.

The compounds 21–109, 112–153 and 160–182 are antagonists.

EXAMPLE 1

N-t-Butyl-3-(1H-imidazol-4-yl)propyl carbamate 5 mmol of 3-(1H-imidazol-4-yl)propanol.HCl and of 5 mmol t-butyl isocyanate in 10 ml of anhydrous acetonitrile are refluxed for 1 to 3 h. The solvent is evaporated off and the residue then purified by rotatory chromatography (eluent: chloroform/methanol (99:1–90:10), ammoniacal atmosphere). After removal of the solvent under reduced pressure, the residue is crystallized as hydrogen maleate from diethyl ether and ethanol.

| EF: $C_{11}H_{19}N_3O_2 \cdot C_4H_4O_4 \cdot 0.25H_2O$ (345.9) | | | | | | | |
|---|---|---|---|---|---|---|---|
| CHN analysis | Calculated | C | 52.1 | H | 6.85 | N | 12.2 |
|  | Found | C | 52.0 | H | 6.78 | N | 12.0 |
| Yield: 40% | | | | M.p.: 106–107.5° C. | | | |

EXAMPLE 2

3-(1H-Imidazol-4-yl)propyl-N-(diphenylmethyl) carbamate 5 mmol of 3-(1H-imidazol-4-yl)propanol.HCl and of 5 mmol of diphenylmethyl isocyanate are treated as described in Example 1.

EF: $C_{20}H_{21}N_3O_2 \cdot C_4H_4O_4 \cdot 0.25H_2O$ (456.0)
CHN analysis  Calculated  C  63.2  H  5.64  N  9.22
              Found       C  63.5  H  5.64  N  9.19
Yield: 85%                M.p.: 126–127° C.

EXAMPLE 3

3-(1H-Imidazol-4-yl)propyl-N-(2,2-diphenylethyl) carbamate 5 mmol of 3-(1H-imidazol-4-yl)propanol.HCl and of 5 mmol of 2,2-diphenylethyl isocyanate are treated as described in Example 1.

EF: $C_{21}H_{23}N_3O_2 \cdot C_4H_4O_4$ (465.5)
CHN analysis  Calculated  C  64.5  H  5.85  N  9.03
              Found       C  64.5  H  5.75  N  8.94
Yield: 60%                M.p.: 103–104° C.

EXAMPLE 4

2-(1H-Imidazol-4-yl)ethyl-N-(2,2-diphenylethyl) carbamate 5 mmol of 2-(1H-imidazol-4-yl)ethanol.HCl and of 5 mmol of 2,2-diphenylethyl isocyanate are treated as described in Example 1.

EF: $C_{20}H_{21}N_3O_2 \cdot C_4H_4O_4$ (451.5)
CHN analysis  Calculated  C  63.9  H  5.58  N  9.31
              Found       C  63.7  H  5.77  N  9.13
Yield: 40%                M.p.: 150–152° C.

EXAMPLE 5

3-(1H-Imidazol-4-yl)propyl 3-methylbutyl ether 5 mmol of sodium 3-(1-triphenylmethyl-1H-imidazol-4-yl)propanolate, 5 mmol of 3-methylbutane bromide and 0.5 mmol of 15-crown-15 (1, 4, 7, 10, 13-pentaoxacyclopentadecane) dissolved in 10 ml of anhydrous toluene are refluxed for 24 hours. The solvent is then evaporated off, and the residue dissolved in 10 ml THF and 30 ml 2N HCl and then heated at 70° C. for 2 hours. The THF is evaporated off under reduced pressure and triphenylmethanol is extracted with diethyl ether. The aqueous phase is neutralized with potassium carbonate and the product is extracted with diethyl ether. The organic extract is dried and evaporated, giving rise to an oil, which is crystallized as hydrogen maleate from diethyl ether and ethanol.

EF: $C_{11}H_{20}N_2O \cdot C_4H_4O_4$ (312.4)
CHN analysis  Calculated  C  57.7  H  7.74  N  8.97
              Found       C  57.5  H  7.66  N  8.89
Yield: 55%                M.p.: 74° C.

EXAMPLE 6

3-(1H-Imidazol-4-yl)propyl 3,3-dimethylbutyl ether 5 mmol of sodium 3-(1H-imidazol-4-yl)propanolate and 5 mmol of 3,3-dimethylbutane chloride are treated as described in Example 5.

EF: $C_{12}H_{22}N_2O \cdot C_4H_4O_4$ (326.4)
CHN analysis  Calculated  C  58.9  H  8.03  N  8.58
              Found       C  58.5  H  7.80  N  8.37
Yield: 60%                M.p.: 91° C.

EXAMPLE 7

3-(1H-Imidazol-4-yl)propyl 4-methylpentyl ether 5 mmol of sodium 3-(1H-imidazol-4-yl)propanolate and 5 mmol of 4-methylpentane chloride are treated as described in Example 5.

EF: $C_{12}H_{22}N_2O \cdot C_4H_4O_4$ (326.4)
CHN analysis  Calculated  C  58.9  H  8.03  N  8.58
              Found       C  58.8  H  7.77  N  8.41
Yield: 50%                M.p.: 86° C.

EXAMPLE 8

4-[3-(3-Trifluoramethylphenoxy)propyl]-1H-imidazole

The procedure is as described in synthesis route A.
Salt form: OXALATE
Crystallization solvent: from 2-PrOH by precipitation with $Et_2O$.

EF: $C_{13}H_{13}F_3N_2O \cdot C_2H_2O_4$
CHN analysis  Calculated  C  50.0  H  4.20  N  7.78
              Found       C  50.2  H  4.19  N  8.26
                          M.p.: 204–208° C.

EXAMPLE 9

4-[3-(3-Nitrophenoxy)propyl]-1H-imidazole

The procedure is as described in synthesis route A.
Salt form: OXALATE
Crystallization solvent: from 2-PrOH by precipitation with $Et_2O$.

EF: $C_{12}H_{13}N_3O_3 \cdot 0.9C_2H_2O_2$
CHN analysis  Calculated  C  50.4  H  4.54  N  12.8
              Found       C  50.4  H  4.43  N  12.6
                          M.p.: 189–191° C.

EXAMPLE 10

4-[2-(3-Trifluoromethylphenoxy)thioethyl]-1H-imidazole

The procedure is as described in synthesis route B.
Salt form: OXALATE
Crystallization solvent: from 2-PrOH by precipitation with $Et_2O$.

EF: $C_{12}H_{11}F_3N_2S \cdot 0.85\ C_2H_2O_4$
CHN analysis  Calculated  C  47.0  H  3.66  N  8.01
              Found       C  47.1  H  3.70  N  8.35
M.p.: 158–160° C.

EXAMPLE 11

4-[3-(3-Trifluoromethoxyphenoxy)propyl]-1H-imidazole

The procedure is as described in synthesis route A.
Salt form: OXALATE
Crystallization solvent: from 2-PrOH by precipitation with $Et_2O$.

EF: $C_{13}H_{13}F_3N_2 \cdot 0.9\ C_2H_2O_4$
CHN analysis  Calculated  C  48.4  H  4.06  N  7.63
              Found       C  48.5  H  4.15  N  7.64
M.p.: 177–179° C.

EXAMPLE 12

4-[3-(3-Isopropylphenoxy)propyl]-1H-imdazole

The procedure is as described in synthesis route A.
Salt form: OXALATE
Crystallization solvent: 2-PrOH.

EF: $C_{15}H_{20}N_2O \cdot 0.8\ C_2H_2O_4$
CHN analysis  Calculated  C  63.0  H  6.88  N  8.85
              Found       C  63.0  H  6.89  N  8.86
M.p.: 180–182° C.

EXAMPLE 13

4-[3-(3-tert-Butylphenoxy)propyl]-1H-imidazole

The procedure is as described in synthesis route A.
Salt form: OXALATE
Crystallization solvent: from 2-PrOH by precipitation with $Et_2O$.

EF: $C_{16}H_{22}N_2O \cdot 0.8\ C_2H_2O_4$
CHN analysis  Calculated  C  63.9  H  7.26  N  8.47
              Found       C  64.2  H  7.00  N  8.57
M.p.: 183–185° C.

EXAMPLE 14

4-[3-(3-Ethanoylphenoxy)propyl]-1H-imidazole

The procedure is as described in synthesis route A.
Salt form: OXALATE
Crystallization solvent: MeOH.

EF: $C_{14}H_{16}N_2O_2 \cdot 0.8\ C_2H_2O_4$
CHN analysis  Calculated  C  59.2  H  5.61  N  8.86
              Found       C  59.1  H  5.87  N  8.80
M.p.: 156–158° C.

EXAMPLE 15

4-[3-(3-Ethylphenoxy)propyl]-1H-imidazole

The procedure is as described in synthesis route A.
Salt form: OXALATE
Crystallization solvent: MeOH.

EF: $C_{14}H_{18}N_2O \cdot 0.85 C_2H_2O_4$
CHN analysis  Calculated  C  61.5  H  6.47  N  9.13
              Found       C  61.7  H  6.36  N  9.39
M.p.: 173–175° C.

EXAMPLE 16

4-[3-(3-Trifluoromethylphenoxy)butyl]-1H-imidazole

The procedure is as described in synthesis route C.
Salt form: OXALATE
Crystallization solvent: EtOH EF: $C_{14}H_{15}F_3N_2O \cdot 0.8\ C_2H_2O_4$
CHN analysis  Calculated  C  52.6  H  4.70  N  7.86
              Found       C  52.5  H  4.72  N  7.72
M.p.: 175–176° C.

EXAMPLE 17

4-[4-(3-Ethanoylphenoxy)butyl]-1H-imidazole

The procedure is as described in synthesis route C.
Salt form: OXALATE
Crystallization solvent: EtOH EF: $C_{15}H_{18}N_2O_2 \cdot 0.75\ C_2H_2O_4$
CHN analysis  Calculated  C  60.8  H  6.03  N  8.60
              Found       C  60.7  H  6.12  N  8.S9
M.p.: 168–170° C.

EXAMPLE 18

4-[3-(3-Propanoylphenoxy)propyl]-1H-imidazole

The procedure is as described in synthesis route A.
Salt form: OXALATE

Crystallization solvent: 2-PrOH

EF: $C_{15}H_{18}N_2O_2 \cdot 0.8\ C_2H_2O_4$
CHN analysis   Calculated   C   60.4   H   5.98   N   8.48
               Found        C   60.6   H   5.73   N   8.26
M.p.: 156–158° C.

EXAMPLE 19

4-[3-(3-(1-Hydroxypropyl)phenoxy)propyl]-1H-imidazole

The procedure is as described in synthesis route A.
Salt form: OXALATE
Crystallization solvent: 2-PrOH EF: $C_{15}H_{20}N_2O_2 \cdot 0.8\ C_2H_2O_4$
CHN analysis   Calculated   C   60.0   H   6.55   N   8.43
               Found        C   60.2   H   6.61   N   8.49
M.p.: 141–142° C.

EXAMPLE 20

4-[3-(3-Propylphenoxy)propyl]-1H-imidazole

The procedure is as described in synthesis route A.
Salt form: OXALATE
Crystallization solvent: 2-PrOH EF: $C_{15}H_{20}N_2O \cdot 1.1\ C_2H_2O_4$
CHN analysis   Calculated   C   60.3   H   6.03   N   9.20
               Found        C   60.6   H   6.15   N   9.35
M.p.: 166–168° C.

EXAMPLE 21

4-[3-(1,2,3,4-Tetrahydro-6-naphthyloxy)propyl]-1H-imidazole

The procedure is as described in synthesis route A.
Salt form: OXALATE
Crystallization solvent: MeOH EF: $C_{16}H_{20}N_2O \cdot 0.85\ C_2H_2O_4$
CHN analysis   Calculated   C   63.9   H   6.56   N   8.42
               Found        C   63.9   H   6.42   N   8.50
M.p.: 171–173° C.

EXAMPLE 22

4-[3-(5-Indanyloxy)propyl]-1H-imidazole

The procedure is as described in synthesis route A.
Salt form: OXALATE

Crystallization solvent: MeOH

EF: $C_{15}H_{18}N_2O \cdot 0.8\ C_2H_2O_4$
CHN analysis   Calculated   C   63.4   H   6.28   N   8.91
               Found        C   63.4   H   6.05   N   8.89
M.p.: 188–190° C.

EXAMPLE 23

4-[3-(3-N,N-Dimethylsulphonamidophenoxy)propyl]-1H-imidazole

The procedure is as described in synthesis route A.
Salt form: OXALATE
Crystallization solvent: EtOH EF: $C_{14}H_{19}N_3O_3S \cdot C_2H_2O_4$
CHN analysis   Calculated   C   48.1   H   5.30   N   10.5
               Found        C   48.3   H   4.94   N   10.4
M.p.: 142–144° C.

EXAMPLE 24

4-[3-(3-Hydroxyphenoxy)propyl]-1H-imidazole

The procedure is as described in synthesis route D.
Salt form: OXALATE
Crystallization solvent: 2-PrOH EF: $C_{12}H_{14}N_2O_2 \cdot C_2H_2O_4 \cdot 0.2\ H_2O$
CHN analysis   Calculated   C   53.9   H   5.30   N   8.98
               Found        C   54.0   H   5.31   N   8.78
M.p.: 138–140° C.

EXAMPLE 25

4-{3-[3-(2-Penten-3-yl)phenoxy]propyl}-1H-imidazole

The procedure is as described in synthesis route E.
Salt form: Ditrifluoroacetate
Crystallization solvent: 2-PrOH EF: $C_{17}H_{22}N_2O \cdot 2CF_3CO_2H$
CHN analysis   Calculated   C   50.6   H   4.85   N   5.62
               Found        C   50.5   H   4.82   N   5.40
M.p.: 169–171° C.

EXAMPLE 26

4-[3-(4-Cyanomethylphenoxy)propyl]-1H-imidazole

The procedure is as described in synthesis route A.
Salt form: base

Crystallization solvent:

EF: $C_{14}H_{15}N_3O.0.5\ H_2O$
CHN analysis  Calculated  C  67.2  H  6.44  N  16.8
                Found       C  67.4  H  6.44  N  16.5
M.p.: 125–127° C.

EXAMPLE 27

4-[3-(4-Phenoxyphenoxy)propyl]-1H-imidazole

The procedure is as described in synthesis route A.

Salt form: OXALATE
Crystallization solvent: EtOH

EF: $C_{18}H_{18}N_2O_2.0.9\ C_2H_2O_4$
CHN analysis  Calculated  C  63.4  H  5.32  N  7.46
                Found       C  63.6  H  5.35  N  7.48
M.p.: 186–188° C.

EXAMPLE 28

3-(1H-Imidazol-4-yl)propyl-N-propyl carbamate 5 mmol of 3-(1H-imidazol-4-yl)propanol.HCl and 5 mmol of propyl isocyanate are treated as described in Example 1.

EF: $C_{10}H_{17}N_3O_2.C_4H_4O_4$ (327.3)
CHN analysis  Calculated  C  51.4  H  6.47  N  12.8
                Found       C  51.4  H  6.55  N  12.7
Yield: 20%   M.p.: 97–99° C.

EXAMPLE 29

N-Butyl-3-(1H-imidazol-4-yl)propyl carbamate 5 mmol of 3-(1H-imidazol-4-yl)propanol.HCl and 5 mmol of butyl isocyanate are treated as described in Example 1.

EF: $C_{11}H_{19}N_3O_2.C_4H_4O_4$ (341.4)
CHN analysis  Calculated  C  52.8  H  6.79  N  12.3
                Found       C  52.9  H  6.78  N  12.2
Yield: 25%   M.p.: 95–96° C.

EXAMPLE 30

3-(1H-Imidazol-4-yl)propyl-N-pentyl carbamate 5 mmol of 3-(1H-imidazol-4-yl)propanol.HCl and 5 mmol of pentyl isocyanate are treated as described in Example 1.

EF: $C_{12}H_{21}N_3O_2.C_4H_4O_4.0.25\ H_2O$ (359.9)
CHN analysis  Calculated  C  53.4  H  7.14  N  11.7
                Found       C  53.7  H  7.24  N  12.0
Yield: 85%   M.p.: 91° C.

EXAMPLE 31

N-Hexyl-3-(1H-imidazol-4-yl)propyl carbamate 5 mmol of 3-(1H-imidazol-4-yl)propanol.HCl and 5 mmol of hexyl isocyanate are treated as described in Example 1.

EF: $C_{13}H_{23}N_3O_2.C_4H_4O_4.0.25\ H_2O$ (373.9)
CHN analysis  Calculated  C  54.6  H  7.41  N  11.2
                Found       C  54.4  H  7.70  N  11.0
Yield: 80%   M.p.: 86° C.

EXAMPLE 32

N-Heptyl-3-(1H-imidazol-4-yl)propyl carbamate 5 mmol of 3-(1H-imidazol-4-yl)propanol.HCl and 5 mmol of heptyl isocyanate are treated as described in Example 1.

EF: $C_{14}H_{25}N_3O_2.C_4H_4O_4.0.25\ H_2O$ (387.9)
CHN analysis  Calculated  C  55.7  H  7.66  N  10.8
                Found       C  56.0  H  7.68  N  10.8
Yield: 40%   M.p.: 103–104° C.

EXAMPLE 33

3-(1H-Imidazol-4-yl)propyl-N-octyl carbamate 5 mmol of 3-(1H-imidazol-4-yl)propanol.HCl and 5 mmol of octyl isocyanate are treated as described in Example 1.

EF: $C_{15}H_{27}N_3O_2.C_4H_4O_4.0.25\ H_2O$ (402.0)
CHN analysis  Calculated  C  56.8  H  7.90  N  10.5
                Found       C  56.8  H  7.93  N  10.5
Yield: 40%   M.p.: 103–104° C.

EXAMPLE 34

3-(1H-Imidazol-4-yl)propyl-N-(2-heptyl) carbamate 5 mmol of 3-(1H-imidazol-4-yl)propanol.HCl and 5 mmol of 2-heptyl isocyanate are treated as described in Example 1.

EF: $C_{14}H_{25}N_3O_2.C_4H_4O_4$ (383.4)
CHN analysis  Calculated  C  56.4  H  7.62  N  11.0
                Found       C  56.2  H  7.75  N  10.7
Yield: 65%   M.p.: 117–119° C.

EXAMPLE 35

3-(1H-Imidazol-4-yl)propyl-N-(2-octyl) carbamate 5 mmol of 3-(1H-imidazol-4-yl)propanol.HCl and 5 mmol of 2-octyl isocyanate are treated as described in Example 1.

| | | | | | | |
|---|---|---|---|---|---|---|
| EF: $C_{15}H_{27}N_3O_2 \cdot C_4H_4O_4$ (397.5) | | | | | | |
| CHN analysis | Calculated | C | 57.4 | H | 7.86 | N | 10.6 |
| | Found | C | 57.3 | H | 7.72 | N | 10.5 |
| Yield: 80% | | | M.p.: 118–119° C. | | | |

EXAMPLE 36

3-(1H-Imidazol-4-yl)propyl-N-(3-methylbutyl) carbamate 5 mmol of 3-(1H-imidazol-4-yl)propanol.HCl and 5 mmol of 3-methylbutyl isocyanate are treated as described in Example 1.

| | | | | | | |
|---|---|---|---|---|---|---|
| EF: $C_{12}H_{21}N_3O_2 \cdot C_4H_4O_4 \cdot 0.25 H_2O$ (359.9) | | | | | | |
| CHN analysis | Calculated | C | 53.4 | H | 7.14 | N | 11.7 |
| | Found | C | 53.7 | H | 7.17 | N | 11.8 |
| Yield: 30% | | | M.p.: 99–100° C. | | | |

EXAMPLE 37

3-(1H-Imidazol-4-yl)propyl-N-(2-methylbutyl) carbamate 5 mmol of 3-(1H-imidazol-4-yl)propanol.HCl and 5 mmol of 2-methylbutyl isocyanate are treated as described in Example 1.

| | | | | | | |
|---|---|---|---|---|---|---|
| EF: $C_{12}H_{21}N_3O_2 \cdot C_4H_4O_4 \cdot 0.25H_2O$ (359.9) | | | | | | |
| CHN analysis | Calculated | C | 53.4 | H | 7.14 | N | 11.7 |
| | Found | C | 53.5 | H | 7.08 | N | 11.4 |
| Yield: 55% | | | M.p.: 98–100.5° C. | | | |

EXAMPLE 38

3-(1H-Imidazol-4-yl)propyl-N-(2-pentyl) carbamate 5 mmol of 3-(1H-imidazol-4-yl)propanol.HCl and 5 mmol of 2-pentyl isocyanate are treated as described in Example 1.

| | | | | | | |
|---|---|---|---|---|---|---|
| EF: $C_{12}H_{21}N_3O_2 \cdot C_4H_4O_4 \cdot 0.25H_2O$ (359.9) | | | | | | |
| CHN analysis | Calculated | C | 53.4 | H | 7.14 | N | 11.7 |
| | Found | C | 53.7 | H | 7.09 | N | 11.6 |
| Yield: 35% | | | M.p.: 114–116° C. | | | |

EXAMPLE 39

3-(1H-Imidazol-4-yl)propyl-N,N-dipropyl carbamate 5 mmol of 3-(1H-imidazol-4-yl)propanol.HCl and 5 mmol of N,N-dipropylcarbamoyl chloride are treated as described in Example 1 and crystallized as hydrogen oxalate from diethyl ether and ethanol.

| | | | | | | |
|---|---|---|---|---|---|---|
| EF: $C_{13}H_{23}N_3O_2 \cdot C_2H_2O_4$ (343.4) | | | | | | |
| CHN analysis | Calculated | C | 52.5 | H | 7.34 | N | 12.2 |
| | Found | C | 52.4 | H | 7.33 | N | 12.2 |
| Yield: 35% | | | M.p.: 145–147° C. | | | |

EXAMPLE 40

N,N-Diallyl-3-(1H-imidazol-4-yl)propyl carbamate 5 mmol of 3-(1H-imidazol-4-yl)propanol.HCl and 5 mmol of N,N-diallylcarbamoyl chloride are treated as described in Example 1.

| | | | | | | |
|---|---|---|---|---|---|---|
| EF: $C_{31}H_{19}N_3O_2 \cdot C_4H_4O_4 \cdot 0.25H_2O$ (369.9) | | | | | | |
| CHN analysis | Calculated | C | 55.2 | H | 6.40 | N | 11.4 |
| | Found | C | 55.2 | H | 6.13 | N | 11.6 |
| Yield: 20% | | | M.p.: 56–57° C. | | | |

EXAMPLE 41

N-(3-(1H-Imidazol-4-yl)propyloxycarbonyl) piperidine 5 mmol of 3-(1H-imidazol-4-yl)propanol.HCl and 5 mmol of piperidinecarbamoyl chloride are treated as described in Example 1.

| | | | | | | |
|---|---|---|---|---|---|---|
| EF: $C_{12}H_{19}N_3O_2 \cdot C_4H_4O_4 \cdot 0.25H_2O$ (357.9) | | | | | | |
| CHN analysis | Calculated | C | 53.7 | H | 6.62 | N | 11.7 |
| | Found | C | 54.0 | H | 6.61 | N | 11.7 |
| Yield: 70% | | | M.p.: 97–99° C. | | | |

EXAMPLE 42

3-(1H-Imidazol-4-yl)propyl-N-trans-(2-phenylcyclopropyl) carbamate 5 mmol of 3-(1H-imidazol-4-yl)propanol.HCl and 5 mmol of trans-2-phenylcyclopropyl isocyanate are treated as described in Example 1.

| | | | | | | |
|---|---|---|---|---|---|---|
| EF: $C_{16}H_{19}N_3O_2 \cdot C_4H_4O_4 \cdot 0.25H_2O$ (405.9) | | | | | | |
| CHN analysis | Calculated | C | 59.2 | H | 5.84 | N | 10.4 |
| | Found | C | 59.4 | H | 5.96 | N | 10.2 |
| Yield: 45% | | | M.p.: 107–109° C. | | | |

EXAMPLE 43

N-(4-Fluorophenylmethyl)-2-(1H-imidazol-4-yl) ethyl carbamate 5 mmol of 3-(1H-imidazol-4-yl)ethanol.HCl and 5 mmol of 4-fluorophenylmethyl isocyanate are treated as described in Example 1.

EF: C₁₃H₁₄N₃O₂F.C₄H₄O₄ (379.3)
CHN analysis   Calculated   C   53.8   H   4.78   N   11.1
               Found        C   53.8   H   4.80   N   11.0
Yield: 60%                  M.p.: 139° C.

EXAMPLE 44

3-(1H-Imidazol-4-yl)propyl N-(2-phenylpropyl) carbamate 5 mmol of 3-(1H-imidazol-4-yl)propanol.HCl and 5 mmol of 2-phenylpropyl isocyanate (freshly prepared from 2-phenylpropylamine and diphosgene in ethyl acetate (Japan Kokai Tokkyo Koho JP, 60, 162, 262 (05.07.1985): Chem. Abstr. 103, 215012) are treated as described in Example 1.

EF: C₁₆H₂₁N₃O₂.C₄H₄O₄.0.25H₂O (407.9)
CHN analysis   Calculated   C   58.9   H   6.30   N   10.3
               Found        C   58.6   H   6.14   N   10.3
Yield: 40%                  M.p.: 90° C.

EXAMPLE 45

N-(3-(Trifluoromethyl)phenylmethyl)-3-(1H-imidazol-4-yl)propyl carbamate 5 mmol of 3-(1H-imidazol-4-yl)propanol.HCl and 5 mmol of 3-(trifluoromethyl)phenylmethyl isocyanate are treated as described in Example 1.

EF: C₁₅H₁₆N₃O₂F₃.C₄H₄O₄ (443.4)
CHN analysis   Calculated   C   51.5   H   4.55   N   9.48
               Found        C   51.6   H   4.46   N   9.36
Yield: 20%                  M.p.: 97–98° C.

EXAMPLE 46

N-Fluoren-9-yl-3-(1H-imidazol-4-yl)propyl carbamate 5 mmol of 3-(1H-imidazol-4-yl)propanol.HCl and 5 mmol of 9-fluorenyl isocyanate are treated as described in Example 1.

EF: C₂₀H₁₉N₃O₂.C₄H₄O₄.0.25H₂O (454.0)
CHN analysis   Calculated   C   63.5   H   5.22   N   9.26
               Found        C   63.6   H   5.23   N   9.38
Yield: 50%                  M.p.: 174–175° C.

EXAMPLE 47

N-(4-(Trifluoromethoxy)phenyl)-3-(1H-imidazol-4-yl)propyl carbamate 5 mmol of 3-(1H-imidazol-4-yl)propanol.HCl and 5 mmol of 4-(trifluoromethoxy)phenyl isocyanate are treated as described in Example 1.

EF: C₁₄H₁₄N₃O₃F₃ · C₄H₄O₄ · 0 · 25H₂O (449.9)
CHN analysis   Calculated   C   48.1   H   4.14   N   9.34
               Found        C   48.3   H   4.19   N   9.32
Yield: 95%                  M.p.: 119–121° C.

EXAMPLE 48

3-(1H-Imidazol-4-yl)propyl-N-(2-thenyl) carbamate 5 mmol of 3-(1H-imidazol-4-yl)propanol.HCl and 5 mmol of 2-thenyl isocyanate are treated as described in Example 1.

EF: C₁₂H₁₅N₃O₂S · C₄H₄O₄ · 0 · 25H₂O (385.9)
CHN analysis   Calculated   C   49.8   H   5.04   N   10.9
               Found        C   50.2   H   5.09   N   10.9
Yield: 80%                  M.p.: 103–105° C.

EXAMPLE 49

3-(1H-Imidazol-4-yl)propyl-N-phenyl thioncarbamate 5 mmol of sodium 3-(1H-imidazol-4-yl)propanolate and 5 mmol of phenyl thiocyanate are treated as described in Example 1.

EF: C₁₃H₁₅N₃OS · C₄H₄O₄ (377.4)
CHN analysis   Calculated   C   54.1   H   5.07   N   11.1
               Found        C   53.7   H   5.12   N   11.1
Yield: 55%                  M.p.: 129–131° C.

EXAMPLE 50

3-(1H-Imidazol-4-yl)-1-(4-methylphenyl)propanone 5 mmol of 3-(1-triphenylmethyl-1H-imidazol-4-yl) propanoic acid methyl ester are dissolved at 0° C. in 10 ml of thionyl chloride. After 1 hour of stirring at room temperature, the solvent is evacuated under reduced pressure. The residue is dissolved in toluene and added to a solution of 15 mmol of AlCl₃ in 20 ml of toluene. After 30 minutes at 0° C., the reaction is refluxed for 5 hours. The toluene is evaporated off and the residue is hydrolysed with water. Extraction with diethyl ether followed by concentration gives an oil, which is heated in 30 ml 2N HCl and 10 ml of THF.

The THF is evaporated off under reduced pressure and triphenylmethanol is extracted with diethyl ether. The aqueous phase is alkalized using ammonia, and the crude product is extracted with diethyl ether and purified by rotatory chromatography (eluent: chloroform/methanol (99:1–90:10), ammoniacal atmosphere). After evacuation of the solvent under reduced pressure, the product is recrystallized as hydrogen maleate from diethyl ether and ethanol.

EF: $C_{13}H_{14}N_2 \cdot C_4H_4O_4$ (330.4)
CHN analysis   Calculated   C   61.8   H   5.49   N   8.48
               Found        C   61.8   H   5.52   N   8.50
Yield: 35%                       M.p.: 121° C.

EXAMPLE 51

3-(1H-Imidazol-4-yl)-4-phenyl-1-butene 10 mmol of 3-phenylpropyltriphenylphosphonium bromide, 10 mmol of (1-triphenylmethyl-1H-imidazol-4-yl)methanal (J. L. Kelley, C. A. Miller, E. W. Mc Lean, J. Med. Chem. 1977, 20, 721) and 12 mmol of potassium of t-butanolate are stirred for 24 hours in 50 ml THF. The solvent is evaporated off under reduced pressure, hydrolysed with water and extracted using chloroform. The concentrated organic extract is heated from reflux in 30 ml 2N HCl and 30 ml of acetone for 1 hour. The solvent is evaporated off under reduced pressure and triphenylmethanol is extracted using diethyl ether. The aqueous phase is alkalized using ammonia and the crude product is extracted using diethyl ether. The aqueous phase is alkalized using diethyl ether and crystallized as hydrogen maleate from diethyl ether and ethanol.

EF: $C_{13}H_{14}N_2 \cdot C_4H_4O_4$ (314.3)
CHN analysis   Calculated   C   65.0   H   5.77   N   8.91
               Found        C   65.0   H   5.74   N   8.81
Yield: 40%                       M.p.: 114° C.

EXAMPLE 52

3-(1H-Imidazol-4-yl)-4-pheylbutane 3 mmol of (1H-imidazol-4-yl)-4-phenyl-1-butene (Example 51) are dissolved in 50 ml of methanol. 70 mg Pd/C (10%) are added, and reduction is carried out for 12 hours at a pressure of 10 bar under hydrogen.

The solution is filtered and purified by rotatory chromatography. The product is crystallized as hydrogen maleate from diethyl ether and ethanol.

EF: $C_{13}H_{16}N_2 \cdot C_4H_4O_4$ (316.4)
CHN analysis   Calculated   C   64.5   H   6.37   N   8.86
               Found        C   64.7   H   6.36   N   8.73
Yield: 95%                       M.p.: 128–129° C.

EXAMPLE 53

Cyclohexylmethyl (1H-imidazol-4-yl)methyl ether 5 mmol of sodium (1-triphenylmethyl-1H-imidazol-4-yl)-methanolate and 5 mmol of cyclohexylmethane chloride are treated as described in Example 5.

EF: $C_{11}H_{18}N_2O \cdot C_4H_4O_4 \cdot 0 \cdot 5H_2O$ (319.4)
CHN analysis   Calculated   C   56.4   H   7.26   N   8.77
               Found        C   56.3   H   7.19   N   8.94
Yield: 40%                       M.p.: 104° C.

EXAMPLE 54

(Bicyclo[2.2.1]hept-2-yl)methyl (1H-imidazol-4-yl) methyl ether 5 mmol of sodium (1-triphenylmethyl-1H-imidazol-4-yl)-methanolate and 5 mmol of (bicyclo[2.2.1]hept-2-yl)-methane chloride are treated as described in Example 5.

EF: $C_{12}H_{18}N_2O \cdot C_4H_4O_4$ (322.4)
CHN analysis   Calculated   C   59.6   H   6.88   N   8.69
               Found        C   59.2   H   6.86   N   8.66
Yield: 50%                       M.p.: 114° C.

EXAMPLE 55

3-(1H-Imidazol-4-yl)propyl 3-(4-methylphenyl) propyl ether 5 mmol of sodium 3-(1-triphenylmethyl-1H-imidazol-4-yl)propanolate and 5 mmol of 3-(4-methylphenyl)propane chloride are treated as described in Example 5.

EF: $C_{16}H_{22}N_2O \cdot C_4H_4O_4$ (374.4)
CHN analysis   Calculated   C   64.2   H   7.00   N   7.48
               Found        C   64.0   H   7.25   N   7.70
Yield: 20%                       M.p.: 125–126° C.

EXAMPLE 56

3-(1H-Imidazol-4-yl)propyl 2-naphthylmethyl ether 5 mmol of sodium 3-(1-triphenylmethyl-1H-imidazol-4-yl)propanolate and 5 mmol of 2-naphthylmethane chloride are treated as described in Example 5.

EF: $C_{17}H_{18}N_2O \cdot C_4H_4O_4$ (382.4)
CHN analysis   Calculated   C   66.0   H   5.80   N   7.33
               Found        C   65.8   H   5.76   N   7.06
Yield: 40%                       M.p.: 93° C.

EXAMPLE 57

3-(1H-Imidazol-4-yl)propyl (4-biphenyl)methyl ether 5 mmol of sodium 3-(1-triphenylmethyl-1H-imidazol-4-yl)propanolate and 5 mmol of 4-biphenylmethane chloride are treated as described in Example 5.

EF: $C_{19}H_{20}N_2O \cdot C_4H_4O_4 \cdot 0 \cdot 5H_2O$ (417.5)
CHN analysis   Calculated   C   66.2   H   6.04   N   6.71
               Found        C   66.0   H   5.88   N   6.74
Yield: 30%                       M.p.: 122° C.

EXAMPLE 58

3-(4-Trifluoromethyl)phenyl)propyl-3-(1H-imidazol-4-yl)propyl ether 5 mmol of sodium 3-(1-triphenylmethyl-1H-imidazol-4-yl)propanolate and 5 mmol of 3-(4—trifluoromethyl)phenylpropane chloride are treated as described in Example 5.

EF: $C_{16}H_{19}N_2OF_3 \cdot C_4H_4O_4$ (428.4)
CHN analysis  Calculated  C  56.1  H  5.41  N  6.54
              Found       C  56.2  H  5.62  N  6.61
Yield: 35%                M.p.: 104° C.

EXAMPLE 59

3-(1H-Imidazol-4-yl)propyl-2-quoinlylmethyl ether 5 mmol of sodium 3-(1-triphenylmethyl-1H-imidazol-4-yl)propanolate and 5 mmol of 2-quinolylmethane chloride are treated as described in Example 5.

EF: $C_{16}H_{17}N_3O \cdot C_4H_4O_4$ (383.4)
CHN analysis  Calculated  C  62.7  H  5.52  N  11.0
              Found       C  62.4  H  5.71  N  10.7
Yield: 35%                M.p.: 97° C.

EXAMPLE 60

3-(2,4-Dichloropheuyl)propyl-3-(1H-imidazol-4-yl)propyl ether 5 mmol of sodium 3-(1-triphenylmethyl-1H-imidazol-4-yl)propanolate and 5 mmol of 3-(2,4-dichlorophenyl)propane chloride are treated as described in Example 5.

EF: $C_{15}H_{18}N_2OCl_2 \cdot C_4H_4O_4$ (429.3)
CHN analysis  Calculated  C  53.2  H  5.17  N  6.53
              Found       C  53.2  H  5.33  N  6.23
Yield: 30%                M.p.: 119–120° C.

EXAMPLE 61

2-(Bicyclo[2.2.1]hept-2-yl)ethyl 3-(1H-imidazol-4-yl)propyl ether 5 mmol of sodium 3-(1-triphenylmethyl-1H-imidazol-4-yl)propanolate and 5 mmol of 2-(bicyclo[2.2.1]hept-2-yl)ethane chloride are treated as described in Example 5.

EF: $C_{15}H_{24}N_2O \cdot C_4H_4O_4 \cdot 0 \cdot 25H_2O$ (368.9)
CHN analysis  Calculated  C  61.9  H  7.79  N  7.59
              Found       C  61.6  H  7.72  N  7.72
Yield: 55%                M.p.: 94° C.

EXAMPLE 62

3-(1H-Imidazol-4-yl)propyl 3-(4-methoxyphenyl)propyl ether 5 mmol of sodium 3-(1-triphenylmethyl-1H-imidazol-4-yl)propanolate and 5 mmol of 3-(4-methoxyphenyl)propane chloride are treated as described in Example 5.

EF: $C_{16}H_{22}N_2O_2 \cdot C_4H_4O_4 \cdot 0 \cdot 25H_2O$ (394.9)
CHN analysis  Calculated  C  60.8  H  6.76  N  7.09
              Found       C  60.6  H  6.69  N  7.09
Yield: 50%                M.p.: 116° C.

EXAMPLE 63

3-(1H-Imidazol-4-yl)propyl 2-phenylethyl ether 5 mmol of 3-(1-triphenylmethyl-1H-imidazol-4-yl)propane chloride, prepared from 3-(1-triphenylmethyl-1H-imidazol-4-yl)propanol with thionyl chloride, and 15 mmol of sodium 2-phenylethanolate are treated as described in Example 5.

EF: $C_{14}H_{18}N_2O \cdot C_4H_4O_4$ (346.4)
CHN analysis  Calculated  C  62.4  H  6.40  N  8.09
              Found       C  62.2  H  6.47  N  8.06
Yield: 15%                M.p.: 89–91° C.

EXAMPLE 64

3-(1H-Imidazol-4-yl)propyl heptyl ether 5 mmol of sodium 3-(1-triphenylmethyl-1H-imidazol-4-yl)propanolate and 5 mmol of heptane chloride are treated as described in Example 5.

EF: $C_{13}H_{24}N_2O \cdot C_4H_4O_4$ (340.4)
CHN analysis  Calculated  C  60.0  H  8.29  N  8.23
              Found       C  59.6  H  8.23  N  8.18
Yield: 55%                M.p.: 88° C.

EXAMPLE 65

3-(1H-Imidazol-4-yl)propyl 2-methylpropyl ether 5 mmol of sodium 3-(1-triphenylmethyl-1H-imidazol-4-yl)propanolate and 5 mmol of 2-methylpropane chloride are treated as described in Example 5.

EF: $C_{10}H_{18}N_2O \cdot C_4H_4O_4$ (298.3)
CHN analysis  Calculated  C  56.4  H  7.43  N  9.39
              Found       C  56.6  H  7.23  N  9.21
Yield: 30%                M.p.: 82° C.

EXAMPLE 66

2-Cyclohexylethyl 3-(1H-imidazol-4-yl)propyl ether 5 mmol of 3-(1-triphenylmethyl-1H-imidazol-4-yl)propane chloride (see Example 63) and 15 mmol of sodium 2-cyclo-hexylethanolate are treated as described in Example 5.

EF: $C_{14}H_{24}N_2O \cdot C_4H_4O_4$ (352.4)
CHN analysis  Calculated  C  61.4  H  8.01  N  7.95
              Found       C  61.2  H  8.05  N  7.95
Yield: 45%                          M.p.: 96° C.

EXAMPLE 67

3-(1H-Imidazol-4-yl)propyl 4-pentinyl ether 5 mmol of sodium 3-(1-triphenylmethyl-1H-imidazol-4-yl)propanolate and 5 mmol of 4-pentine chloride are treated as described in Example 5.

EF: $C_{11}H_{16}N_2O \cdot C_4H_4O_4 \cdot 0 \cdot 5H_2O$ (317.3)
CHN analysis  Calculated  C  56.8  H  6.67  N  8.83
              Found       C  56.9  H  6.42  N  8.77
Yield: 40%                          M.p.: 74° C.

EXAMPLE 68

3-(1H-Imidazol-4-yl)propyl 2-(phenoxy)ethyl ether 5 mmol of sodium 3-(1-triphenylmethyl-1H-imidazol-4-yl)propanolate and 5 mmol of 2-phenoxyethane chloride are treated as described in Example 5.

EF: $C_{14}H_{18}N_2O_2 \cdot C_4H_4O_4 \cdot 0 \cdot 25H_2O$ (366.9)
CHN analysis  Calculated  C  58.9  H  6.18  N  7.64
              Found       C  58.7  H  6.15  N  7.64
Yield: 40%                          M.p.: 96° C.

EXAMPLE 69

3-(1H-Imidazol-4-yl)propyl 4-(methylthio)phenylmethyl ether 5 mmol of sodium 3-(1-triphenylmethyl-1H-imidazol-4-yl)propanolate and 5 mmol of 4-(methylthio)phenylmethane chloride are treated aa described in Example 5.

EF: $C_{14}H_{18}N_2OS \cdot C_4H_4O_4$ (378.5)
CHN analysis  Calculated  C  57.1  H  5.86  N  7.40
              Found       C  57.2  H  5.84  N  7.25
Yield: 50%                          M.p.: 108° C.

EXAMPLE 70

3-(4-Fluorophenyl)propyl 3-(1H-imidazol-4-yl)-2-propenyl ether 5 mmol of sodium 3-(1-triphenylmethyl-1H-imidazol-4-yl)-2-propenolate and of 3-(4-fluorophenyl)propane chloride are treated as described in Example 5.

EF: $C_{15}H_{17}N_2OF \cdot C_4H_4O_4$ (376.4)
CHN analysis  Calculated  C  60.6  H  5.62  N  7.44

-continued

Found       C  60.4  H  5.55  N  7.69
Yield: 20%                          M.p.: 130–132° C.

EXAMPLE 71

3-(1H-Imidazol-4-yl)propyl diphenylmethyl ether 5 mmol of 3-(1H-imidazol-4-yl)propanol.HCl and 5 mmol of diphenylmethane chloride in 50 ml of acetonitrile are refluxed for 4–5 hours, the solvent is evaporated off and the residue purified by rotatory chromatography (eluent: chloroform/methanol (90–99:10–1), ammoniacal atmosphere). After evacuation of the solvent under reduced pressure the residue is crystallized as hydrogen maleate from diethyl ether and ethanol.

EF: $C_{19}H_{20}N_2O \cdot C_4H_4O_4$ (408.5)
CHN analysis  Calculated  C  67.6  H  5.92  N  6.85
              Found       C  67.4  H  5.92  N  6.86
Yield: 55%                          M.p.: 105–107° C.

EXAMPLE 72

(4-Fluorophenyl)phenylmethyl 3-(1H-imidazol-4-yl)propyl ether 5 mmol of 3-(1H-imidazol-4-yl)propanol.HCl and 5 mmol of (4-fluorophenyl)phenylmethane chloride are treated as described in Example 71.

EF: $C_{19}H_{19}N_2OF \cdot C_4H_4O_4$ (426.4)
CHN analysis  Calculated  C  64.8  H  5.44  N  6.57
              Found       C  64.7  H  5.34  N  6.76
Yield: 65%                          M.p.: 90° C.

EXAMPLE 73

Bis(4-fluorophenyl)methyl 3-(1H-imidazol-4-yl)propyl ether 5 mmol of 3-(1H-imidazol-4-yl)propanol.HCl and 5 mmol of bis(4-fluorophenyl)methane chloride are treated as described in Example 71.

EF: $C_{19}H_{18}N_2OF_2 \cdot C_4H_4O_4$ (444.4)
CHN analysis  Calculated  C  62.2  H  4.98  N  6.30
              Found       C  61.9  H  4.98  N  6.29
Yield: 40%                          M.p.: 107–109° C.

EXAMPLE 74

2-(3-(1H-Imidazol-4-yl)propyloxy)-1-phenylethanone 5 mmol of 3-(1-triphenylmethyl-1H-imidazol-4-yl)propanol and 5 mmol of 2-bromo-1-phenylethanone are stirred for 72 hours in methylene chloride. The solvent is evaporated off under reduced pressure and the residue is refluxed for 1 hour in 30 ml of 2N HCl and 30 ml of acetone.

The solvent is evaporated off under reduced pressure and triphenylmethanol is extracted using diethyl ether. The aqueous phase is alkalized with ammonia, and the crude product is extracted with diethyl ether, purified by rotatory chromatography and crystallized as hydrogen maleate from diethyl ether and ethanol.

EF: $C_{14}H_{16}N_2O_2 \cdot C_4H_4O_4$ (360.4)
CHN analysis  Calculated  C  60.0  H  5.59  N  7.77
              Found       C  60.0  H  5.73  N  7.77
Yield: 80%                      M.p.: 85–86° C.

EXAMPLE 75

2-(3-(1H-Imidazol-4-yl)propyloxy)-1-(3-nitrophenyl)ethanone 5 mmol of 3-(1-triphenylmethyl-1H-imidazol-4-yl)propanol and 5 mmol of 2-bromo-1-(3-nitrophenyl)ethanone are treated as described in Example 74.

EF: $C_{14}H_{15}N_3O_4 \cdot C_4H_4O_4 \cdot H_2O$ (423.4)
CHN analysis  Calculated  C  51.1  H  5.00  N  9.92
              Found       C  51.4  H  4.73  N  10.1
Yield: 35%                      M.p.: 117–118° C.

EXAMPLE 76

4-(4-(3-(1H-Imidazol-4-yl)propyloxy)phenyl)-2-butanone 5 mmol of 3-(1-triphenylmethyl-1H-imidazol-4-yl)propanol, 6 mmol of triphenylphosphine and 5 mmol of 4-(4-hydroxyphenyl)-2-butanone are dissolved under nitrogen in the cold. 6 mmol of diethyl azodicarboxylate, dissolved in 4 ml of THF, are added and the reaction mixture is stirred at room temperature for 48 hours. After evacuation of the solvent under reduced pressure and column chromatography (eluent: ethyl acetate), the residue is dissolved in 10 ml THF and 30 ml of 2N HCl and heated to 70° C. for 2 hours. The solvent is evaporated off under reduced pressure and triphenylmethanol is extracted using diethyl ether. The aqueous phase is neutralized with potassium carbonate and the product extracted with diethyl ether. The ethereal solution is dried and evaporated to obtain an oil, which is crystallized as hydrogen maleate from diethyl ether and ethanol.

EF: $C_{16}H_{20}N_2O_2 \cdot C_4H_4O_4 \cdot 0 \cdot 5H_2O$ (397.4)
CHN analysis  Calculated  C  60.4  H  6.34  N  7.05
              Found       C  60.5  H  6.28  N  7.43
Yield: 75%                      M.p.: 104° C.

EXAMPLE 77

(4-(3-(1H-Imidazol-4-yl)propyloxy)phenyl)carbaldehyde 5 mmol of 3-(1-triphenylmethyl-1H-imidazol-4-yl)propanol and 6 mmol of 4-hydroxyphenylcarbaldehyde are treated as described in Example 76.

EF: $C_{13}H_{14}N_2O_2 \cdot C_4H_4O_4$ (346.3)
CHN analysis  Calculated  C  59.0  H  5.24  N  8.08
              Found       C  58.9  H  5.51  N  8.24
Yield: 85%                      M.p.: 120° C.

EXAMPLE 78

(4-(3-(1H-Imidazol-4-yl)propyloxy)phenyl)ethanone 5 mmol of 3-(1-triphenylmethyl-1H-imidazol-4-yl)propanol and 6 mmol of (4-hydroxyphenyl)ethanone are treated as described in Example 76.

EF: $C_{14}H_{16}N_2O_2 \cdot C_4H_4O_4$ (360.4)
CHN analysis  Calculated  C  60.0  H  5.59  N  7.77
              Found       C  59.8  H  5.86  N  7.56
Yield: 80%                      M.p.: 118° C.

EXAMPLE 79

(4-(3-(1H-Imidazol-4-yl)propyloxy)phenyl)propanone 5 mmol of 3-(1-triphenylmethyl-1H-imidazol-4-yl)propanol and 6 mmol of 4-hydroxyphenylpropanone are treated as described in Example 76.

EF: $C_{15}H_{18}N_2O_2 \cdot C_4H_4O_4$ (374.4)
CHN analysis  Calculated  C  61.0  H  5.92  N  7.46
              Found       C  61.0  H  5.88  N  7.42
Yield: 80%                      M.p.: 136° C.

EXAMPLE 80

(4-(3-(1H-Imidazol-4-yl)propyloxy)phenyl)-2-methylpropanone 5 mmol of 3-(1-triphenylmethyl-1H-imidazol-4-yl)propanol and 6 mmol of (4-hydroxyphenyl)-2-methylpropanone are treated as described in Example 76.

EF: $C_{16}H_{20}N_2O_2 \cdot C_4H_4O_4 \cdot 0 \cdot 5H_2O$ (397.4)
CHN analysis  Calculated  C  60.4  H  6.34  N  7.05
              Found       C  60.5  H  6.03  N  7.03
Yield: 85%                      M.p.: 95° C.

EXAMPLE 81

Cyclopropyl 4-(3-(1H-imidazol-4-yl)propyloxy)phenyl ketone

Method 1:
5 mmol of sodium 3-(1-triphenylmethyl-1H-imidazol-4-yl)propanolate, 10 mmol of 4-chloro-4'-fluorobutyrophenone and 30 mmol of NaH (60% suspension in mineral oil) are heated for 48 h in toluene under reflux. The reaction mixture is treated as described in Example 5. Yield: 40%.

Method 2:
5 mmol of 3-(1-triphenylmethyl-1H-imidazol-4-yl)propanol and 6 mmol of cyclopropyl 4-hydroxyphenyl ketone are treated as described in Example 76. Yield 80%.

Method 3:

5 mmol of sodium 3-(1-triphenylmethyl-1H-imidazol-4-yl)propanolate, 10 mmol of cyclopropyl 4-fluorophenyl ketone and 10 mmol of NaH (60% suspension in mineral oil) are heated for 4 hours in toluene under reflux. The reaction mixture is then treated as described in Example 5. Yield 40%.

EF: $C_{16}H_{18}N_2O_2 \cdot C_4H_4O_4$ (386.4)
CHN analysis  Calculated  C  62.2  H  5.74  N  7.25
              Found       C  62.5  H  5.81  N  7.20
              M.p.: 118–125° C.

EXAMPLE 82

Cyclobutyl 4-(3-(1H-imidazol-4-yl)propyloxy) phenyl ketone 5 mmol of 3-(1-triphenylmethyl-1H-imidazol-4-yl) propanol and 6 mmol of cyclobutyl 4-hydroxyphenyl ketone are treated as described in Example 76.

EF: $C_{17}H_{20}N_2O_2 \cdot C_4H_4O_4 \cdot 0 \cdot 25H_2O$ (404.9)
CHN analysis  Calculated  C  62.3  H  6.10  N  6.92
              Found       C  62.0  H  6.02  N  7.18
Yield: 80%                M.p.: 130° C.

EXAMPLE 83

Cyclopentyl 4-(3-(1H-imidazol-4-yl)propyloxy) phenyl ketone 5 mmol of 3-(1-triphenylmethyl-1H-imidazol-4-yl) propanol and 6 mmol of cyclopentyl 4-hydroxyphenyl ketone are treated as described in Example 76.

EF: $C_{18}H_{22}N_2O_2 \cdot C_4H_4O_4 \cdot 0 \cdot 25H_2O$ (419.0)
CHN analysis  Calculated  C  63.1  H  6.38  N  6.69
              Found       C  63.3  H  6.46  N  6.94
Yield: 80%                M.p.: 141° C.

EXAMPLE 84

Cyclohexyl 4-(3-(1H-imidazol-4-yl)propyloxy) phenyl ketone 5 mmol of 3-(1-triphenylmethyl-1H-imidazol-4-yl) propanol and 6 mmol of cyclohexyl 4-hydroxyphenyl ketone are treated as described in Example 76.

EF: $C_{19}H_{24}N_2O_2 \cdot C_4H_4O_4$ (428.5)
CHN analysis  Calculated  C  64.5  H  6.59  N  6.54
              Found       C  64.6  H  6.32  N  6.82
Yield: 80%                M.p.: 103° C.

EXAMPLE 85

4-(3-(1lH-Imidazol-4-yl)propyloxy)phenyl phenyl ketone 5 mmol of 3-(1-triphenylmethyl-1H-imidazol-4-yl) propanol and 6 mmol of 4-hydroxybenzophenone are treated as described in Example 76.

EF: $C_{19}H_{18}N_2O_2 \cdot C_4H_4O_4 \cdot 0 \cdot 25H_2O$ (426.9)
CHN analysis  Calculated  C  64.7  H  5.31  N  6.56
              Found       C  64.7  H  5.23  N  6.59
Yield: 70%                M.p.: 126° C.

EXAMPLE 86

4-(3-(1H-Imidazol-4-yl)propyloxy)phenyl 4-fluorophenyl ketone 5 mmol of 3-(1-triphenylmethyl-1H-imidazol-4-yl) propanol and 5 mmol of 4-fluoro-4'-hydroxybenzophenone are treated as described in Example 76.

EF: $C_{19}H_{17}N_2O_2F \cdot C_4H_4O_4$ (440.4)
CHN analysis  Calculated  C  62.7  H  4.81  N  6.36
              Found       C  62.6  H  4.83  N  6.43
Yield: 80%                M.p.: 125–127° C.

EXAMPLE 87

(4-(3-(1H-imidazol-4-yl)propyloxy)phenyl)methanol 2 mnol of (4-(3-(1H-imidazol-4-yl)propyloxy)phenyl)-carbaldehyde (Example 77) are placed in a suspension of 0.5 mmol LiAlH$_4$ in 10 ml anhydrous THF, and the reaction mixture is then refluxed for 1 hour. 5 ml of 2N NaOH are added, and the organic phase is separated, washed with water and dried with sodium carbonate.

After removal of the solvent under reduced pressure, the residue is crystallized as hydrogen maleate from diethyl ether and ethanol.

EF: $C_{13}H_{16}N_2O_2 \cdot C_4H_4O_4 \cdot 0 \cdot 25H_2O$ (352.9)
CHN analysis  Calculated  C  57.9  H  5.86  N  7.94
              Found       C  58.0  H  5.83  N  7.77
Yield: 50%                M.p.: 134° C.

EXAMPLE 88

1-(4-(3-(1H-Imidazol-4-yl)propyloxy)phenyl)ethanol 2 mmol of (4-(3-(1H-imidazol-4-yl)propyloxy)phenyl) ethanone (Example 78) are treated as described in Example 87.

EF: $C_{14}H_{18}N_2O_2 \cdot C_4H_4O_4 \cdot 0 \cdot 25H_2O$ (366.9)
CHN analysis  Calculated  C  58.9  H  6.18  N  7.64
              Found       C  58.8  H  6.22  N  7.62
Yield: 55%                M.p.: 95° C.

EXAMPLE 89

1-(4-(3-(1H-Imidazol-4-yl)propyloxy)phenyl-2-methyl-propanol 2 mmol of (4-(3-(1H-imidazol-4-yl)propyloxy)phenyl)-2-methylpropanone (Example 80) are treated as described in Example 87.

EF: $C_{16}H_{22}N_2O_2 \cdot C_4H_4O_4$ (390.4)
CHN analysis  Calculated  C  61.5  H  6.71  N  7.71
              Found       C  61.2  H  6.63  N  7.42
Yield: 55%                M.p.: 139° C.

EXAMPLE 90

Cyclopropyl 4-(3-(1H-Imidazol-4-yl)propyloxy)phenyl)methanol 2 mmol of cyclopropyl 4-(3-(1H-imidazol-4-yl)propyloxy)phenyl ketone (Example 81) are treated as described in Example 87.

EF: $C_{16}H_{20}N_2O_2 \cdot C_4H_4O_4$ (388.4)
CHN analysis  Calculated  C  61.9  H  6.23  N  7.21
              Found       C  61.9  H  6.29  N  7.12
Yield: 70%                M.p.: 84–85° C.

EXAMPLE 91

(4-(3-(1H-Imidazol-4-yl)propyloxy)phenyl)butanone 5 mmol of 3-(1-triphenylmethyl-1H-imidazol-4-yl)propanol and 6 mmol (4-hydroxyphenyl)butanone are treated as described in Example 76.

EF: $C_{16}H_{20}N_2O_2 \cdot C_4H_4O_4 \cdot H_2O$ (406.4)
CHN analysis  Calculated  C  59.1  H  6.45  N  6.89
              Found       C  59.2  H  6.23  N  7.30
Yield: 78%                M.p.: 87° C.

EXAMPLE 92

(4-(3-(1H-Imidazol-4-yl)propyloxy)phenyl)ethanone oxime 1.2 mmol of (4-(3-(1H-imidazol-4-yl)propyloxy)phenyl)ethanone (Example 78), 2.4 mmol of hydroxylamine hydrochloride and 4.8 mmol of NaOH are heated under reflux in 10 ml of water and 10 ml of ethanol for 7 hours. The mixture is concentrated under reduced pressure and alkalized with saturated $K_2CO_3$ solution, and the crude product is filtered off and washed with water. The product is crystallized as hydrogen maleate from diethyl ether and ethanol.

EF: $C_{14}H_{17}N_3O_2 \cdot C_4H_4O_4 \cdot 0 \cdot 5H_2O$ (384.4)
CHN analysis  Calculated  C  56.2  H  5.76  N  10.9
              Found       C  56.4  H  5.60  N  10.9
Yield: 31%                M.p.: 141-144° C.

EXAMPLE 93

(4-(3-(1H-Imidazol-4-yl)propyloxy)phenyl)ethanone O-methyloxime 1.2 mmol of (4-(3-(1H-imidazol-4-yl)propyloxy)phenyl)ethanone (Example 78) and 2.4 mmol of O-methylhydroxylamine hydrochloride are treated as described in Example 92.

EF: $C_{15}H_{19}N_3O_2 \cdot C_4H_4O_4 \cdot H_2O$ (389.4)
CHN analysis  Calculated  C  58.6  H  5.95  N  10.8
              Found       C  58.3  H  5.96  N  10.9
Yield: 42%                M.p.: 124–126° C.

EXAMPLE 94

(4-(3-(1H-Imidazol-4-yl)propyloxy)phenyl)-2-propaxnone 5 mmol of 3-(1-triphenylmethyl-1H-imidazol-4-yl)propanol and 6 mmol of (4-hydroxyphenyl)-2-propanone are treated as described in Example 76.

EF: $C_{15}H_{18}N_2O_2 \cdot C_4H_4O_4 \cdot 0 \cdot 5H_2O$ (383.4)
CHN analysis  Calculated  C  59.9  H  6.05  N  7.31
              Found       C  59.3  H  6.00  N  7.66
Yield: 70%                M.p.: 89° C.

EXAMPLE 95

3-(1H-Imidazol-4-yl)propyl 4-methoxyphenyl ether 5 mmol of 3-(1-triphenylmethyl-1H-imidazol-4-yl)propanol and 6 mmol of 4-methoxyphenol are treated as described in Example 76.

EF: $C_{13}H_{16}N_2O_2 \cdot C_4H_4O_4 \cdot 0 \cdot 25H_2O$ (352.9)
CHN analysis  Calculated  C  57.9  H  5.86  N  7.94
              Found       C  57.7  H  5.71  N  8.01
Yield: 85%                M.p.: 126° C.

EXAMPLE 96

N-(4-Acetylphenyl)-(3-(1H-imidazol-4-yl)propyl carbamate 5 mmol of 3-(1H-imidazol-4-yl)propanol.HCl and 5 mmol of acetylphenyl isocyanate are treated as described in Example 1.

EF: $C_{15}H_{17}N_3O_3 \cdot C_4H_4O_4 \cdot 0 \cdot 25H_2O$ (407.9)
CHN analysis  Calculated  C  56.0  H  5.31  N  10.3
              Found       C  56.0  H  5.20  N  10.3
Yield: 36%                M.p.: 158-159° C.

EXAMPLE 97

N-(3-Acetylphenyl)-(3-(1H-imidazol-4-yl)propyl carbamate 5 mmol of 3-(1H-imidazol-4-yl)propanol.HCl and 5 mmol of 3-acetylphenyl isocyanate are treated as described in Example 1.

EF: $C_{15}H_{17}N_3O_3 \cdot C_4H_4O_4 \cdot 0 \cdot 25H_2O$ (407.9)
CHN analysis  Calculated  C  56.0  H  5.31  N  10.3
              Found       C  56.2  H  5.29  N  10.2
Yield: 46%                M.p.: 136-137° C.

EXAMPLE 98

4-(3-(1H-Imidazol-4-yl)propyloxy)-2-butanone 5 mmol of 3-(1H-imidazol-4-yl)propanol.HCl and 10 mmol of 3-buten-2-one are heated at 40° C. for 1 hour in 20 ml of acetonitrile and one drop of conc. $H_2SO_4$. The mixture is neutralized with $Na_2CO_3$, the solvent is evaporated off and the residue purified by column chromatography (eluent: methylene chloride/methanol (90:10), ammoniacal atmosphere). After removal of the solvent under reduced pressure, the product is recrystallized as hydrogen maleate from diethyl ether and ethanol.

EF: $C_{10}H_{16}N_2O \cdot C_4H_4O_4 \cdot 0 \cdot 5H_2O$ (321.3)
CHN analysis  Calculated  C  52.3  H  6.59  N  9.16
              Found       C  51.9  H  6.45  N  9.07
Yield: 30%                M.p.: 56° C.

EXAMPLE 99

3-(1H-Imidazol-4-yl)propyl 2-methoxyethyl ether 5 mmol of sodium 3-(1-triphenylmethyl-1H-imidazol-4-yl)propanolate and 7 mmol of 2-methoxyethane chloride are treated as described in Example 5.

EF: $C_9H_{16}N_2O_2 \cdot C_4H_4O_4$ (247.3)
CHN analysis  Calculated  C  48.2  H  6.61  N  10.2
              Found       C  48.6  H  6.98  N  10.6
Yield: 20%                M.p.: 130-132° C.

EXAMPLE 100

3-Cyclopentylpropyl 3-(1H-imidazol-4-yl)propyl ether 5 mmol of sodium 3-(1-triphenylmethyl-1H-imidazol-4-yl)propanolate and 3-cyclopentylphenylpropane chloride are treated as described in Example 5.

EF: $C_{14}H_{24}N_2O \cdot C_4H_4O_4$ (352.4)
CHN analysis  Calculated  C  61.4  H  8.01  N  7.95
              Found       C  61.2  H  8.05  N  7.98
Yield: 70%                M.p.: 101° C.

EXAMPLE 101

3-(1H-Imidazol-4-yl)propyl-N-isoropyl carbamate 5 mmol of 3-(1H-imidazol-4-yl)propanol.HCl and 5 mmol of isopropyl isocyanate are treated as described in Example 1.

EF: $C_{10}H_{17}N_3O_2 \cdot C_4H_4O_4 \cdot 0 \cdot 25H_2O$ (331.8)
CHN analysis  Calculated  C  50.7  H  6.53  N  12.7
              Found       C  50.8  H  6.29  N  12.6
Yield: 45%                M.p.: 118–119° C.

EXAMPLE 102

N-(3,3-Diphenylpropyl)-3-(1H-imidazol-4-yl)propyl carbamate 5 mmol of 3-(1H-imidazol-4-yl)propanol.HCl and 5 mmol of 3,3-diphenylpropyl isocyanate are treated as described in Example 1.

EF: $C_{22}H_{25}N_3O_2 \cdot C_4H_4O_4$ (479.5)
CHN analysis  Calculated  C  65.1  H  6.10  N  8.76
              Found       C  65.0  H  6.18  N  8.63
Yield: 61%                M.p.: 126–128° C.

EXAMPLE 103

(1H-Imidazol-4-yl)nonane 10 mmol of nonyltriphenylphosphonium bromide, 10 mmol of (1-triphenymethyl-1H-imidazol-4-yl)methanal (see Example 51) are treated as described in Example 51. The product of this reaction ((1H-imidazol-4-yl)-1-nonene) is treated as described in Example 52.

EF: $C_{12}H_{22}N_2 \cdot C_2H_2O_4 \cdot H_2O$ (284.4)
CHN analysis  Calculated  C  59.1  H  8.51  N  9.85
              Found       C  59.1  H  8.39  N  9.79
Yield: 10%                M.p.: 137–138° C.

EXAMPLE 104

3-(4-(3-(1H-Imidazol-4-yl)propyloxy)phenyl) propenal 5 mmol of (4-(3-(1-triphenylmethyl-1H-imidazol-4-yl)propyloxy)phenyl)carbaldehyde (intermediate of Example 77) and 5 mmol of ethinylmagnesium bromide are dissolved in 20 ml of THF and refluxed for 1 h. The solvent is evaporated off and the residue heated for 2 h in 50 ml of 2N HCl. The lipophilic by-products are extracted with diethyl ether. The aqueous phase is alkalized with ammonia, and the crude product is extracted with diethyl ether and purified by rotatory chromatography (eluent: chloroform/methanol (99:1–90:10), ammoniacal atmosphere). After removal of the solvent under reduced pressure, the product is recrystallized as hydrogen maleate from diethyl ether and ethanol.

EF: $C_{15}H_{16}N_2O_2 \cdot C_4H_4O_4 \cdot O \cdot 5H_2O$ (381.4)
CHN analysis  Calculated  C  59.8  H  5.55  N  7.35
              Found       C  59.5  H  5.37  N  7.99
Yield: 36%                M.p.: 119–121° C.

EXAMPLE 105

4-[3-(4-Ethoxyphenoxy)propyl]-1H-imidazole

The procedure is as described in synthesis route A.
Salt form: oxalate

Crystallization solvent: 2-PrOH: Et$_2$O

| | | | | | | | |
|---|---|---|---|---|---|---|---|
| EF: C$_{14}$H$_{18}$N$_2$O$_2$ · 0 · 8C$_2$H$_2$O | | | | | | | |
| CHN analysis | Calculated | C | 58.8 | H | 6.21 | N | 8.80 |
| | Found | C | 59.0 | H | 6.35 | N | 8.94 |
| | | | M.p.: 191–193° C. | | | | |

EXAMPLE 106

4-[2-(3-Propanoylphenoxy)ethyl]-1H-imidazole

The procedure is as described in synthesis route F.
Salt form: oxalate
Crystallization solvent: EtOH

| | | | | | | | |
|---|---|---|---|---|---|---|---|
| EF: C$_{14}$H$_{16}$N$_2$O$_2$ · 0 · 8C$_2$H$_2$O$_4$ | | | | | | | |
| CHN analysis | Calculated | C | 59.2 | H | 5.61 | N | 8.86 |
| | Found | C | 59.5 | H | 5.62 | N | 8.85 |
| | | | M.p.: 148–150° C. | | | | |

EXAMPLE 107

4-[3-(3-Hydroxyiminomethylenephenoxy)propyl]-1H-imidazole

The procedure is as described in the synthesis route below.
Salt form: oxalate
Crystallization solvent: 2-PrOH: Et$_2$OH

| | | | | | | | |
|---|---|---|---|---|---|---|---|
| EF: C$_{13}$H$_{15}$N$_3$O$_2$ · C$_2$H$_2$O$_4$ | | | | | | | |
| CHN analysis | Calculated | C | 53.7 | H | 5.50 | N | 12.5 |
| | Found | C | 53.7 | H | 5.11 | N | 12.5 |
| | | | M.p.: 120–122° C. | | | | |

Preparation of 4-[3-(3-hydroxyiminamethylenephenoxy)propyl]-1H-imidazole oxalate A mixture of hydroxylamine hydrochloride (0.5:7.24 mmol) and sodium acetate (1 g; 0.012 mmol) in 10 ml of water is stirred for 10 min. A solution of 4-[3-(3-formylphenoxy)propyl]-1H-imidazole (0.25 g; 1.08 mmol) in 3 ml of ethanol is then added slowly and the mixture is heated at 80° C. for 2 hours. The solvent is removed under reduced pressure, leaving a white residue which is extracted with chloroform (3×100 ml). The combined chloroform extracts are dried (MgSO$_4$) and evaporated under reduced pressure, leaving an oil (0.11 g). The latter is dissolved in 2-propanol (3 ml) and treated with an excess of oxalic acid (1.5 equiv.) in 2 ml of 2-propanol. The product, which is precipitated by adding diethyl ether, is filtered off and washed with diethyl ether, and has a melting point of 120–122° C.

EXAMPLE 108

4-[3-(3-Formylphenoxy)propyl]-1H-imidazole

The procedure is as described in synthesis route A.
Salt form: oxalate
Crystallization solvent: EtOH

| | | | | | | | |
|---|---|---|---|---|---|---|---|
| EF: C$_{13}$H$_{14}$N$_2$O$_2$ · 0 · 85C$_2$H$_2$O$_4$ · 0 · 1H$_2$O | | | | | | | |
| CHN analysis | Calculated | C | 57.6 | H | 5.22 | N | 9.31 |
| | Found | C | 57.3 | H | 4.89 | N | 9.65 |
| | | | M.p.: 158–160° C. | | | | |

EXAMPLE 109

4-[3-(4-Benzyloxyphenoxy)propyl]-1H-imidazole

The procedure is as described in synthesis route A.
Salt form: base
Crystallization solvent: EtOH

| | | | | | | | |
|---|---|---|---|---|---|---|---|
| EF: C$_{19}$H$_{20}$N$_2$O$_2$ · 0 · 85H$_2$O | | | | | | | |
| CHN analysis | Calculated | C | 70.9 | H | 6.73 | N | 8.70 |
| | Found | C | 70.9 | H | 6.44 | N | 8.55 |
| | | | M.p.: 135–137° C. | | | | |

EXAMPLE 110

3-(1H-Imidazol-4-yl)propyl N-(2-methyl-2-butyl)carbamate 5 mmol of 2,2-dimethylbutyric acid, 5 mmol of triethylamine and 5 mmol of diphenyl phosphorazidate in 30 ml of anhydrous acetonitrile are stirred at 20° C. for 45 minutes and are then brought to reflux for 30 minutes. 6 mmol of 3-(1H-imidazol-4-yl)propanol.HCl are added and are brought to reflux for 40 hours. The mixture is evaporated and the residue dissolved in diethyl ether. The solution is washed successively with 30 ml of 5% aqueous citric acid, 30 ml of H$_2$O and 30 ml of saturated aqueous NaHCO$_3$. The organic layer is evaporated and the residue is purified by rotatory chromatography (eluent: chloroform/methanol (99:1–90:10)). After removal of the solvent under reduced pressure, the residue is crystallized in the form of hydrogen oxalate in diethyl ether and ethanol.

| | | | | | | | |
|---|---|---|---|---|---|---|---|
| C$_{12}$H$_{21}$N$_3$O$_2$ · C$_2$H$_2$O$_4$ (329.4) | | | | | | | |
| CHN analysis | Calculated | C | 51.1 | H | 7.04 | N | 12.8 |
| | Found | C | 51.1 | H | 6.93 | N | 13.1 |
| Yield: 15% | | | M.p.: 129–130° C. | | | | |

EXAMPLE 111

N-(2,2-Dimethylpropyl)-3-(1H-imidazol-4-yl)propyl carbamate 5 mmol of 3,3-dimethylbutyric acid, 5 mmol of triethylamine and 5 mmol of diphenyl phosphorazidate are treated as described in Example 110.

| | | | | | | | |
|---|---|---|---|---|---|---|---|
| C$_{12}$H$_{21}$N$_3$O$_2$ · C$_2$H$_2$O$_4$ · 0 · 5H$_2$O (338.4) | | | | | | | |
| CHN analysis | Calculated | C | 49.7 | H | 7.15 | N | 12.4 |
| | Found | C | 49.8 | H | 6.81 | N | 12.3 |
| Yield: 20% | | | M.p.: 131–132° C. | | | | |

EXAMPLE 112

3-(1H-Imidazol-4-yl)propyl-N-(2-propenyl)carbamate 5 mmol of 3-(1H-imidazol-4-yl)propanol.HCl and 5 mmol of 2-propenyl isocyanate are treated as described in Example 1.

| $C_{10}H_{15}N_3O_2 \cdot C_4H_4O_4$ (325.3) | | | | | | |
|---|---|---|---|---|---|---|
| CHN analysis | Calculated | C | 51.7 | H | 5.89 | N | 12.9 |
| | Found | C | 51.5 | H | 5.84 | N | 12.8 |
| Yield: 90% | | | M.p.: 88° C. | | | |

EXAMPLE 113

3-(1H-Imidazol-4-yl)propyl-N-(3-phenyl-3-pentyl) carbamate 5 mmol of 2-ethyl-2-phenylbutyric acid, 5 mmol of triethylamine and 5 mmol of diphenyl phosphorazidate are treated as described in Example 110.

| $C_{18}H_{25}N_3O_2 \cdot C_2H_2O_4 \cdot 0 \cdot 5H_2O$ (414.5) | | | | | | |
|---|---|---|---|---|---|---|
| CHN analysis | Calculated | C | 58.0 | H | 6.81 | N | 10.1 |
| | Found | C | 57.7 | H | 6.87 | N | 9.77 |
| Yield: 35% | | | M.p.: 147–148° C. | | | |

EXAMPLE 114

N-(1,1-Diphenylethyl)-3-(1H-imidazol-4-yl)propyl carbamate 5 mmol of 2,2-diphenylpropionic acid, 5 mmol of triethylamine and 5 mmol of diphenyl phosphorazidate are treated as described in Example 110.

| $C_{21}H_{23}N_3O_2 \cdot C_2H_2O_4 \cdot 0 \cdot 25H_2O$ (444.0) | | | | | | |
|---|---|---|---|---|---|---|
| CHN analysis | Calculated | C | 62.2 | H | 5.79 | N | 9.46 |
| | Found | C | 62.4 | H | 5.80 | N | 9.46 |
| Yield: 45% | | | M.p.: 131–132° C. | | | |

EXAMPLE 115

N-(3,5-Dimethylphenyl)-3-(1H-imidazol-4-yl)propyl carbamate 5 mmol of 3-(1H-imidazol-4-yl)propanol.HCl and 5 mmol of 3,5-dimethylphenyl isocyanate are treated as described in Example 1.

| $C_{15}H_{19}N_3O_2 \cdot C_4H_4O_4 \cdot 0 \cdot 25H_2O$ (393.9) | | | | | | |
|---|---|---|---|---|---|---|
| CHN analysis | Calculated | C | 57.9 | H | 6.01 | N | 10.7 |
| | Found | C | 57.9 | H | 6.22 | N | 10.6 |
| Yield: 40% | | | M.p.: 107–108° C. | | | |

EXAMPLE 116

1,1-Dimethylethyl 2-(1H-imidazol-4-yl)ethyl ether 2 mmol of 2-(1-triphenylmethyl-1H-imidazol-4-yl) ethanol and 4 mmol of tert-butyl trichloroacetimidate are dissolved in 4 ml of cyclohexane and 2 ml of dichloromethane. After the addition of 120 µl of boron trifluoride etherate, the solution is stirred at 60–70° C. for 18 hours. Filtration of the reaction mixture and evaporation of the solvent are followed by a detritylation in 2 ml of ethanol, 2 ml of acetone and 15 ml of 2N HCl at 70° C. The ethanol and acetone are removed under reduced pressure and triphenylmethanol is extracted with diethyl ether. The aqueous layer is alkalized with ammonia and extracted with diethyl ether. Evaporation of the solvent and final purification by column chromatography (eluent: dichloromethane/methanol, 90:10) yield the product in the form of an oil, which is crystallized in the form of the hydrogen oxalate in ethanol and diethyl ether.

| $C_9H_{16}N_2O \cdot 0 \cdot 8C_2H_2O_4$ (240.3) | | | | | | |
|---|---|---|---|---|---|---|
| CHN analysis | Calculated | C | 53.0 | H | 7.38 | N | 11.7 |
| | Found | C | 53.1 | H | 7.38 | N | 11.6 |
| Yield: 15% | | | M.p.: 168° C. | | | |

EXAMPLE 117

1,1-Dimethylethyl 3-(1H-imidazol-4-yl)propyl ether 5 mmol of 3-(1-triphenylmethyl-1H-imidazol-4-yl) propanol and 10 mmol of tert-butyl trichloroacetimidate are treated as described in Example 116. The title compound is crystallized in the form of the hydrogen maleate in ethanol and diethyl ether.

| $C_{10}H_{18}N_2O \cdot C_4H_4O_4 \cdot 0 \cdot 25H_2O$ (302.8) | | | | | | |
|---|---|---|---|---|---|---|
| CHN analysis | Calculated | C | 55.5 | H | 7.49 | N | 9.25 |
| | Found | C | 55.8 | H | 7.30 | N | 9.12 |
| Yield: 15% | | | M.p.: 132° C. | | | |

EXAMPLE 118

3-(1H-Imidazol-4-yl)propyl 2-propenyl ether 5 mmol of 3-(1-triphenylmethyl-1H-imidazol-4-yl) propanol and 5 mmol of 3-bromo-1-propene are treated as described in Example 5. The title compound is crystallized in the form of the hydrogen oxalate from ethanol and diethyl ether.

| $C_9H_{14}N_2O \cdot 0 \cdot 8C_2H_2O_4$ (238.3) | | | | | | |
|---|---|---|---|---|---|---|
| CHN analysis | Calculated | C | 53.4 | H | 6.60 | N | 11.8 |
| | Found | C | 53.3 | H | 6.61 | N | 11.6 |
| Yield: 20% | | | M.p.: 158–159° C. | | | |

EXAMPLE 119

3-(1H-Iinidazol-4-yl)propyl 4-pentenyl ether 5 mmol of 3-(1-triphenylmethyl-1H-imidazol-4-yl) propanol and 5 mmol of 5-bromo-1-pentene are treated as described in Example 5. The title compound is crystallized in the form of the hydrogen oxalate from ethanol and diethyl ether.

| $C_{11}H_{18}N_2O \cdot C_2H_2O_4 \cdot 0 \cdot 75H_2O$ (297.8) | | | | | | |
|---|---|---|---|---|---|---|
| CHN analysis | Calculated | C | 52.4 | H | 7.28 | N | 9.41 |
| | Found | C | 52.6 | H | 7.03 | N | 9.56 |
| Yield: 15% | | | M.p.: 156° C. | | | |

EXAMPLE 120

3-(1H-Imidazol-4-yl)propyl 2-propynyl ether 5 mmol of 3-(1-triphenylmethyl-1H-imidazol-4-yl) propanol and 5 mmol of 3-bromo-1-propyne are treated as described in Example 5. The title compound is crystallized in the form of the hydrogen oxalate from ethanol and diethyl ether.

$C_9H_{12}N_2O \cdot 0 \cdot 75C_2H_2O_4$ (231.7)
| CHN analysis | Calculated | C | 54.4 | H | 5.87 | N | 12.1 |
|---|---|---|---|---|---|---|---|
| | Found | C | 54.2 | H | 5.85 | N | 12.0 |
| Yield: 20% | | | | M.p.: 148° C. | | | |

EXAMPLE 121

4-Butylphenyl 3-(1H-imidazol-4-yl)propyl ether 0.8 mmol of cyclopropyl 4-(3-(1H-imidazol-4-yl) propyloxy)phenyl ketone (Example 61), 4 mmol of hydrazine hydrate and 3.2 mmol of KOH in 30 ml of triethylene glycol are brought to reflux for 2 hours. The solvent is evaporated off under reduced pressure, and the crude product is extracted with dichloromethane and purified by rotatory chromatography (eluent:dichloromethane/methanol (99:1)–(90:10), ammoniacal atmosphere). The product is crystallized in the form of hydrogen maleate from diethyl ether and ethanol.

$C_{16}H_{22}N_2O \cdot 0 \cdot 75C_2H_2O_4$ (325.9)
| CHN analysis | Calculated | C | 64.5 | H | 7.27 | N | 8.60 |
|---|---|---|---|---|---|---|---|
| | Found | C | 64.2 | H | 7.54 | N | 8.41 |
| Yield: 20% | | | | M.p.: 193° C. | | | |

EXAMPLE 122

4-(1-Ethynyl)phenyl 3-(1H-imidazol-4-yl)propyl ether 10 mmol of 3-(1H-imidazol-4-yl)propanol are reacted with 12 mmol of di-tert-butyl dicarbonate in 20 ml of acetonitrile, 5 ml of triethylamine and 5 ml of $H_2O$ in the presence of 1 mmol of 4-(N,N-dimethylamino)pyridine at room temperature for 2 hours. Evaporation of the solvent and final purification by column chromatography (eluent:dichloromethane/methanol, 90:10) yield 4-(3-hydroxypropyl)-1H-imidazole-1-carboxylic acid tert-butyl ester in the form of an oil.

4-(2-(Trimethylsilyl)-1-ethynyl)phenol is prepared from 4-iodoanisole according to Sonogashira K. et al., Tetrahedron Lett. 1975, 50, 4467 and Feutrill, G. I. et al., ibid, 1970, 16, 1327.

5 mmol of the latter compound are reacted with 5 mmol of the former as described in Example 56.

$C_{14}H_{14}N_2O \cdot C_4H_4O_4 \cdot 0 \cdot 25H_2O$ (346.9)
| CHN analysis | Calculated | C | 62.3 | H | 5.38 | N | 8.08 |
|---|---|---|---|---|---|---|---|
| | Found | C | 62.4 | H | 5.28 | N | 8.07 |
| Yield: 70% | | | | M.p.: 150° C. | | | |

EXAMPLE 123

3-(1H-Imidazol-4-yl)propyl 4-(1-pentynyl)phenyl ether 5 mmol of 4-(3-hydroxypropyl)-1H-imidazole-1-carboxylic acid tert-butyl ester and 5 mmol of 4-(1-pentynyl)phenol are treated as described in Example 122.

$C_{17}H_{20}N_2O \cdot C_4H_4O_4 \cdot 0 \cdot 25H_2O$ (388.9)
| CHN analysis | Calculated | C | 64.9 | H | 6.35 | N | 7.20 |
|---|---|---|---|---|---|---|---|
| | Found | C | 64.9 | H | 6.54 | N | 7.22 |
| Yield: 85% | | | | M.p.: 126° C. | | | |

EXAMPLE 124

4-(3,3-Dimethyl-1-butynyl)phenyl 3-(1-imidazol-4-yl)propyl ether 5 mmol of 4-(3-hydroxypropyl)-1H-imidazole-1-carboxylic acid tert-butyl ester and 5 mmol of 4-(3,3-dimethyl-1-butynyl)phenol are treated as described in Example 122.

$C_{18}H_{22}N_2O \cdot C_4H_4O_4 \cdot 0 \cdot 5H_2O$ (407.5)
| CHN analysis | Calculated | C | 64.9 | H | 6.68 | N | 6.87 |
|---|---|---|---|---|---|---|---|
| | Found | C | 64.9 | H | 6.67 | N | 6.64 |
| Yield: 95% | | | | M.p.: 132° C. | | | |

EXAMPLE 125

4-(Fluorophenyl)-4-(3-(1H-imidazol-4-yl)propyloxy)butanone 5 mmol of sodium 3-(1-triphenylmethyl-1H-imidazol-4-yl)propanolate and 5 mmol of 2-(3-chloropropyl)-2-(4-fluorophenyl)-1,3-dioxolane are treated as described in Example 5, but the cleavage solvent consists of 30 ml of $HCl/H_2SO_4$ (1:1) and the oil is crystallized in the form of hydrogen oxalate from diethyl ether and ethanol.

$C_{16}H_{19}N_2O_2F \cdot C_2H_2O_4 \cdot 0 \cdot 25H_2O$ (384.9)
| CHN analysis | Calculated | C | 56.2 | H | 5.63 | N | 7.28 |
|---|---|---|---|---|---|---|---|
| | Found | C | 55.9 | H | 5.67 | N | 7.39 |
| Yield: 30% | | | | M.p.: 119° C. | | | |

EXAMPLE 126

Cyclopropyl 4-(2-(1H-imidazol-4-yl) ethyloxy) phenyl ketone 5 mmol of sodium 2-(1-triphenylmethyl-1H-imidazol-4-yl)ethanolate and 10 mmol of cyclopropyl 4-fluorophenyl ketone are treated as described in Example 61 (method A).

$C_{15}H_{16}N_2O_2 \cdot C_4H_4O_4$ (372.4)
| CHN analysis | Calculated | C | 61.3 | H | 5.41 | N | 7.52 |
|---|---|---|---|---|---|---|---|
| | Found | C | 61.3 | H | 5.32 | N | 7.43 |
| Yield: 20% | | | | M.p.: 133° C. | | | |

EXAMPLE 127

(4-(3-(1H-Imidazol-4-yl)propyloxy)phenyl) pentanone 5 mmol of 3-(1-triphenylmethyl-1H-imidazol-4-yl) propanol and 10 mmol of cyclopropyl 4-fluorophenyl ketone are treated as described in Example 61 (method A).

$C_{17}H_{22}N_2O_2 \cdot C_4H_4O_4 \cdot 0 \cdot 5H_2O$ (411.5)
CHN analysis  Calculated  C  61.3  H  6.61  N  6.81
              Found       C  60.9  H  6.40  N  6.55
Yield: 80%                         M.p.: 85° C.

EXAMPLE 128

(4-(3-(1H-Imidazol-4-yl)propyloxy)phenyl) hexanone 5 mmol of 3-(1-triphenylmethyl-1H-imidazol-4-yl) propanol and 6 mmol of (4-hydroxyphenyl)hexanone (prepared from hexanoic acid according to standard methods (Friedel-Crafts acylation)) are treated as described in Example 56.

$C_{18}H_{24}N_2O_2 \cdot C_4H_4O_4$ (416.5)
CHN analysis  Calculated  C  63.4  H  6.78  N  6.73
              Found       C  63.2  H  6.78  N  6.70
Yield: 70%                         M.p.: 114° C.

EXAMPLE 129

3,3-Dimethyl-(4-(3-(1H-imidazol-4-yl)propyloxy) phenyl)butanone 5 mmol of 3-(1-triphenylmethyl-1H-imidazol-4-yl) propanol and 5 mmol of 4-(3,3-dimethyl-1-butynyl)phenol are treated as described in Example 56. Detritylation in 2N HCl yields the title compound.

$C_{18}H_{24}N_2O_2 \cdot C_4H_4O_4$ (416.5)
CHN analysis  Calculated  C  63.5  H  6.78  N  6.73
              Found       C  63.3  H  6.88  N  6.63
Yield: 60%                         M.p.: 139° C.

EXAMPLE 130

4-Hydroxy-(4-(3-(1H-imidazol-4-yl)propyloxy) phenyl)butanone 5 mmol of sodium 3-(1-triphenylmethyl-1H-imidazol-4-yl)propanolate and 10 mmol of 2-(4-(4-fluorophenyl)-4-oxobutyl)malonic acid diethyl ester (prepared from 2-(3-chloropropyl)-2-(4-fluorophenyl)-1,3-dioxolane with malonic acid according to standard methods) are treated as described in Example 61 (method A).

$C_{16}H_{20}N_2O_3 \cdot C_4H_4O_4$ (404.4)
CHN analysis  Calculated  C  59.4  H  5.98  N  6.93
              Found       C  59.1  H  6.08  N  7.01
Yield: 20%                         M.p.: 107° C.

EXAMPLE 131

4-Hydroxy-(4-(3-(1H-imidazol-4-yl)propyloxy) phenyl)butanone ethylene acetal 1.3 mmol of cyclopropyl 4-(3-(1H-imidazol-4-yl) propyloxy)phenyl ketone (Example 61) and a catalytic amount of 4-toluenesulphonic acid in 15 ml of ethylene glycol are brought to reflux for 5 hours. The solvent is evaporated off under reduced pressure, and the residue is dissolved in 10 ml of $H_2O$ and alkalized with ammonia. The crude product is extracted with dichloromethane and purified by rotatory chromatography (eluent: dichloromethane/methanol (99:1–90:10), ammoniacal atmosphere). The product is crystallized in the form of hydrogen maleate from diethyl ether and ethanol.

$C_{18}H_{24}N_2O_4 \cdot C_4H_4O_4$ (448.5)
CHN analysis  Calculated  C  58.9  H  6.29  N  6.25
              Found       C  59.0  H  6.32  N  6.19
Yield: 55%                         M.p.: 104° C.

EXAMPLE 132

5-(3-(1H-Imidazol-4-yl)propyloxy)-1-indanone 5 mmol of 3-(1-triphenylmethyl-1H-imidazol-4-yl) propanol and 6 mmol of 5-hydroxy-1-indanone are treated as described in Example 56.

$C_{15}H_{16}N_2O_2 \cdot C_4H_4O_4 \cdot H_2O$ (390.4)
CHN analysis  Calculated  C  58.5  H  5.68  N  7.17
              Found       C  58.8  H  5.87  N  7.30
Yield: 70%                         M.p.: 144° C.

EXAMPLE 133

3,4-Dihydro-6-(3-(1H-imidazol-4-yl)propyloxy)-2H-naphthalen-1-one 5 mmol of 3-(1-triphenylmethyl-1H-imidazol-4-yl) propanol and 6 mmol of 3,4-dihydro-6-hydroxy-2H-naphthalen-1-one are treated as described in Example 56.

$C_{16}H_{18}N_2O_2 \cdot C_4H_4O_4 \cdot 0 \cdot 5H_2O$ (395.4)
CHN analysis  Calculated  C  60.8  H  5.86  N  7.08
              Found       C  60.5  H  5.72  N  7.15
Yield: 40%                         M.p.: 100–102° C.

EXAMPLE 134

(4-(3-(1H-Imidazol-4-yl)propyloxy)-2-methylphenyl)ethanone 5 mmol of 3-(1-triphenylmethyl-1H-imidazol-4-yl) propanol and 6 mmol of (4-hydroxy-2-methylphenyl)

ethanone are treated as described in Example 56, but isolated in the form of the free base.

| $C_{15}H_{18}N_2O_2$ (258.3) | | | | | | |
|---|---|---|---|---|---|---|
| CHN analysis | Calculated | C | 69.7 | H | 7.02 | N | 10.8 |
| | Found | C | 69.4 | H | 7.07 | N | 10.5 |
| Yield: 70% | | | M.p.: 143° C. | | | |

EXAMPLE 135

(2-Fluoro-4-(3-(1H-imidazol-4-yl)propyloxy)phenyl) ethanone 5 mmol of 3-(1-triphenylmethyl-1H-imidazol-4-yl) propanol and 6 mmol of (2-fluoro-4-hydroxyphenyl) ethanone are treated as described in Example 56.

| $C_{14}H_{15}N_2O_2F \cdot C_4H_4O_4 \cdot 0 \cdot 25H_2O$ (382.9) | | | | | | |
|---|---|---|---|---|---|---|
| CHN analysis | Calculated | C | 56.5 | H | 5.13 | N | 7.32 |
| | Found | C | 56.4 | H | 5.27 | N | 7.20 |
| Yield: 70% | | | M.p.: 115° C. | | | |

EXAMPLE 136

(2-Fluoro-4-(3-(1H-imidazol-4-yl)propyloxy)phenyl) propanone 5 mmol of sodium 3-(1-triphenylmethyl-1H-imidazol-4-yl)propanolate and 10 mmol of (2,4-difluorophenyl) propanone are treated as described in Example 61 (method A).

| $C_{15}H_{17}N_2O_2F \cdot C_4H_4O_4 \cdot 0 \cdot 25H_2O$ (396.9) | | | | | | |
|---|---|---|---|---|---|---|
| CHN analysis | Calculated | C | 57.5 | H | 5.46 | N | 7.06 |
| | Found | C | 57.7 | H | 5.55 | N | 7.06 |
| Yield: 30% | | | M.p.: 122° C. | | | |

EXAMPLE 137

4-(3-(1H-Imidazol-4-yl)propyloxy)phenyl) 2-thienyl ketone 5 mmol of sodium 3-(1-triphenylmethyl-1H-imidazol-4-yl)propanrolate and 10 mmol of 4-fluorophenyl 2-thienyl ketone are treated as described in Example 61 (method A).

| $C_{17}H_{16}N_2O_2S \cdot C_2H_2O_4$ (402.4) | | | | | | |
|---|---|---|---|---|---|---|
| CHN analysis | Calculated | C | 56.7 | H | 4.51 | N | 6.96 |
| | Found | C | 56.8 | H | 4.57 | N | 6.97 |
| Yield: 10% | | | M.p.: 174° C. | | | |

EXAMPLE 138

(4-(3-(1H-Imidazol-4-yl)propyloxy)phenyl) carbaldehyde oxime 1.2 mmol of (4-(3-(1H-imidazol-4-yl)propyloxy)phenyl) carbaldehyde (Example 57) and 2.4 mmol of hydroxylamine hydrochloride in 20 ml of anhydrous ethanol are heated to reflux for 3 hours. The mixture is concentrated under reduced pressure and alkalized with saturated $K_2CO_3$ solution and the crude product is isolated and washed with water. The product is crystallized in the form of the hydrogen maleate from diethyl ether and ethanol.

| $C_{13}H_{15}N_3O_2 \cdot C_4H_4O_4 \cdot 0 \cdot 5H_2O$ (370.4) | | | | | | |
|---|---|---|---|---|---|---|
| CHN analysis | Calculated | C | 55.1 | H | 5.44 | N | 11.4 |
| | Found | C | 54.8 | H | 5.27 | N | 11.0 |
| Yield: 70% | | | M.p.: 154° C. | | | |

EXAMPLE 139

(4-(3-(1H-Imidazol-4-yl)propyloxy)phenyl) propanone oxime 1.2 mmol of (4-(3-(1H-imidazol-4-yl)propyloxy)phenyl) propanone (Example 59) are treated as described in Example 138.

| $C_{15}H_{19}N_3O_2 \cdot C_4H_4O_4 \cdot 0 \cdot 5H_2O$ (398.4) | | | | | | |
|---|---|---|---|---|---|---|
| CHN analysis | Calculated | C | 57.3 | H | 6.07 | N | 10.6 |
| | Found | C | 57.3 | H | 6.25 | N | 10.7 |
| Yield: 80% | | | M.p.: 114° C. | | | |

EXAMPLE 140

(4-(3-(1H-Imidazol-4-yl)propyloxy)phenyl)butanone oxime 1.2 mmol of (4-(3-(1H-imidazol-4-yl)propyloxy)phenyl) butanone (Example 71) are treated as described in Example 138.

| $C_{16}H_{21}N_3O_2 \cdot C_4H_4O_4 \cdot 0 \cdot 25H_2O$ (407.9) | | | | | | |
|---|---|---|---|---|---|---|
| CHN analysis | Calculated | C | 58.9 | H | 6.30 | N | 10.3 |
| | Found | C | 58.7 | H | 6.61 | N | 10.4 |
| Yield: 80% | | | M.p.: 129° C. | | | |

EXAMPLE 141

(4-(3-(1H-Imidazol-4-yl)propyloxy)phenyl) pentanone oxime 1.2 mmol of (4-(3-(1H-imidazol-4-yl)propyloxy)phenyl) pentanone (Example 127) are treated as described in Example 138, but isolated in the form of the free base.

| $C_{17}H_{23}N_3O_2 \cdot 0 \cdot 25H_2O$ (305.9) | | | | | | |
|---|---|---|---|---|---|---|
| CHN analysis | Calculated | C | 66.8 | H | 7.74 | N | 13.7 |
| | Found | C | 66.6 | H | 7.82 | N | 13.7 |
| Yield: 80% | | | M.p.: 131° C. | | | |

EXAMPLE 142

(4-(3-(1H-Imidazol-4-yl)propyloxy)phenyl) hexanone oxime 1.2 mmol of (4-(3-(1H-imidazol-4-yl)propyloxy)phenyl) hexanone (Example 128) are treated as described in Example 138, but isolated in the form of the free base.

| $C_{18}H_{25}N_3O_2 \cdot 0 \cdot 25H_2O$ (324.4) | | | | | | |
|---|---|---|---|---|---|---|
| CHN analysis | Calculated | C | 66.6 | H | 8.08 | N | 13.0 |
| | Found | C | 66.4 | H | 7.81 | N | 12.8 |
| Yield: 80% | | | M.p.: 138° C. | | | |

EXAMPLE 143

Cyclopropyl 4-(3-(1H-imidazol-4-yl)propyloxy) phenyl ketone oxime 1.2 mmol of cyclopropyl 4-(3-(1H-imidazol-4-yl)propyloxy)phenyl ketone (Example 61) and 2.4 mmol of hydroxylamine hydrochloride in 20 ml of anhydrous ethanol are heated at 60° C. for 5 hours. The mixture is treated as described in Example 138, but isolated in the form of the free base.

| $C_{16}H_{19}N_3O_2 \cdot 0 \cdot 25H_2O$ (289.9) | | | | | | |
|---|---|---|---|---|---|---|
| CHN analysis | Calculated | C | 66.3 | H | 6.78 | N | 14.5 |
| | Found | C | 66.6 | H | 6.62 | N | 14.6 |
| Yield: 55% | | | M.p.: 213° C. | | | |

EXAMPLE 144

(4-(3-(1H-Imidazol-4-yl)propyloxy)-2-methylphenyl)ethanone oxime 1.2mmol of (4-(3-(1H-imidazol-4-yl)propyloxy)-2-methylphenyl)ethanone (Example 134) are treated as described in Example 138, but isolated in the form of the free base.

| $C_{15}H_{19}N_3O_2$ (273.3) | | | | | | |
|---|---|---|---|---|---|---|
| CHN analysis | Calculated | C | 65.9 | H | 7.01 | N | 15.4 |
| | Found | C | 65.6 | H | 7.06 | N | 15.2 |
| Yield: 80% | | | M.p.: 190° C. | | | |

EXAMPLE 145

(2-Fluoro-4-(3-(1H-imidazol-4-yl)propyloxy)phenyl)ethanone oxime 1.2 mmol of (2-fluoro-4-(3-(1H-imidazol-4-yl)propyloxy)phenyl)ethanone (Example 135) are treated as described in Example 138.

| $C_{14}H_{16}N_3O_2F \cdot C_4H_4O_4$ (393.4) | | | | | | |
|---|---|---|---|---|---|---|
| CHN analysis | Calculated | C | 55.0 | H | 5.12 | N | 10.7 |
| | Found | C | 54.9 | H | 5.40 | N | 10.7 |
| Yield: 70% | | | M.p.: 134° C. | | | |

EXAMPLE 146

(4-(3-(1H-Imidazol-4-yl)propyloxy)phenyl) carbaldehyde O-methyloxime 1.2 mmol of (4-(3-(1H-imidazol-4-yl)propyloxy)phenyl)carbaldehyde (Example 57) and 2.4 mmol of O-methylhydroxylamine hydrochloride are treated as described in Example 138.

| $C_{14}H_{17}N_3O_2 \cdot C_4H_4O_4 \cdot 0 \cdot 25H_2O$ (379.9) | | | | | | |
|---|---|---|---|---|---|---|
| CHN analysis | Calculated | C | 56.9 | H | 5.70 | N | 11.1 |
| | Found | C | 56.7 | H | 5.54 | N | 11.0 |
| Yield: 85% | | | M.p.: 131–132° C. | | | |

EXAMPLE 147

(4-(3-(1H-Imidazol-4-yl)propyloxy)phenyl)ethanone semicarbazone 1.2 mmol of (4-(3-(1H-imidazol-4-yl)propyloxy)phenyl)ethanone (Example 58) and 2.4 mmol of semicarbazide hydrochloride are treated as described in Example 138.

| $C_{15}H_{19}N_5O_2 \cdot C_4H_4O_4 \cdot 0 \cdot 5H_2O$ (426.4) | | | | | | |
|---|---|---|---|---|---|---|
| CHN analysis | Calculated | C | 53.5 | H | 5.67 | N | 16.4 |
| | Found | C | 53.5 | H | 5.62 | N | 16.4 |
| Yield: 85% | | | M.p.: 159° C. | | | |

EXAMPLE 148

6-(3-(H-imidazol-4-yl)propyloxy)-2H-1,3-benzoxathiol-2-one 5 mmol of 3-(1-triphenylmethyl-1H-imidazol-4-yl)propanol and 6 mmol of 6-hydroxy-2H—1,3-benzoxathiol-2-one are treated as described in Example 56.

| $C_{13}H_{12}N_2O_3S \cdot C_4H_4O_4 \cdot 1 \cdot 75H_2O$ (423.9) | | | | | | |
|---|---|---|---|---|---|---|
| CHN analysis | Calculated | C | 48.2 | H | 4.64 | N | 6.61 |
| | Found | C | 48.0 | H | 4.48 | N | 6.38 |
| Yield: 40% | | | M.p.: 147° C. | | | |

EXAMPLE 149

3-(1H-Imidazol-4-yl)propyl 4-(5-methyl-1,2,4-oxadiazol-3-yl)phenyl ether 5 mmol of 3-(1-triphenylmethyl-1H-imidazol-4-yl)propanol and 6 mmol of (5-methyl-1,2,4-oxadiazol-3-yl)phenol (prepared according to Swain, C. J. et al. J. Med. Chem. 1991, 34, 140) are treated as described in Example 56, but isolated in the form of the free base.

| $C_{15}H_{16}N_4O_2 \cdot H_2O$ (302.3) | | | | | | |
|---|---|---|---|---|---|---|
| CHN analysis | Calculated | C | 59.6 | H | 6.00 | N | 18.5 |
| | Found | C | 59.8 | H | 5.84 | N | 18.2 |
| Yield: 60% | | | M.p.: 146° C. | | | |

EXAMPLE 150

4-Fluorophenyl 4-(3-(1H-imidazol-4-yl)propyloxy) phenyl sulphone 5 mmol of sodium 3-(1-triphenylmethyl-1H-imidazol-4-yl)propanolate and 10 mmol of bis(4-fluorophenyl) sulphone are treated as described in Example 61 (method A).

| $C_{18}H_{17}N_2O_3FS \cdot HCl$ (396.9) | | | | | | |
|---|---|---|---|---|---|---|
| CHN analysis | Calculated | C | 54.5 | H | 4.57 | N | 7.06 |
| | Found | C | 54.7 | H | 4.67 | N | 6.69 |
| Yield: 40% | | | M.p.: 238° C. | | | |

EXAMPLE 151

4-(3-(1-Imidazol-4-yl)propyloxy)phenyl-3-phenyl-2-propenone 5 mmol of 3-(1-triphenylmethyl-1H-imidazol-4-yl) propanol and 6 mmol of (4-hydroxyphenyl)-3-phenyl-2-propenone (prepared according to Shriner, R. L. et al., J. Am. Chem. Soc., 1930, 52, 2538) are treated as described in Example 56, but crystallized in the form of hydrogen oxalate from diethyl ether and ethanol.

| $C_{21}H_{20}N_2O_2 \cdot C_2H_2O_4 \cdot 0 \cdot 75H_2O$ (435.9) | | | | | | |
|---|---|---|---|---|---|---|
| CHN analysis | Calculated | C | 63.4 | H | 5.43 | N | 6.43 |
| | Found | C | 63.6 | H | 5.83 | N | 6.54 |
| Yield: 70% | | | M.p.: 170° C. | | | |

EXAMPLE 152

4-(3-(1H-Imidazol-4-yl)propyloxy)phenyl)heptanone 5 mmol of 3-(1-triphenylmethyl-1H-imidazol-4-yl) propanol and 6 mmol of (4-hydroxyphenyl)heptanone (prepared from heptanoic acid according to standard methods (Friedel-Crafts acylation)) are treated as described in Example 56.

| $C_{19}H_{26}N_2O_2 \cdot C_4H_4O_4 \cdot 0 \cdot 25H_2O$ (435.0) | | | | | | |
|---|---|---|---|---|---|---|
| CHN analysis | Calculated | C | 63.5 | H | 7.06 | N | 6.44 |
| | Found | C | 63.3 | H | 7.04 | N | 6.30 |
| Yield: 70% | | | M.p.: 119° C. | | | |

EXAMPLE 153

4-(3-(1H-Imidazol-4-yl)propyloxy)phenyl-2-phenylethanone 5 mmol of 3-(1-triphenylmethyl-1H-imidazol-4-yl) propanol and 6 mmol of (4-hydroxyphenyl)-2-phenylethanone are treated as described in Example 56, but crystallized in the form of hydrogen oxalate from diethyl ether and ethanol.

| $C_{20}H_{20}N_2O_2 \cdot C_2H_2O_4 \cdot 0 \cdot 75H_2O$ (423.9) | | | | | | |
|---|---|---|---|---|---|---|
| CHN analysis | Calculated | C | 62.3 | H | 5.59 | N | 6.61 |
| | Found | C | 62.3 | H | 5.45 | N | 6.48 |
| Yield: 65% | | | M.p.: 185° C. | | | |

EXAMPLE 154

4-[3-(3-Trifluoromethylphenylamino)propyl]-1H-imidazole oxalate

A mixture of 1 g (2.72 mmol) of 1-(triphenylmethyl)-4-[3-hydroxypropyl]imidazole, 0.55 g (4.07 mmol; 1.5 equivalents) of morpholine oxide and 1.36 g of powdered 4 Å molecular sieve in an anhydrous mixture of acetonitrile and dichloromethane (10:4) is stirred at room temperature under nitrogen. 0.047 g (0.135 mmol; 5 mol %) of tetrapropylammonium perruthenate (VII) is added in a single portion and the mixture is stirred at room temperature for 48 hours. The reaction mixture is filtered through silica gel (preloaded with ethyl acetate) and the filtrate is evaporated under reduced pressure. The oil obtained is purified by chromatography on a column of silica gel with diethyl ether as eluent to yield 3-(1-triphenylmethyl-4-imidazolyl) propionaldehyde.

0.5 g (1.36 mmol) of the above aldehyde is heated with 0.22 g (1.36 mmol) of 3-trifluoromethylaniline in 50 ml of anhydrous toluene at 50° C. for 30 minutes. The solvent is driven off under reduced pressure to leave 0.6 g (86%) of an oil, which is dissolved in methanol, cooled to 0° C. and then treated with 1.06 g (0.027 mol; 20 equivalents) of sodium borohydride added slowly at 0° C. The mixture is stirred at room temperature overnight, the solvent is then driven off under reduced pressure, 20 ml of water are added and the mixture is extracted with chloroform. The chloroform extracts are dried ($MgSO_4$) and the solvent is evaporated off under reduced pressure to leave an oil, which is purified by chromatography on a column of silica gel (eluent: diethyl ether) to yield 0.4 g of 1-triphenylmethyl-4-[3-(3-trifluoromethylphenylamino)propyl]imidazole in the form of a colourless oil. The latter (0.35 g; 6.85 mmol) in 8 ml of tetrahydrofuran and 12 ml of 2M HCl is heated at 80° C. for 5 hours. The tetrahydrofuran is evaporated off under reduced pressure and $Ph_3COH$ is extracted with diethyl ether. The aqueous layer is neutralized with potassium carbonate and the product is extracted into chloroform. The chloroform solution is dried and evaporated to yield a brown oil, which is purified by chromatography on a column of silica gel with an ethyl acetate/methanol (5:1) mixture as eluent. The oil obtained is dissolved in 4 ml of 2-propanol and treated with a solution of 1.5 equivalents of oxalic acid in 3 ml of 2-propanol, and the mixture is cooled for 4 hours. The precipitate which is formed on addition of diethyl ether is collected and washed with ether to yield the desired oxalate in the form of a white solid, m.p. 150–151° C.

| $C_{13}H_{14}F_3N_3 \cdot 1 \cdot 5C_2H_2O_4$ | | | | | | |
|---|---|---|---|---|---|---|
| CHN analysis | Calculated | C | 47.18 | H | 3.76 | N | 9.96 |
| | Found | C | 47.08 | H | 4.15 | N | 10.17 |

EXAMPLE 155

4-[3-(4-Ethanoylphenylamino)propyl]-1H-imidazole oxalate

A mixture of 4 g (0.029 mol) of 3-aminoacetophenone and 2.47 ml (0.044 mol; 1.5 equivalents) of ethylene glycol and a small amount of 4-toluenesulphonic acid in 60 ml of anhydrous benzene are heated to reflux with azeotropic removal of water for 4 hours. The solution is left to cool, washed successively with 20% aqueous sodium carbonate and water and then dried ($MgSO_4$). The solvent is evaporated off under reduced pressure to leave a yellow oil, which is purified by chromatography on a column of silica gel using a diethyl ether/petroleum ether (1:1) mixture as eluent, and then crystallized in hexane to yield 3-(2-methyl-1,3-dioxolan-2-yl)aniline, m.p. 75–77° C.

The latter (0.096 g; 1.64 mmol) is heated with 0.6 g (1.64 mmol) of 3-[1-(triphenylmethyl)-4-imidazolyl]- propionaldehyde in 50 ml of anhydrous toluene at 50° C. for 30 minutes. The solvent is removed under reduced pressure to leave an oil, which is reduced with 0.064 g (0.016 mol) of sodium borohydride in methanol as described for Example 154 to yield N-{3-[1-(triphenylmethyl)-4-imidazolyl]propyl}-3-(2-methyl-1,3-dioxolan-2-yl)aniline in the form of a colourless oil. The latter (0.5 g; 0.95 mmol) is heated with 12 ml of 2M HCl in 8 ml of tetrahydrofuran at 80° C. for 5 hours. The tetrahydrofuran is evaporated off under reduced pressure and Ph$_3$COH is extracted into diethyl ether. The aqueous layer is neutralized with potassium carbonate and the product is extracted into chloroform. The chloroform solution is dried and evaporated to yield a brown oil, which is purified by chromatography on a column of silica gel (eluent: ethyl acetate/methanol, 5:1), and then treated with oxalic acid in 2-propanol as described for Example 154 to yield the desired oxalate, m.p. 152–154° C., after recrystallization in ethanol.

$C_{14}H_{17}N_3O \cdot C_2H_2O_4 \cdot 0 \cdot 1H_2O$:

| CHN analysis | Calculated | C | 57.34 | H | 5.77 | N | 12.54 |
|---|---|---|---|---|---|---|---|
| | Found | C | 57.18 | H | 5.78 | N | 12.39 |

EXAMPLE 156

4-[3-(3-Ethylphenylamino)propyl]-1H-imidazole oxalate 0.4 g (1.10 mmol) of 3-(1-triphenylmethyl-4-imidazolyl)propionaldehyde is treated with 0.13 g (1.10 mmol) of 3-ethylaniline in anhydrous toluene, and then reduced as described for Example 154 to yield 1-triphenylmethyl-4-[3-(3-ethylphenylamino)propyl]-imidazole in the form of a colourless oil. The latter is deprotected with HCl in tetrahydrofuran, and the oil obtained is converted to oxalate as described for Example 154, to yield the product, m.p. 189–191° C. after recrystallization in a mixture of 2-propanol and diethyl ether.

$C_{14}H_{19}N_3 \cdot 1 \cdot 5C_2H_2O_4 \cdot 0 \cdot 4H_2O$:

| CHN analysis | Calculated | C | 54.95 | H | 6.18 | N | 11.13 |
|---|---|---|---|---|---|---|---|
| | Found | C | 55.03 | H | 5.80 | N | 10.77 |

EXAMPLE 157

4-[2-(3-Ethanoylphenylthio)ethyl]-1H-imidazole oxalate 0.223 g (1.53 mmol) of 3-ethanoylthiophenol is dissolved in 20 ml of anhydrous dimethyl formamide and cooled in ice to below 4° C. under a nitrogen atmosphere. 0.153 g (3.83 mmol) of sodium hydride is added in small portions at below 5° C. After 10 minutes, the mixture is warmed to room temperature. 0.128 g (0.76 mmol) of 4-(2-chloroethyl)-1H-imidazole hydrochloride and 10 mg of catalyst consisting of tetra-n-butylammonium iodide are added and the mixture is heated at 80° C. for 3 days. The solvent is removed under reduced pressure to yield a brown gum, which is dissolved in 50–60 ml of 10% HCl, washed 4 times with 40 ml of ether, alkalized with solid potassium carbonate to pH 7–8 and then extracted 3 times with 40 ml of dichloromethane. The combined extracts are evaporated, and the oil obtained is purified by chromatography on a column of silica gel with elution with an ethyl acetate/methanol (95:5) mixture and is then, after being extracted into cold 2-propanol, converted to the oxalate in ethanol to yield a white crystalline solid, m.p. 138–140° C.

$C_{13}H_{14}N_2OS \cdot 0 \cdot 95C_2H_2O_4 \cdot 0 \cdot 1C_3H_7OH$:

| CHN analysis | Calculated | C | 54.03 | H | 4.98 | N | 8.29 |
|---|---|---|---|---|---|---|---|
| | Found | C | 54.25 | H | 4.99 | N | 7.83 |

EXAMPLE 158

4-[3-(3-(1-Hydroxyiminoethyl)phenoxy)propyl]-1H-imidazole oxalate

A solution of 0.125 g (1.81 mmol) of hydroxylamine hydrochloride and 0.5 g (0.006 mol) of sodium acetate in 10 ml of water is stirred for 10 minutes, and a solution of 0.125 g (0.512 mmol) of 4-[3-(3-ethanoylphenoxy)propyl]-1H-imidazole in 3 ml of ethanol is then added slowly. The mixture is stirred at room temperature for 1 hour and then heated at 80° C. for 2 hours. After cooling, the solvent is removed under reduced pressure and the white residue obtained is extracted with chloroform. The chloroform is dried (MgSO$_4$) and then evaporated. The oil obtained is dissolved in 4 ml of 2-propanol and treated with 1.3 equivalents of oxalic acid in 3 ml of 2-propanol. The addition of diethyl ether yields the product, which is separated by filtration, washed with ether and recrystallized in a 2-propanol/diethyl ether mixture, m.p. 149–151° C.

$C_{14}H_{17}N_3O_2 \cdot C_2H_2O_4$:

| CHN analysis | Calculated | C | 55.01 | H | 5.45 | N | 12.03 |
|---|---|---|---|---|---|---|---|
| | Found | C | 54.87 | H | 5.01 | N | 12.16 |

EXAMPLE 159

4-[2-(3-Trifluoromethylphenylthio)propyl]-1H-imidazole oxalate 5.426 g (18.7 mmol) of 1-(N,N-dimethylsulphamoyl)-2-tert-butyldimethylsilylimidazole are dissolved in 100 ml of freshly distilled THF under nitrogen and cooled to −78° C., and a solution of n-butyl-lithium in hexane (2.5M; 15 ml; 37.5 mmol) is added dropwise over a period of 10 min. The mixture is stirred for 30 min at −78° C. The solution is warmed to 0° C. with rapid stirring, and a solution of 3.0 ml (2.49 g; 42.9 mmol) of propylene oxide in 20 ml of freshly distilled THF is added dropwise over a period of 15 min. The mixture is stirred for 18 hours with heating at 20° C., and the mixture is then hydrolysed by adding 100 ml of saturated NH$_4$Cl solution. The THF is removed under reduced pressure and the mixture obtained is extracted three times with 100 ml of dichloromethane. The organic layers are combined, dried (MgSO$_4$) and evaporated under reduced pressure to yield an oil, which is subjected to column chromatography with diethyl ether as eluent to yield 1-(N,N-dimethylsulphamoyl)-2-tert-butyldimethylsilyl-5-(2-hydroxypropyl)imidazole in the form of a viscous yellow oil.

The above oil (11.28 g; 32.5 mmol) is dissolved in 50 ml of anhydrous carbon tetrachloride, and 9.18 g (35.0 mmol) of anhydrous triphenylphosphine in 50 ml of anhydrous carbon tetrachloride are added. The mixture is stirred under a nitrogen atmosphere at 50° C. and then brought to reflux for 16 hours. The solvent is evaporated off in vacuo, and the solid obtained is subjected to column chromatography with dichloromethane on silica gel to yield 1-(N,N-dimethylsulphamoyl)-2-tert-butyldimethylsilyl-5-(2-chloropropyl)imidazole in the form of a pale yellow oil which solidifies, m.p. 51–53° C.

3-Trifluoromethylthiophenol (0.298 g; 1.67 mmol) is dissolved in 20 ml of anhydrous DMF and cooled to 0° C. under a nitrogen atmosphere, and NaH (60% dispersion in mineral oil; 0.0393 g; 1.638 mmol) is added in small portions. The reaction mixture is stirred at 0° C. for 15 min and then at 20° C. for a further 1.5 h, and 0.293 g (0.80 mmol) of 1-(N,N-dimethylsulphamoyl)-2-tert-butyldimethylsilyl-5-(2-chloropropyl) imidazole dissolved in 5 ml of DMF and 10 mg of n-Bu$_4$NI are added and the mixture is heated at 80° C. for 3 days. The solvent is driven off under reduced pressure to yield a brown oil, which is treated with 100 ml of water and extracted 3 times with 40 ml of dichloromethane. The extracts are dried (MgSO$_4$) and concentrated, and the oil obtained is subjected to column chromatography using 2:1 and 1:1 petroleum spirit/ethyl acetate, then dissolved in 10 ml of 2M HCl and heated at 100° C. under reflux for 3 hours. The reaction mixture is then alkalized by adding 10% NaOH (pH approximately 11) and is extracted 3 times with 40 ml of dichloromethane. The extracts are dried (MgSO$_4$) and evaporated to form a clear oil, which is subjected to column chromatography with ethyl acetate as eluent and converted to the oxalate of the desired product in 2-propanol, m.p. 166–168° C.

| $C_{13}H_{13}F_3N_2S \cdot C_2H_2O_4$: | | | | | | | |
|---|---|---|---|---|---|---|---|
| CHN analysis | Calculated | C | 47.87 | H | 4.02 | N | 7.44 |
| | Found | C | 47.43 | H | 4.04 | N | 7.22 |

EXAMPLE 160

4-[2-(4-Methylphenoxy)ethyl]-1H-imidazole oxalate (Similar to method A)

A mixture of 0.18 g (1.68 mmol) of p-cresol, 0.60 g (1.69 mmol) of 1-(triphenylmethyl)-4-(2-hydroxyethyl)imidazole and 0.44 g (1.69 mmol) of triphenylphosphine in 20 ml of anhydrous tetrahydrofuran is cooled and stirred for 10 minutes under nitrogen. 0.66 g (3.44 mmol) of diethyl azodicarboxylate, dissolved in 10 ml of freshly distilled THF, is added slowly to the reaction mixture, and stirring is continued at room temperature for 16 hours. After removal of the solvent in vacuo, column chromatography of the crude reaction mixture on silica gel (eluent: hexane/ethyl acetate, 2:1) yields 0.45 g (60%) of product in the form of a colourless oil. The latter is heated at 80° C. for 5 hours in 8 ml of THF and 1.3 equivalents of 2M hydrochloric acid. After cooling, the THF is driven off under reduced pressure and Ph$_3$COH is extracted with 3 30-ml portions of diethyl ether. The aqueous layer is neutralized with potassium carbonate and the product is extracted into 3 30-ml portions of chloroform. The combined chloroform layers are dried (MgSO$_4$) and evaporated under reduced pressure to yield an oil, which is treated with a propanolic solution of oxalic acid to yield the product, m.p. 188–189° C., which is dried in vacuo.

| $C_{12}H_{14}N_2O \cdot 0 \cdot 8C_2H_2O_4$: | | | | | | | |
|---|---|---|---|---|---|---|---|
| CHN analysis | Calculated | C | 59.56 | H | 5.73 | N | 10.21 |
| | Found | C | 59.80 | H | 5.77 | N | 10.17 |

EXAMPLE 161

4-[2-(4-Propionylphenoxy)ethyl]-1H-imidazole oxalate

In a manner similar to Example 160, 0.254 g (1.69 mmol) of 4-propionylphenol is converted to the abovementioned oxalate, m.p. 185–187° C.

| $C_{14}H_{16}N_2O_2 \cdot 0 \cdot 9C_2H_2O_4$: | | | | | | | |
|---|---|---|---|---|---|---|---|
| CHN analysis | Calculated | C | 58.33 | H | 5.52 | N | 8.61 |
| | Found | C | 58.30 | H | 5.45 | N | 8.55 |

EXAMPLE 162

4-[3-(4-sec-Butylphenoxy)propyl]-1H-imidazole oxalate

In a manner similar to Example 160, 0.6 g (1.63 mmol) of 1-(triphenylmethyl)-4-(3-hydroxypropyl)imidazole is treated with 0.245 g (1.63 mmol) of 4-sec-butylphenol to yield the abovementioned oxalate, m.p. 202–203° C.

| $C_{16}H_{22}N_2O \cdot 0 \cdot 8C_2H_2O_4$: | | | | | | | |
|---|---|---|---|---|---|---|---|
| CHN analysis | Calculated | C | 63.98 | H | 7.20 | N | 8.48 |
| | Found | C | 63.85 | H | 7.24 | N | 8.52 |

EXAMPLE 163

4-[3-(4-Ethylphenoxy)propyl]-1H-imidazole oxalate

In a manner similar to Example 160, 0.80 g (2.17 mmol) of 1-(triphenylmethyl)-4-(3-hydroxypropyl)imidazole is treated with 0.33 g (2.70 mmol) of 4-ethylphenol to yield the abovementioned oxalate, m.p. 199–200° C. after recrystallization in ethanol.

| $C_{14}H_{18}N_2O \cdot 0 \cdot 8C_2H_2O_4$: | | | | | | | |
|---|---|---|---|---|---|---|---|
| CHN analysis | Calculated | C | 61.97 | H | 6.53 | N | 9.27 |
| | Found | C | 62.16 | H | 6.39 | N | 9.38 |

EXAMPLE 164

4-[3-(4-Imidazol-1-ylphenoxy)propyl]-1H-imidazole trifluoroacetate

In a manner similar to Example 160, 0.5 g (1.36 mmol) of 1-(triphenylmethyl)-4-(3-hydroxypropyl)imidazole is treated with 0.27 g (1.70 mmol) of 4-(1-imidazolyl)phenol to yield the abovementioned compound in the form of the oxalate salt. The latter is impure, and it is hence subjected to preparative high pressure liquid chromatography on Kromasil C$_{18}$ using 0.1% trifluoacetic acid and 0.1% trifluoroacetic acid in methanol in a 4:1 ratio. The product obtained is the hydrated trifluoroacetate, m.p. 259° C. (decomposition).

| $C_{15}H_{16}N_4O \cdot 0 \cdot 6CF_3CO_2H \cdot 2 \cdot 1H_2O$: | | | | | | | | |
|---|---|---|---|---|---|---|---|---|
| CHN analysis | Calculated | C | 51.95 | H | 5.60 | N | 14.96 | |
| | Found | C | 51.92 | H | 5.66 | N | 14.76 | |

EXAMPLE 165

4-[3-(4-(N,N-Dimethylsulphamoyl)phenoxy)propyl]-1H-imidazole oxalate

In a manner similar to Example 160, 0.60 g (1.63 mmol) of 1-(triphenylmethyl)-4-(3-hydroxypropyl)imidazole is treated with 0.39 g (1.95 mmol) of 4-(N,N-dimethylsulphamoyl)phenol (m.p. 94–96° C.; Steinkopf, J. prakt. Chem. [2] 1927, 117, 59) to yield the abovementioned oxalate, m.p. 178–180° C.

| $C_{14}H_{19}N_3O_3S \cdot 0 \cdot 85C_2H_2O_4$: | | | | | | | | |
|---|---|---|---|---|---|---|---|---|
| CHN analysis | Calculated | C | 48.86 | H | 5.41 | N | 10.89 | |
| | Found | C | 48.81 | H | 5.67 | N | 10.81 | |

EXAMPLE 166

4-[3-(4-Thiomethylphenoxy)propyl]-1H-imidazole oxalate

In a manner similar to Example 160, 0.50 g (1.35 mmol) of 1-(triphenylmethyl)-4-(3-hydroxypropyl)imidazole is treated with 0.19 g (1.35 mmol) of 4-thiomethylphenol to yield the abovementioned oxalate, which has an m.p. of 202–204° C. after recrystallization in ethanol.

| $C_{13}H_{16}N_2OS \cdot C_2H_2O_4 \cdot 0 \cdot 1H_2O$: | | | | | | | | | |
|---|---|---|---|---|---|---|---|---|---|
| CHNS analysis | Calculated | C | 52.96 | H | 5.39 | N | 8.23 | S | 9.42 |
| | Found | C | 52.73 | H | 5.38 | N | 8.12 | S | 9.66 |

EXAMPLE 167

4-[3-(4-Thiobenzylphenoxy)propyl]-1H-imidazole hydrochloride

In a manner similar to Example 160, 0.70 g (1.9 mmol) of 1-(triphenylmethyl)-4-(3-hydroxypropyl)imidazole is treated with 0.41 g (1.9 mmol) of 4-thiobenzylphenol and then deprotected with 2M HCl in tetrahydrofuran. After removal of the solvent, a solid remains, which is washed with diethyl ether and crystallized in 2-propanol and diethyl ether to yield the abovementioned hydrochloride, which has an m.p. of 166–168° C.

| $C_{19}H_{20}N_2OS \cdot HCl$: | | | | | | | | |
|---|---|---|---|---|---|---|---|---|
| CHN analysis | Calculated | C | 63.32 | H | 5.87 | N | 7.77 | |
| | Found | C | 63.73 | H | 5.77 | N | 8.13 | |

EXAMPLE 168

4-[3-(3-Acetylphenylthio)propyl]-1H-imidazole oxalate
(Similar to method C)

3-Acetylthiophenol (0.256 g; 1.68 mmol) is dissolved in 20 ml of anhydrous dimethylformamide and cooled to below 4° C. under a nitrogen atmosphere, and 0.067 g (1.68 mmol) of sodium hydride is added in small portions at below 4° C. The mixture is stirred at 4° C. for 15 min and then at 20° C. for 1.5 h. 2-tert-Butyldimethylsilyl-5-(3-chloropropyl)-1-(N,N-dimethylsulphamoyl)imidazole (Vollinga, R. C., Menge, W. M. P. B. and Timmerman, H. Rec. trav. chim. Pays-Bas. 1993, 112, 123–125) (0.283 g; 0.84 mmol) in 10 ml of dimethylformamide and 10 mg of tetra-n-butylammonium iodide as catalyst are added, and the mixture is heated at 80° C. for 3 days. The solvent is removed under reduced pressure, and the reaction mixture is halted with 100 ml of water and extracted 3 times with 40 ml of dichloromethane; the extracts are dried ($MgSO_4$) and concentrated to an oil, which is purified by column chromatography by using a petroleum spirit/ethyl acetate (60:40) mixture to yield 1-(N,N-dimethylsulphamoyl)-4-[3-(3-acetylphenylthio)propyl]imidazole. The latter is heated in 15 ml of 2M HCl under reflux for 5 h. The reaction is left to cool, then alkalized with 10% aqueous sodium hydroxide to pH 10 and extracted 3 times with 50 ml of dichloromethane. The extracts are dried ($MgSO_4$) and concentrated to an oil, which is purified by column chromatography with a 95:5 ethyl acetate/methanol mixture. The oily product is converted to the oxalate in ethanol to yield a white crystalline solid, m.p. 122–124° C.

| $C_{14}H_{16}N_2OS \cdot 1 \cdot 2C_2H_2O_4$: | | | | | | | | |
|---|---|---|---|---|---|---|---|---|
| CHN analysis | Calculated | C | 54.14 | H | 5.10 | N | 7.79 | |
| | Found | C | 54.57 | H | 5.21 | N | 7.41 | |

EXAMPLE 169

4-[3-(4-Ethylphenylamino)propyl]-1H-imidazole oxalate

In a manner similar to Example 154, 4-ethyl-aniline is converted to the abovementioned compound, which has an m.p. of 154–156° C. after crystallization in ethanol.

| $C_{14}H_{19}N_3 \cdot 1 \cdot 85C_2H_2O_4$: | | | | | | | | |
|---|---|---|---|---|---|---|---|---|
| CHN analysis | Calculated | C | 53.70 | H | 5.74 | N | 10.61 | |
| | Found | C | 53.74 | H | 5.98 | N | 10.56 | |

EXAMPLE 170

4-[3-(4-Chlorophenylamino)propyl]-1H-imidazole oxalate

In a manner similar to Example 154, 4-chloroaniline is converted to the abovementioned compound, which has an m.p. of 130–134° C. after crystallization in ethanol.

| $C_{12}H_{14}ClN_3 \cdot 2 \cdot 2C_2H_2O_4$: | | | | | | | | |
|---|---|---|---|---|---|---|---|---|
| CHN analysis | Calculated | C | 45.41 | H | 4.28 | N | 9.69 | |
| | Found | C | 45.48 | H | 4.40 | N | 9.80 | |

EXAMPLE 171

3-(1H-Imidazol-4-yl)propyl 4-(2-(trimethylsilyl)-1-ethynyl)phenyl ether 5 mmol of 4-(3-hydroxypropyl)-1H-imidazole-1-carboxylic acid tert-butyl ester and 5 mmol of 4-(2-

(trimethylsilyl)-1-ethynyl)phenol (for the preparation see the literature mentioned in Example 122) are treated as described in Example 122.

$C_{17}H_{22}N_2OSi \cdot C_4H_4O_4 \cdot 0.75H_2O$ (428.1)
CHN analysis  Calculated  C  58.9  H  6.48  N  6.54
              Found       C  58.7  H  6.04  N  6.89
Yield: 30%                           M.p.: 126° C.

EXAMPLE 172

3-(1H-Imidazol-4-yl)propyl 4-(1-propynyl)phenyl ether 5 mmol of 4-(3-hydroxypropyl-1H-imidazole-1-carboxylic acid tert-butyl ester and 5 mmol of 4-(1-propynyl)phenol are treated as described in Example 122.

$C_{15}H_{16}N_2O \cdot C_4H_4O_4 \cdot 0.5H_2O$ (365.4)
CHN analysis  Calculated  C  62.5  H  5.79  N  7.67
              Found       C  62.3  H  5.83  N  7.53
Yield: 87%                           M.p.: 137° C.

EXAMPLE 173

3-(1H-Imidazol-4-yl)propyl-4-isopropylphenyl ether 5 mmol of 3-(1-triphenylmethyl-1H-imidazol-4-yl) propanol and 6 mmol of 4-isopropylphenol are treated as described in Example 56.

$C_{15}H_{20}N_2O_2 \cdot C_4H_4O_4 \cdot 0.25H_2O$ (364.9)
CHN analysis  Calculated  C  62.5  H  6.77  N  7.68
              Found       C  62.5  H  6.70  N  7.79
Yield: 70%                           M.p.: 110° C.

EXAMPLE 174

3-(1H-Imidazol-4-yl)propyl methyl ether 2.5 mmol of 3-(1-triphenylmethyl-1H-imidazol-4-yl)propyl.HCl chloride (prepared from 3-(1-triphenylmethyl-1H-imidazol-4-yl)propanol with thionyl chloride in THF) are added to a solution of 22 mmol of sodium in 50 ml of methanol. The reaction mixture is then brought to reflux for 100 h and thereafter purified as described in Example 5. The title compound is crystallized in the form of the hydrogen oxalate from ethanol and diethyl ether.

$C_7H_{12}N_2O \cdot C_2H_2O_4$ (230.7)
CHN analysis  Calculated  C  47.0  H  6.13  N  12.2
              Found       C  47.1  H  6.01  N  12.1
Yield: 40%                           M.p.: 139° C.

EXAMPLE 175

Ethyl 3-(1H-imidazol-4-yl)propyl ether 5 mmol of 3-(1-triphenylmethyl-1H-imidazol-4-yl)propanol and 5 mmol of bromoethane are treated as described in Example 5. The title compound is crystallized in the form of hydrogen oxalate from ethanol and diethyl ether.

$C_8H_{14}N_2O \cdot 0.75C_2H_2O_4$ (221.7)
CHN analysis  Calculated  C  51.5  H  7.05  N  12.6
              Found       C  51.4  H  6.85  N  12.7
Yield: 20%                           M.p.: 167° C.

EXAMPLE 176

3-(1H-Imidazol-4-yl)propyl propyl ether 5 mmol of 3-(1-triphenylmethyl-1H-imidazol-4-yl) propanol and 5 mmol of bromopropane are treated as described in Example 5. The title compound is crystallized in the form of hydrogen oxalate from ethanol and diethyl ether.

$C_9H_{16}N_2O \cdot 0.75C_2H_2O_4$ (235.8)
CHN analysis  Calculated  C  53.5  H  7.48  N  11.9
              Found       C  53.1  H  7.26  N  11.8
Yield: 20%                           M.p.: 169° C.

EXAMPLE 177

Cyclopropyl 3-(1H-imidazol-4-yl)propyl ether 5 mmol of 3-(1-triphenylmethyl-1H-imidazol-4-yl) propyl.HCl chloride (see Example 174) and 30 mmol of sodium cyclopropanolate (prepared with sodium in cyclopropanol) in 20 ml of cyclopropanol are treated as described in Example 174. The title compound is crystallized in the form of hydrogen oxalate from ethanol and diethyl ether.

$C_9H_{14}N_2O \cdot C_2H_2O_4$ (256.3)
CHN analysis  Calculated  C  51.6  H  6.29  N  10.9
              Found       C  51.3  H  5.98  N  10.7
Yield: 10%                           M.p.: 158° C.

EXAMPLE 178

Cyclopropylmethyl 3-(1H-imidazol-4-yl)propyl ether 5 mmol of 3-(1-triphenylmethyl-1H-imidazol-4-yl)propanol and 10 mmol of cyclopropylmethylsodium chloride are treated as described in Example 5. The title compound is crystallized in the form of hydrogen maleate from ethanol and diethyl ether.

$C_{10}H_{16}N_2O \cdot C_4H_4O_4$ (296.3)
CHN analysis  Calculated  C  56.7  H  6.80  N  9.45
              Found       C  56.7  H  6.70  N  9.38
Yield: 10%                           M.p.: 85° C.

EXAMPLE 179

1-(1H-Imidazol-4-yl)-6-phenyl hexane 5 mmol of 3-(1-triphenylmethyl-1H-imidazol-4-yl)propanal (prepared according to standard methods (Swern oxidation) with 3-(1-triphenylmethyl-1H-imidazol-4-yl) propanol and oxalyl chloride in DMSO at −45° C.) and 5 mmol of 3-phenylpropyltriphenylphosphonium bromide (prepared from triphenylphosphine and 3-phenylpropyl bromide in toluene under reflux for 12 h) are treated as described in Example 51. The 1-(1H-imidazol-4-yl)-6-phenyl-3-hexene is hydrogenated as described in Example 52. The title compound is crystallized in the form of hydrogen oxalate in ethanol and diethyl ether.

$C_{15}H_{20}N_2 \cdot C_2H_2O_4$ (318.4)
| CHN analysis | Calculated | C | 64.1 | H | 6.97 | N | 8.80 |
|---|---|---|---|---|---|---|---|
| | Found | C | 64.1 | H | 7.19 | N | 9.09 |

Yield: 25%   M.p.: 175° C.

EXAMPLE 180

N-[3,5-Di(trifluoromethyl)phenyl]-3-(1H-imidazol-4-yl)propyl carbamate 5 mmol of 3,5-di(trifluoromethyl)benzoic acid, 5 mmol of triethylamine and 5 mmol of diphenyl phosphorazidate are treated as described in Example 110. $C_{15}H_{13}N_3O_2F_6 \cdot C_2H_2O_4$ (471.1) Yield: 16% M.p.: 215° C. (decomposition) High resolution mass spectrum, MAT 711/19.944 instrument, peak matching method (80 eV, 0.8 mA), temperature 150° C.:

Theoretical: 381.091210

Found: 381.091180

EXAMPLE 181

N-(1-tert-Butyl-2-phenyl)ethyl-3-(1H-imidazol-4-yl)propyl carbamate 5 mmol of 2-tert-butyl-3-phenylpropionic acid, 5 mmol of triethylamine and 5 mmol of diphenyl phosphorazidate are treated as described in Example 110.

$C_{19}H_{27}N_3O_2 \cdot C_2H_2O_4 \cdot 0 \cdot 25H_2O$ (424.0)
| CHN analysis | Calculated | C | 59.5 | H | 7.01 | N | 9.91 |
|---|---|---|---|---|---|---|---|
| | Found | C | 59.3 | H | 6.71 | N | 9.82 |

Yield: 15%   M.p.: 158° C.

EXAMPLE 182

N-(1-Ethylpropyl)-3-(1H-imidazol-4-yl)propyl carbamate 5 mmol of 2-ethylbutyric acid, 5 mmol of triethylamine and 5 mmol of diphenyl phosphorazidate are treated as described in Example 110. This title compound is crystallized in the form of hydrogen maleate from diethyl ether and ethanol.

$C_{12}H_{21}N_3O_2 \cdot C_4H_4O_4$ (355.4)
| CHN analysis | Calculated | C | 54.1 | H | 7.09 | N | 11.8 |
|---|---|---|---|---|---|---|---|
| | Found | C | 53.7 | H | 6.92 | N | 11.6 |

Yield: 22%   M.p.: 108° C.

EXAMPLE 183

1-(1H-Inidazol-4-yl)-6-phenyl-3-hexene 5 mmol of 3-(1-triphenylmethyl-1H-imidazol-4-yl) propanal (prepared according to standard methods (Swern oxidation) with 3-(1-triphenylmethyl-1H-imidazol-4-yl) propanol and oxalyl chloride in DMSO at −45° C.; see Examples 179 and 154) and 5 mmol of 3-phenylpropyltriphenylphosphonium bromide (see Example 179) are treated as described in Example 51. The title compound is crystallized in the form of hydrogen oxalate in ethanol and diethyl ether.

$C_{15}H_{18}N_2 \cdot 0 \cdot 75C_2H_2O_4$ (293.9)
| CHN analysis | Calculated | C | 67.4 | H | 6.69 | N | 9.53 |
|---|---|---|---|---|---|---|---|
| | Found | C | 67.3 | H | 6.92 | N | 9.69 |

Yield: 30%   M.p.: 140° C.

PHARMACOLOGICAL STUDY

Antagonist Compounds

The interaction of the compounds with the $H_3$ receptor is demonstrated in vitro by measuring the release of [$^3$H] histamine synthesized from [$^3$H]histidine by synaptosomes of rat cerebral cortex (Garbarg et al., J. Pharmacol. Exp. Ther. 1992, 263: 304).

The $H_3$ antagonist power of the compounds is evaluated by the progressive reversal of the inhibition of the release of [$^3$H]histamine by (R)- -methylhistamine, a selective $H_3$ agonist (Arrang et al., Nature, 1987, 327: 117–123).

The antagonist effects of the compounds in vivo are evaluated by measuring the changes in the levels of cerebral tele-methylhistamine in mice (Garbarg et al., J. Neurochem. 1989, 53: 1724). After a variable lapse of time following administration of the compound, the effect of an $H_3$ antagonist is demonstrated by the rise in the level of cerebral tele-methylhistamine which it induces. Results are collated in Tables II and III below:

TABLE II

APPARENT DISSOCIATION CONSTANTS (Ki) OF VARIOUS DERIVATIVES OF THE INVENTION AS HISTAMINE ANTAGONISTS AT THE $H_3$ RECEPTORS.

| Example No. | Ki (nM) |
|---|---|
| 21 | 45 |
| 64 | 16 |
| 56 | 22 |
| 30 | 8 |
| 61 | 0.5 |
| 93 | 25 |
| 115 | 44 |
| 149 | 44 |
| 166 | 3 |

TABLE III

EFFECTS OF ANTAGONIST COMPOUNDS ON THE LEVEL OF CEREBRAL TELE-METHYLHISTAMINE.

| $H_3$ antagonists | Change in the level of cerebral tele-methylhistamine (relative to controls) |
|---|---|
| 81 | +72% |
| 21 | +79% |
| 67 | +73% |
| 78 | +68% |
| 30 | +67% |
| 39 | +84% |

TABLE III-continued

EFFECTS OF ANTAGONIST COMPOUNDS ON THE
LEVEL OF CEREBRAL TELE-METHYLHISTAMINE.

| $H_3$ antagonists | Change in the level of cerebral tele-methylhistamine (relative to controls) |
|---|---|
| 112 | +98% |
| 140 | +84% |
| 160 | +95% |

These various compounds were administered at a dose of 10 mg/kg p.o., and the mice sacrificed 90 min later. The reference compound was thioperamide which, under the same conditions, induces changes of +75% to +100% on average.

This property of $H_3$ antagonists which are active systemically makes the compounds of the invention useful derivatives in human and veterinary medicine. Their therapeutic applications relate, in particular, to the central nervous system (including as psychostimulants). The compounds which are histamine $H_3$ receptor antagonists of formula Ia or Ib are advantageously used as active principle of medicinal products having psychotropic and wakefulness-, attention-, memory- and mood-activating actions, in the treatment of conditions such as Alzheimer's disease and other cognitive disorders of the elderly, and depressive or even simply asthenic states. Their nootropic effects may be turned to good account in order to stimulate alertness or the learning capacity of healthy subjects. Their positive effects on the regulation of the activity of the balance centres will be turned to good account in the treatment of vertigo. They may also be used as active principle of medicinal products intended for the treatment of balancing disorders and vertigo, in particular Ménière's disease, especially in the elderly. They may be usefully combined with treatments with other psychiatric agents such as neuroleptics in order to increase their activity and decrease their side-effects. The therapeutic applications also relate to the peripheral organs, in particular as stimulants of secretion and of gastrointestinal motor function.

Hence the present invention also relates to pharmaceutical compositions which contain as active principle a therapeutically effective amount of one of the antagonist compounds of formula Ia or Ib.

The pharmaceutical composition according to the invention is administrable to man via the oral, perlingual, nasal, dermal, transdermal, ophthalmic, vaginal, percutaneous, topical, rectal and parenteral routes, the active principle being combined with a therapeutically appropriate excipient or vehicle.

Each single dose advantageously contains 0.03 to 3 mg/kg.

The subject of the invention is also the use of the derivatives according to the invention for the preparation of $H_3$ antagonist medicinal products according to the above-mentioned procedures.

Agonist or Partial Agonist Compounds

The interaction of the compounds with the $H_3$ receptor is demonstrated in vitro by measuring the release of [$^3$H] histamine synthesized from [$^3$H]histidine by the synaptosomes of rat cerebral cortex.

The $H_3$ agonist effect of the compounds is demonstrated by the inhibition of release of [$^3$H]histamine which they induce reversibly in the presence of a $H_3$ antagonist such as thioperamide. The partial agonist effect of the compounds is evaluated by comparison of the maximum inhibition which they induce relative to the maximum inhibition induced by exogenous histamine or [R]-α-methylhistamine; the ratio of these two values giving the intrinsic activity of the compound with respect to the system.

The effect of a partial agonist in vivo is characterized by the fact that the maximum reduction in the level of tele-methylhistamine which it induces at high dose is smaller than the reduction induced by a reference $H_3$ agonist.

However, for some partial agonist compounds displaying a low or even moderate intrinsic activity ($\leq 10\%$ of that of histamine), the in vitro test does not enable the agonist effect to be demonstrated readily. In contrast, we have discovered that measurement of the activity of the cerebral histaminic neurons in vivo, reflected by the level of tele-methylhistamine, a characteristic metabolite of released histamine, constitutes a more sensitive test of agonist activity. In effect, compounds displaying an intrinsic activity $\leq 25\%$ in vitro cause, in vivo, a maximum or virtually maximum fall in the level of the tele-methylhistamine. Another sensitive test of $H_3$ agonist activity, in this instance in relation to peripheral organs, consists in measuring the plasma extravasation induced in rats under the influence of capsaicin (90 μg/kg i.v.) and determined by measuring the tissue level of Evans blue, a dye administered at the same time as capsaicin, namely 5 min before infusion and sacrifice (Saria et al., Naunyn-Schmiedeberg's Arch. Pharmacol. 1983, 324: 212). Thus, in these two tests, the compound of Example 2 induces a response akin to that of (R)-α-methylhistamine, while, in vitro, its intrinsic agonist activity is in the region of 20% and it hence behaves essentially as an antagonist.

The results are collated in Tables IV and V below:

TABLE IV

50% EFFECTIVE CONCENTRATIONS ($EC_{50}$)
OF PARTIAL AGONISTS

| Example No. | $EC_{50}$ (nM) | Intrinsic activity |
|---|---|---|
| 8 | 100 | 40% |
| 5 | 130 | 20% |
| 2 | 100 | 20% |

TABLE V

EFFECTS OF PARTIAL AGONIST COMPOUNDS ON THE LEVEL OF
CEREBRAL TELE-METHYLHISTAMINE

| $H_3$ agonists | Change in the level of cerebral tele-methylhistamine (relative to controls) |
|---|---|
| 8 | −41% |
| 5 | −52% |
| 2 | −30% |
| 111 | −34% |
| 157 | −38% |

These various compounds were administered at a dose of 10 mg/kg p.o. and the mice sacrificed 90 min later. The reference compound was Imetit which, under the same conditions, induces changes of −45% to −60% on average.

This property of $H_3$ agonists which are active systemically makes the compounds of the invention useful derivatives in human and veterinary medicine.

$H_3$ receptor agonists and partial agonists, through their cerebral effects, mainly exert sedative, tranquillizing, antistress and analgesic activity, indicating their use as mild sedative psychotropics, in particular in various psychosomatic disorders.

H₃ agonists and partial agonists are also indicated in the treatment of migraine states and other headaches.

Through their peripheral effects, H₃ receptor agonists and partial agonists will be mainly indicated in the treatment of respiratory, allergic or inflammatory conditions (asthma, bronchitis, rhinitis, tracheitis, and the like), cardiac conditions (myocardial dysfunction and infarction), gastrointestinal conditions as a result of their antisecretory and anti-inflammatory actions (gastric and duodenal ulcers, ulcerative colitis, Crohn's disease, irritable bowel, faecal incontinence, and the like), conditions of the urogenital system (cystitis, metritis, premenstrual syndrome, prostatic inflammations, urinary incontinence, genital disorders) and conditions of the cutaneous system (urticaria, itching). The anti-inflammatory and analgesic effect may usefully be turned to good account in the treatment of arthritis and other rheumatic conditions, conjunctivitis and other ocular inflammations, and sialorrhoea.

Compounds which are histamine H₃ receptor agonists or partial agonists are advantageously used as active principle of medicinal products, in particular having mild sedative, antisecretory, anti-inflammatory, sleep-regulating and anti-convulsant effects, regulatory effects on hypothalamohypophyseal secretion, anti-depressant effects, modulatory effects on cerebral circulation, modulatory effects on the immune system, and anti-allergic and antimigraine effects.

Hence the present invention also relates to pharmaceutical compositions which contain as active principle a therapeutically effective amount of one of the agonist or partial agonist compounds of formula (Ib).

The pharmaceutical composition according to the invention is administrable to man via the oral, perlingual, dermal, transdermal, ophthalmic, vaginal, percutaneous, topical, nasal, rectal and parenteral routes, the active principle being combined with a therapeutically appropriate excipient or vehicle.

The agonist or partial agonist compounds of the present invention are active at single doses of between 0.1 and 10 mg/kg via the oral route in rodents, corresponding to doses of between 0.03 and 3 mg/kg in man. For local applications, for example in the form of ointments or eyewashes, the active concentrations will be between $10^{-8}$M and $10^{-5}$M.

The subject of the invention is also the use of the derivatives according to the invention for the preparation of H³ agonist medicinal products according to the abovementioned procedures.

What is claimed is:

1. A compound selected from the group consisting of

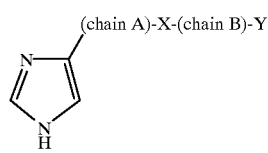
and

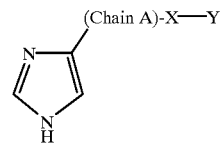

wherein A is selected from the group consisting of alkylene of 1 to 8 carbon atoms, alkenylene of 2 to 8 carbon atoms, alkynylene of 2 to 4 carbon atoms, wherein X is —OCONH—, —OCON(alkyl)-, —OCO—, —O—, —S—, —CO—, and amine;

B is selected from the group consisting of optionally unsaturated alkylene of 1 to 8 carbon atoms and —(CH₂)ₙ (heteroatom) where the heteroatom is sulfur or oxygen, n is an integer of 1 to 5;

Y is selected from the group consisting of a) phenyl substituted with at least one member of the group consisting of —OCF₃, —CHO, —SO₂N(alkyl)₂, —S(alkyl), —SCH₂(phenyl), alkene, alkyne optionally substituted with a trialkylsilyl, —O(aryl), —CH₂CN, a ketone, an aldehyde, a sulphono, an acetal, —OH, —CH=CH—CHO, —C(alkyl)=N—OH, —C(alkyl)=N—OH, —C(alkyl)=N—O(alkyl), —CH—NOH, —CH=NO(alkyl), —C(alkyl)—NH—NH—CONH₂, —O-alkyl, —OCH₂(phenyl), —C(cycloalkyl)=NOH or —C(cycloalkyl)=N—O(alkyl)- heterocycle optionally substituted; b) phenyl ring fused in a non-aromatic carbocycle or an heterocycle bearing a keto function; c) alkynyl or alkenyl of 2 to 8 carbon atoms substituted with phenyl, optionally substituted diphenyl alkyl ketone or a phenylcycloalkyl ketone; d) optionally substituted benzophenone; e) optionally substituted alkyl or cycloalkyl phenyl alcohol; f) alkene; g) phenylcycloalkyl; h) polycyclic selected from the group consisting of fluorenyl, polyhydronaphthyl and indanyl; i) phenol; j) ketone; k) diphenyl; l) phenoxyphenyl and m) benzyloxyphenyl, with the exception of the 4-[2-(4-acetylphenoxy)ethyl]-1H-imidazol]- and 4-[2-(4-benzoylphenoxy)ethyl]-1H-imidazole or their pharmaceutically acceptable salts, their hydrates, their hydrated salts, the polymorphic crystalline structures and the tautomeric forms of those compounds; and their optical isomers, racemic mixtures of said isomers and the corresponding diastereoisomers with the exception of the 4-[2-(4-acetylphenoxy)ethyl]-1H-imidazol]- and 4-[2-(4-benzoylphenoxy)ethyl]-1H-imidazol.

2. A compound of claim 1 wherein X is selected from the group consisting of —OCONH—, —OCON(alkyl)-, —OCO—, —O—, —S—, —CH₂— and —CO—; and Y is selected from the group consisting of a) phenyl substituted with at least one member of the group consisting of —OCF₃, —CHO, —SO₂N(alkyl)₂, —S(alkyl), alkene, —CH₂—CN, a ketone, halogen, aldehyde, —OH, —CH=NOH, —O(phenyl), —OCH₂(phenyl), —C(cycloalkyl)=N—OH, —C(cycloalkyl)=N—OH, —C(cycloalkyl)=N—(alkyl), —C(alkyl)=NOH, —C(alkyl)=NOalkyl and —CH=CHCHO; b) alkylyne of 1 to 8 carbon atoms; c) alkyl substituted with at least one member of the group consisting of phenyl optionally unsubstituted; d) phenyl alkyl ketone or phenyl cycloalkyl ketone; e) optionally substituted benzophenone; f) optionally substituted alkylphenyl or cyclic phenyl alcohol; g) alkene; h)phenylcycloalkyl; i) polycyclic selected from the group consisting of fluorenyl, polyhydronaphthyl and indanyl j) phenol; k) diphenyl; l) phenoxyphenyl; and m) benzyloxyphenyl.

3. A compound of claim 1 where A is alkyl of 1 to 5 carbon atoms or —(CH$_2$)$_n$— and n is an integer from 1 to 5.

4. A compound of claim 1 where Y is alkylene of 1 to 5 carbon atoms.

5. A compound according to claim 1 wherein Y is selected from the group consisting of a) phenyl substituted with at least one member of the group consisting of —OCF$_3$, —CHO, —SO$_2$N(alkyl)$_2$, halogen, —S(alkyl), —S(aryl), —SCH$_2$(phenyl)alkene, alkyne optionally substituted with a trialkylsilyl, —O(aryl), —CH$_2$CN, an aldehyde, a sulphone, an acetal, —OH, —CH=CH—CHO, —C(alkyl)=N—OH, —C(alkyl)=N—O(alkyl), —CH$_2$—NOH, —CH—NO(alkyl), —C(alkyl)=NH—NH—CONH$_2$, —O-alkyl, —OCH$_2$(phenyl), —C(cycloalkyl)=NOH, —C(cycloalkyl)=N—O(alkyl) and an optionally substituted heterocycle, b) phenyl ring fused to a non-aromatic carbocycle; c) an alkyne of 1 to 8 carbon atoms; d) alkyl substituted with phenyl unsubstituted or substituted; e) cyclic phenyl alcohol optionally substituted; f) alkene; g) phenyl cycloalkyl; h) a polycyclic selected from the group consisting of fluorenyl, indanyl, and polyhydronaphthyl; i) phenol; j) a keto derivative; k) diphenyl; l) phenoxy-phenyl and m) benzyloxyphenyl.

6. A compound of claim 1 wherein Y is selected from the group consisting of phenyl with at least one keto substituent; phenyl ring fused to a heterocycle bearing a keto function; phenyl alkyl or phenyl cycloalkyl, optionally substituted benzophenone and a ketone.

7. A compound of claim 6 wherein Y is selected from the group consisting of a ketone substituted with an optionally substituted alkyl and a ketone substituted with an optionally substituted aryl.

8. A compound of claim 6 wherein the keto substitutent Y is selected from the group consistinq of aliphatic ketone of 1 to 8 carbon atoms, a cycloalkyl ketone, an aryl alkyl ketone, aryl alkenyl ketone in which the aryl group is optionally substituted and a heteroaryl ketone.

9. A compound of claim 8 wherein the aliphatic ketone bears a hydroxyl.

10. A compound of claim 8 wherein the heteroaryl ketone is a monocyclic heteroaryl.

11. A compound of claim 8 wherein the keto substitutent Y is a cycloalkylketone.

12. A compound of claim 1 wherein Y is mono- or polysubstituted phenyl.

13. A compound of claim 1 wherein the acetal substituent is an aliphatic acetal of 1 to 8 carbon atoms unsubstituted or substituted with hydroxyl.

14. A compound of claim 12 wherein the heterocycle substituent is selected from oxadiazole and imidazole.

15. A compound of claim 12 wherein the phenyl substituent is selected from the group consisting of —CHO, —CH=CH—CHO, an aldehyde, —C(alkyl)=N—OH, —C(alkyl)—NO(alkyl), —CH=NOH, —CH—NO(alkyl)-, —C(alkyl)=NH—NH—CONH$_2$, —C(cycloalkyl)=N—OH and —C(cycloalkyl)=N—O(alkyl).

16. A compound of claim 12 wherein Y is phenyl substituted with a member selected from the group consisting of OCF$_3$, —S(alkyl), —S(aryl), —SCH$_2$(phenyl), —O(aryl), —O(alkyl), and —OCH$_2$(phenyl).

17. A compound of claim 16 wherein the phenyl substitutent is an alcohol.

18. A compound of claim 12 wherein the phenyl is substituted with a member selected from the group consisting of alkene and alkyne optionally substituted with trialkylsilyl.

19. A compound of claim 1 wherein Y is alkene or alkyne.

20. A compound of claim 1 wherein Y is optionally substituted alkyl phenyl alcohol or cycloalkyl phenyl alcohol.

21. A compound of claim 1 wherein Y is a phenyl cycloalkyl.

22. A compound of claim 1 wherein A is —(CH$_2$)$_3$—.

23. A compound of claim 22 of formula (Ia) wherein B is —(CH$_2$)$_2$—.

24. A compound of claim 1 selected from the group consisting of
3-(1H-Imidazol-4-yl)propyl N-(diphenylmethyl)carbamate,
3-(H-Imidazol-4-yl)propyl N-(2,2-diphenylethyl)carbamate,
2-(1H-Imidazol-4-yl)ethyl N-(2,2-dipehnylethyl)carbamate,
4-[3-(3-(Trifluoromethyoxy)phenoxy)propyl]-1H-imidazole,
4-[3-(3-Propanoylphenoxy)propyl]-1H-imidazole,
4-[3-(3-(1-Hydroxypropyl)phenoxy)propyl]-1H-imidazole,
4-[3-(5-Indanyloxy)propyl]-1H-imidazole,
4-[3-(3-(N,-N-Dimethylsulphonamido)phenoxy)propyl]-1H-imidazole,
4-[3-(3-Hydroxyphenoxy)propyl]-1H-imidazole,
4-{3-[3-(2-Penten-3-yl)phenoxy]propyl}-1H-imidazole,
4-[3-(4-Cyanomethylphenoxy)propyl]-1H-imdazole,
4-[3-(4-Phenoxyphenoxy)propyl]-1H-imidazole,
3-(1H-Imidazol-4-yl)propyl-N-trans-(2-phenylcyclopropyl)carbamate,
3-(1H-Imidazol-4-yl)propyl-N-(2-phenylpropyl)carbamate,
N-Fluoren-9-yl 3-(1H-imidazol-4-yl)propyl-carbamate,
N-(4-(Trifluoromethoxy)phenyl)-3-(1H-imidazol-4-yl)propyl-carbamate,
3-(1H-Imidazol-4-yl)propyl (4-biphenyl)methyl-ether,
3-(1H-Imidazol-4-yl)propyl 2-quinolylmethyl-ether,
3-(1H-Imidazol-4-yl)propyl 4-pentinyl-ether,
3-(1H-Imidazol-4-yl)propyl 1-(methylthio)phenylmethyl-ether,
3-(1H-Imidazol-4-yl)propyl diphenylmethyl-ether,
((4-Fluorophenyl)phenylmethyl) 3-(1H-imidazol-4-yl)propyl-ether,
Bis(4-fluorophenyl)methyl 3-(1H-imidazol-4-yl)propyl-ether,
4-(4-(3-1H-Imidazol-4-yl)propyloxy)phenyl-2-butanone,
(4-(3-(1H-Imidazol-4-yl)propyloxy)phenyl)carbaldehyde,
(4-(3-(1H-Imidazol-4-yl)propyloxy)phenyl)propanone,
(4-(1-1H-Imidazol-4-yl)propyloxy)phenyl)-2-methylpropanone,
Cyclopropyl 4-(3-(1H-imidazol-4-yl)propyloxy)phenyl-ketone,
Cyclobutyl 4-(3-(1H-imidazol-4-yl)propyloxy)phenyl-ketone,
Cyclopentyl 4-(3-(1H-imidazol-4-yl)propyloxy)phenyl-ketone,
Cyclohexyl 4-(3-(1H-imidazol-4-yl)propyloxy)phenyl-ketone,
4-(3-(1H-Imidazol-4-yl)proyloxy)phenyl-phenyl-ketone,
4-(3-1H-Imidazol-4-yl)propyloxy)phenyl-4-fluorophenyl-ketone,
(4-(3-(1H-Imidazol-4-yl)propyloxy)phenyl)methanol,
1-(4-(3-(1-Imidazol-4-yl)propyloxy)phenyl)ethanol,
1-(4(3-(1H-Imidazol-4-yl)propyloxy)phenyl-2-methylpropanol,
Cyclopropyl-(4-(3-(1H-imidazol-4-yl)propyloxy)phenyl)methanol,
(4-(3-(1H-Imidazol-4-yl)propyloxy)phenyl)butanone,
(4-(3-(1H-Imidazol-4-yl)propyloxy)phenyl)ethanone-oxime,
(4-(3-(1H-Imidazol-4-yl)propyloxy)phenyl)ethanone-O-methyloxime, (4-(3-(1H-Imidazol-4-yl)propyloxy)phenyl)-2-propanone,
4-(3-(1H-Imidazol-4-yl)propyloxy)-2-butanone,
N-(3,3-Diphenylpropyl) 3-(1H-imidazol-4-yl)propyl-carbamate,
4-[3(3-(Hydroxyiminomethylene)phenoxy)propyl]-1H-Imidazole,
4-[3-(3-Formylphenoxy)propyl-1H-Imidzole,
4-[3-(4-(Benzyloxy)phenoxy)propyl]-1H-Imidazole,
3-(1H-Imidazol-4-yl)propyl N-(2-propenyl)carbamate,
3-(1H-Imidazol-4-yl)propyl N-(3-phenyl-3-pentyl) carbamate,
N-(1,1-Diphenylethyl)-3-(1H-imdazol-4-yl)propyl-carbamate,
3-(1H-Imidazol-4-yl)propyl 2-propenyl-ether,
3-(1H-Imidazol-4-yl)propyl 4-pentenyl-ether,
3-(1H-Imidazol-4-yl)propyl 2-propynyl-ether,
4-(1-Ethynyl)phenyl 3-(1H-imidazol-4-yl)propyl-ether,
3-(1H-Imidazol-4-yl)propyl 4-(1-pentynyl)phenyl-ether,
4-(3,3-Dimethyl-1-butynyl)phenyl-3-(1H-imdazol-4-yl) propylether,
1-(4-Fluorophenyl)-4-(3-(1H-imidazol-4-yl)propyloxy) butanone,
Cyclopropyl 4-(2-(1H-imidazol-4-yl) ethyloxy)phenyl-ketone,
1-(4-(3-(1-Imidazol-4-yl)propyloxy)phenyl)pentanone,
1-(4-(3-(1H-Imidazol-4-yl)propyloxy)phenyl)hexanone,
3,3-Dimethyl-1-(4-(3-(1H-imidazol-4-yl)propyloxy) phenyl)butanone,
4-Hydroxy-1-(4-(3-(1H-imidazol-4-yl)propyloxy)phenyl) butanone,
4-Hydroxy-(4-(3-(1H-imidazol-4-yl)propyloxy)phenyl) butanone ethylene acetal,
5-(3-(1H-Imidazol-4-yl)propyloxy)-1-indanone,
3,4-Dihydro-6-(3-(1H-imidazol-4-yl)propyloxy)-2H-naphthalen-1-one,
1-(2-Fluoro-4-(3-(1H-imidazol-4-yl)proyloxy)phenyl) propanone,
4-(3-(1H-Imidazol-4-yl)propyloxy)phenyl 2-thienyl-ketone,
(4-(3-(1H-Imidazol-4-yl)propyloxy)phenyl)-carbaldehyde oxime,
1-(4-(3-1H-Imidazol-4-yl)propyloxy)phenyl)propanone oxime,
1-(4-(3-(1H-Imdazol-4-yl)propyloxy)phenyl)butanone oxime,
1-(4-(3-(1H-Iimidazol-4-yl)propyloxy)phenyl)pentanone oxime,
Cyclopropyl 4-(3-1H-imidazol-4-yl)proyloxy)phenyl-ketone oxime,
1-(4-(3-(1H-Imidazol-4-yl)propyloxy)-2-methylphenyl)-ethanone oxime,
1-(2-Fluoro-4-(3-(1H-imidazol-4-yl)propyloxy)phenyl) ethanone oxime,
(4-(3-(1H-Imidazol-4-yl)propyloxy)phenyl)carbaldehyde O-methyloxime,
1-(4-(3-1H-Imidazol-4-yl)propyloxy)phenyl)ethanone semicarbazone,
6-(3-(1H-Imidazol-4-yl)propyloxy)-2H-1,3-benzoxathiol-2-one,
3-(1H-Imidazol-4-y)propyl 4-(5-methyl-1,2,4-oxadiazol-3-yl)phenyl ether,
4-Fluorophenyl-4-(3-(H-imidazol-4-yl)propyloxy)phenyl-sulphone,
1-(4-(3-(1H-Imidazol-4-yl)propyloxy)phenyl)-3-phenyl-2-propen-1-one,
1-(4-(3-(1H-Imidazol-4-yl)propyloxy)phenyl)heptanone,
1-(4-(3-(1H-Imidazol-4-yl)propyloxy)phenyl)-2-phenylethanone, 4-[3-(3-(Trifluoromethyl)phenylamino)propyl]-1H-imidazole,
4-[3-(3-Ethanoylphenylamino)propyl]-1H-imidazole,
4-[3-(3-Ethylphenylamoni)propyl]-1H-imidazole,
4-[2-(3-Ethanoylphenylthio)ethyl]-1H-imidazole,
4-[3-(3-(1-Hydroximinoethyl)phenoxy)propyl]-1H-imidazole,
4-[2-(3-(Trifluoromethyl)phenylthio)propyl]-1H-imidazole,
4-[2-(4-Methylphenoxy)ethyl]1H-imidazole,
4-[2-(4-Propionylphenoxy)ethyl]-1H-imidazole,
4-[3-4-(sec Butylphenoxy)propyl]-1H-imidazole,
4-[3-(4-Ethylphenoxy)propyl]-1H-imidazole,
4-[3-(4-(Imidazol-1-yl)-phenoxy)propyl]-1H-imidazole,
4-[3-(4-N,N-Dimethylsulphamoyl)phenoxy)propyl]-1H-imidazole,
4-[3-(4-(methylthiophenoxy)propyl)]-1H-imidazole,
4-[3-(4-(benzylthiophenoxy)propyl]-1H-imidazole,
4-[3-(3-Acetylphenylthio)propyl]-1H-imidazole,
4-[3-(4-Ethylphenylamino)propyl]-1H-imidazole,
4-[3-(4-chlorophenylanino)propyl]-1H-imidazole,
3-(1H-Imidazol-4-yl)propyl 4-(2-trimethylsilyl)-1-ethynyl) phenyl-ether,
3-(1H-Imidazol-4-yl)propyl 4-(1-propynyl)phenyl-ether,
3-(1H-Imidazol-4-yl)propyl 4-isopropylphenyl-ether,
3-(1H-Imidazol-4-yl)propyl methyl-ether,
Ethyl 3-(1H-imidazol-4-yl)propyl-ether,
3-(1H-Imidazol-4-yl)propyl propyl-ether,
Cyclopropyl 3-(1H-imidazol-4-yl)propyl-ether,
Cyclopropylmethyl 3-(1H-imidazol-4-yl)propyl-ether,
N-[3,5-Di(trifluoromethyl)phenyl] 3-(1H-imidazol-4-yl) propyl-carbamate,
N-[1-t-Butyl-2-phenyl)ethyl 3-(1H-imidazol-4-yl)propyl carbamate and N-(1-Ethylpropyl) 3-(1H-Imidazol-4-yl) propyl-carbamate.

25. A compound having a formula selected from the group consisting of

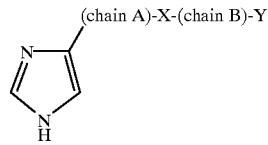

(Ia)

and

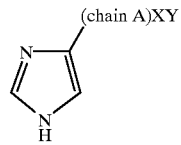

(Ib)

wherein A is selected from the group consisting of alkyl of 1 to 8 carbon atoms, alkene of 2 to 8 carbon atoms and alkyne of 2 to 4 carbon atoms;

X is selected from the group consisting of —OCON (alkene)-, —OCSNH—, —CH$_2$—, —OCH$_2$CO—, —CS and alkene;

B is alkyl of 1 to 8 carbon atoms or —(CH$_2$)$_n$ (heteroatom)- where the heteroatom is sulfur or oxygen, n is an integer between 1 and 5;

Y is selected from the group consisting of a)henyl substituted with at least one member selected from the group consisting of halogen, —OCF$_3$, —CHO, —CF$_3$, —SO$_2$N(alkyl)$_2$, —SO$_2$N(CH$_3$)$_2$, halogen, —NO$_2$, —S(alkyl), —S(aryl), —SCH$_2$(phenyl), alkene, alkyne optionally substituted with trialkylsilyl, —O(alkyl), O—(aryl), —CH₂CN, a ketone, an aldehyde, a sulphone, an acetal, —OH, —CH═CH—CHO, —C(alkyl)═N—OH, —Calkyl—NO(alkyl), —CH₂—NOH, —CH₂—NO(alkyl)-, —C(alkyl)═NH—NH—CONH₂, —O-phenyl, —OCH₂(phenyl), —C(cycloalkyl)═N—O(alkyl), and an optionally substituted heterocycle; b) a heterocycle comprising a sulfur heteroatom; c) cycloalkyl; d) bicyclic cycloalkyl; e) phenyl ring fused to a heterocycle comprising a nitrogen heteroatom or to a carbocycle or a heterocycle bearing a keto function; f) alkyl of 1 to 8 carbon atoms; g) alkynyl of 2 to 8 carbon atoms; h) alkyl mono- or polysubstituted with phenyl either unsubstituted or substituted i) phenyl alkyl ketone or phenyl cycloalkyl ketone; j) substituted or unsubstituted benzophenone; k) substituted or unsubstituted alkyl phenyl alcohol or cycloalkyl phenyl alcohol; l) alkene; m) phenyl cycloalkyl; n) polycyclic consisting of fluorenyl, naphthyl, polyhydronaphthyl and indanyl, o) phenol; p) ketone; q) diphenyl or phenoxyphenyl or benzyloxyphenyl; with the proviso that when X and A each are —CH₂—, Y is other than phenyl;

when A—X of A—X—B is 1-propenyl, Y is other than phenyl unsubstituted or mono-, di or tri-substituted with methyl, ethyl, methoxy, or hydroxy or fluorine or chlorine;

when A—X or A—X—B is 1-butenyl, Y is other than phenyl mono- or disubstituted with methyl, ethyl, methoxy or hydroxy or chlorine;

when A—X or A—X—B is 1-pentenyl, Y is other than phenyl mono- or di-substituted with methyl or methoxy or chlorine;

when A—X or A—X—B is 1-hexenyl, Y is other than 2-chlorophenyl or 2,6-dimethylphenyl.

26. A compound of claim 25 wherein X is selected from the group consisting of —OCON(alkene)-, —OCSNH—, —CH₂—, —OCH₂CH₂CO— and —CS—; Y is phenyl, unsubstituted or substituted with at least one member of the group consisting of —F—, —Cl, —OCF₃, —CHO, —CF₃, —SO₂N(alkyl)₂, —NO₂, —S(alkyl), alkene, —O(alkyl), —CH₂—CN, a ketone, an aldehyde, an alcohol, a lower alkyl, —CH═NOH, —O(phenyl), —OCH₂(phenyl), —C(cycloalkyl)═N—OH, —C(cycloalkyl)═N-(alkyl), —C(alkyl)═NOH, —C(alkyl)═NOCH₃, —CH═CHCHO, a heterocycle containing a sulphur heteroatom, cycloalkyl, phenyl ring fused to a heterocycle comprising a nitrogen heteroatom, alkyl of 1 to 8 carbon atoms, alkyne of 1 to 8 carbon atoms, alkyl mono- or polysubstituted with phenyl unsubstituted or substituted, phenyl alkyl ketone, phenyl cyclo- alkyl ketone, substituted or unsubstituted alkyl phenyl alcohol, cycloalkyl phenyl alcohol, alkene, phenyl cycloalkyl, phenol, a ketone, diphenyl, phenoxyphenyl, benzyloxyphenyl and a polycyclic group selected from the group consisting of fluorenyl, naphthyl, polyhydronaphthyl and indanyl.

27. A compound of claim 25 wherein A is —(CH₂)ₙ—, n is an integer of 1 to 4.

28. A compound of claim 25 wherein A is —(CH₂)₃—.

29. A compound of claim 25 wherein A is —CH═CH—CH₂—.

30. A compound of claim 25 wherein B is alkyl of 1 to 5 carbon atoms, or —(CH₂)ₙ(heteroatom) where n is an integer from 1 to 4.

31. A compound of claim 25 wherein Y is alkyne of 1 to 5 carbon atoms.

32. A compound of claim 25 wherein the bicyclic group Y is norbonyl.

33. A compound of claim 25 wherein X is alkene.

34. A compound of claim 25 wherein Y is selected from the group consisting of a) phenyl substituted with at least one member selected from the group consisting of —OCF₃, —CHO, —SO₂N(alkyl)₂, —SO₂N(CH₃)₂, —S(alkyl), —S(aryl), —SCH₂(phenyl), alkene, alkyne optionally substituted with trialkylsilyl, —O(aryl), —CH₂CN, an aldehyde, a sulphone, an acetal, —OH, —CH═CH—CHO, —O-alkyl, —C(alkyl)═N—O(alkyl), —CH═NOH, —CH═NO(alkyl), —C(alkyl)═NH—NH—CONH₂, —O-phenyl, —OCH₂(phenyl), —C(cycloalkyl)═NOH, —C(cycloalkyl)═N—O(alkyl) and an optionally substituted heterocycle; b) phenyl ring fused to a non-aromatic carbocycle or a heterocycle bearing a keto function; c) alkyne of 1 to 8 carbon atoms; d) substituted or unsubstituted phenyl alkyl alcohol and cycloalkyl phenyl alcohol; e) alkene; f) phenyl cyclo-alkyl; g) polycyclic selected from the group consisting of fluorenyl, polyhydronaphthyl and indenyl, h) phenol i) diphenyl; j) phenoxyphenyl and k) benzyloxyphenyl.

35. A compound of claim 25 wherein X is —CH₂— and Y is other than optionally substituted phenyl.

36. A compound of claim 25 wherein Y is a) phenyl optionally substituted with at least one member selected from the group consisting of halogen, —CF₃, —NO₂, —O(alkyl), ketone, lower alkyl and heterocyclic comprising a sulphur heteroatom; b) cycloalkyl; c) bicyclic; d) phenyl ring fused to a heterocycle comprising a nitrogen heteroatom or to a carbocycle; e) alkyl of 1 to 8 carbon atoms; f) alkyl substituted with phenyl optionally substituted g) phenylalkyl ketone and phenyl cycloalkyl ketone h) substituted or unsubstituted benzophenone; i) naphthyl; and j) a ketone.

37. A compound of claim 25 wherein Y is selected from the group consisting of a) phenyl substituted with at least one keto; b) phenyl ring fused to a heterocycle bearing a keto function; c) phenyl alkyl ketone and phenyl cycloalkyl ketone; d) substituted or unsubstituted benzophenone and e) a ketone.

38. A compound of claim 25 wherein Y is a ketone selected from the group consisting of a ketone substituted with an unsubstituted or substituted alkyl and a ketone substituted with an unsubstituted or substituted aryl.

39. A compound of claim 25 wherein Y is selected from the group consisting of aliphatic ketone of 1 to 8 carbon atoms, cycloalkyl ketone, aryl alkyl ketone and aryl alkenyl ketone in which the aryl group is unsubstituted or substituted and heteroaryl ketone.

40. A compound of claim 39 wherein the chain of the aliphatic ketone bears a hydroxyl.

41. A compound of claim 39 wherein the heteroaryl ketone has a monocyclic heteroaryl unit.

42. A compound of claim 39 wherein Y is cycloalkyl ketone.

43. A compound of claim 25 wherein Y is mono- or polysubstituted phenyl.

44. A compound of claim 43 wherein the heterocycle substituent is oxadiazole or imidazole.

45. A compound of claim 43 wherein the phenyl substitutent is selected from the group consisting of —CHO, —CH═CH—CHO, an aldehyde, —C(alkyl)═N—OH, —C(alkyl)-N—O(alkyl), —CH═NOH, —CH═NO(alkyl), —C(alkyl)═NH—NH—CONH₂, —C(cycloalkyl)═N—OH and —C(cycloalkyl)═N-(alkyl).

46. A compound of claim 43 wherein the phenyl substitutent is selected from the group consistent of —OCF₃—O (alkyl), —O(aryl), —OCH$_2$(phenyl), —O(alkyl), —O(aryl), —O(phenyl) and —OCH$_2$(phenyl).

47. A compound of claim 43 wherein the phenyl substitutent is —OH.

48. A compound of claim 43 wherein the phenyl substituent is selected from the group consisting of alkyl, alkene, and alkyne optionally substituted with trialkylsilyl.

49. A compound of claim 25 wherein Y is selected from the group consisting of alkene and alkyne.

50. A compound of claim 25 wherein Y is a substituted or unsubstituted alkyl phenyl alcohol or cycloalkyl phenyl alcohol.

51. A compound of claim 25 wherein Y is phenylcycloalkyl.

52. A compound of claim 25 wherein:

A is —(CH$_2$)$_n$— where n is an integer of 1 to 8 or alkene of 1 to 4 carbon atoms;

X is selected from the group consisting of —OCON(alkene)-, —OCSNH—, —CH$_2$—, —OCH$_2$CO— and alkene;

B is selected from the group consisting of alkyl of 1 to 8 carbon atoms and

—(CH$_2$)$_n$(heteroatom)-, where the heteroatom is oxygen or sulphur and n is an integer between 0 and 4;

Y is selected from the group consisting of a) phenyl unsubstituted or substituted with at least one substituent selected from the group consisting of alkyl, —CF$_3$, —SO$_2$N(alkyl)$_2$, —S(alkyl), —S(aryl), —SCH$_2$(phenyl), —SO$_2$N(CH$_3$)$_2$, —SCH$_3$, alkene, alkyne optionally substituted with trialkylsilyl, —OCH$_3$, —NO$_2$, —OCF$_3$, a ketone, —OH, halogen, a sulphone, an acetal, —CH$_2$CN, an aldehyde, —C-(alkyl)O=NOH, —CH=N—O(alkyl), —(alkyl)C=NO(alkyl), —C(alkyl)=N—NHCONH$_2$, —CH=CH—CHO, —O(alkyl), —O(aryl), —CH=NOH, —OCH$_2$(phenyl), and optionally substituted heterocycle; b) a heterocycle comprising a sulphur heteroatom; c) cycloalkyl; d) norbornyl; e) phenyl ring fused to a heterocycle comprising a nitrogen heteroatom or to a carbocycle or a heterocycle bearing a keto function; f) alkyl of 1 to 8 carbon atoms; g) an alkyl polysubstituted with phenyl unsubstituted or substituted; h) phenyl alkyl ketone and phenylcycloalkyl ketone; i) benzophenone; j) alkyl phenyl alcohol and cycloalkyl phenyl alcohol; k) alkyne and alkene; l) piperidyl; m) phenylcycloalkyl; n) fluorenyl, naphthyl, polyhydronaphthyl or indanyl; o) phenol; p) a ketone or keto derivative; q) diphenyl; r) phenoxyphenyl and s) benzyloxyphenyl.

53. A compound of claim 42 wherein;

A is —(CH$_2$)$_n$— where n is an integer of 1 to 8 or an unbranched alkene of 2 to 4 carbon atoms;

X is selected from the group consisting of —OCON(alkene)-, —OCSNH—, —CH$_2$— and OCH$_2$CO—;

B is selected from the group consisting of alkyl of 1 to 5 carbon atoms and —(CH$_2$)$_n$(heteroatom)-, where the heteroatom is selected from sulphur or oxygen and n is an integer which vary between 1 and 4;

Y is selected from the group consisting of a) phenyl unsubstituted or substituted with at least one member of the group consisting of halogen, alkyl, —CF$_3$, —SO$_2$N(alkyl)$_2$, —S(alkyl), alkene, alkyne, —OCH$_3$, —NO$_2$, —OCF$_3$, —CH$_2$CN, a ketone, an aldehyde, —OH, —O(alkyl), —CH=CH—CHO, —CH=NCH$_3$, —C(alkyl)=NOH, —C(alkyl)=NOCH$_3$, —OCH$_2$(phenyl) and a heterocycle comprising a sulphur heteroatom; b) a cycloalkyl; c) norbornyl; d) phenyl ring fused to a heterocycle comprising a nitrogen heteroatom; e) alkyl of 1 to 8 carbon atoms and alkyl polysubstituted with phenyl unsubstituted or substituted; f) phenyl alkyl ketone and phenyl cycloalkyl ketone; g) benzophenone; h) alkyl phenyl alcohol or cycloalkyl phenyl alcohol; h) alkene or alkyne; i) phenylcycloalkyl; j) polycyclic selected from the group consisting of fluorenyl, naphthyl, polyhydronaphthyl and indanyl; k) diphenyl; l) phenoxyphenyl; m) phenol; and n) benzyloxyphenyl.

54. A compound of claim 52 of formula 1b in which A and X are as defined and Y is phenyl at least monosubstituted with a ketone.

55. A compound of claim 54 wherein the keto substitutent is selected from the group consisting of aliphatic ketone of 1 to 8 carbon atoms, cycloalkyl ketone, aryl alkyl ketone and aryl alkenyl ketone in which the aryl group is unsubstituted or substituted and heteroaryl ketone.

56. A compound of claim 55 wherein the linear aliphatic ketone bears a hydroxy.

57. A compound of claim 55 wherein the heteroaryl ketone has a monocyclic heteroaryl.

58. A compound of claim 55 wherein Y is substituted with a cycloalkyl ketone.

59. A compound of claim 52 of formula (1b) in which A and X are as defined and Y is phenyl at least monosubstituted with a keto defined in the oxime group.

60. A compound of claim 52 wherein Y is disubstituted phenyl with one of the substituents being selected from halogen and lower alkyl.

61. A compound of claim 52 of the formula (1b) in which A and X are as defined and Y is phenyl at least monosubstituted with an acetal.

62. A compound of claim 52 of formula (1b) in which A and X are as defined and Y is phenyl at least monosubstituted with a sulphone.

63. A compound of claim 52 of formula 1b in which A and X are as defined and Y is phenyl at least monosubstituted with an optionally substituted oxadiazole.

64. A compound of claim 52 of formula (1b) in which A and X are as defined and Y is phenyl at least monosubstituted with an unsaturated aliphatic.

65. A compound of claim 52 wherein Y is phenyl substituted with alkyne optionally substituted with trialkylsilyl.

66. A compound of claim 52 of formula (1b) in which A and X are as defined and Y is phenyl fused to a carbocycle bearing a keto function.

67. A compound of claim 52 of formula (1b) in which A and X are as defined and Y is phenyl fused to a heterocycle bearing a keto function.

68. A compound of claim 52 wherein A is —(CH$_2$)$_3$—.

69. A compound of claim 24 selected from the group consisting of:
N,N-Diallyl 3-(1H-imidazol-4-yl)propyl-carbamate,
3-(1H-Imidazol-4-yl)propyl-N-phenyl-thioncarbamate,
3-(1H-Imidazol-4-yl)-4-phenyl-1-butene,
3-(1H-Imidazol-4-yl)-4-phenylbutane,
2-(3-(1H-Imidazol-4-yl)propyloxy)-1-phenylethanone,
2-(3-(-1H-Imidazol-4-yl)propyloxy)-1-(3-nitrophenyl) ethanone, (1H-Imidazol-4-yl)nonane,
1-(1H-Imidazol-4-yl)-6-phenyl-hexane and
1-(1H-Imidazol-4-yl)-6-phenyl-3-hexene.

70. A compound of claim 25 selected from the group consisting of:
N,N-Diallyl-3-(1H-imidazol-4-yl)propyl-carbamate,
3-(1H-Imidazol-4-yl)propyl N-phenyl-thioncarbamate,
3-(1H-Imidazol-4-yl)-4-phenyl-1-butene, 3-(1H-Imidazol-4-yl)-4-phenylbutane,
2-(3-(1H-Imidazol-4-yl)propyloxy)-1-phenylethanone,
2-(3-(1H-Imidazol-4-yl)propyloxy)-1-(3-nitrophenyl) ethanone and
(1H-Imidazol-4-yl)nonane.

71. A compound of claim 25 selected from the group consisting of:
N-t-Butyl 3-(1H-imidazol-4-yl)propyl-carbamate,
3-(1H-Imidazol-4-yl)propyl 3-methylbutyl-ether,
3-(1H-Imidazol-4-yl)propyl 3,3,-dimethylbutyl ether,
3-(1H-Imidazol-4-yl)propyl 4-methylpentyl-ether,
4-[3-(3-(Trifluoromethyl)phenoxy)propyl]-1H-imidazole,
4-[3-(3-Nitrophenoxy)propyl]-1H-imidazole,
4-[2-(3-(Trifluoromethyl)phenoxy)thioethyl]-1H-imidazole,
4-[3-(3-Isopropylphenoxy)propyl]-1H-imidazole,
4-[3-(3-tert-Butylphenoxy)propyl]-1H-imidazole,
4-[3-(3-Ethanoylphenoxy)propyl]-1H-imidazole,
4-[3-(3-Ethylphenoxy)propyl]-1H-imidazole,
4-[4-(3-Trifluoromethylphenoxy)butyl]-1H-imidazole,
4-[4-(3-Ethanoylphenoxy)butyl]-1H-imidazole,
4-[3-(3-Propylphenoxy)propyl]-1H-imidazole,
3-(1H-Imidazol-4-yl)propyl N-(2-methyl-2-butyl)-carbamate and
N-(2,2-Dimethylpropyl) 3-(1H-imidazol-4-yl)propyl-carbamate.

72. A compound of claim 25 selected from the group consisting of:
3-(1H-Imidazol-4-yl)propyl N-propyl-carbamate,
N-Butyl 3-(1H-imidazol-4-yl)propyl-carbamate,
3-(1H-Imidazol-4-yl)propyl N-pentyl-carbamate,
N-Hexyl 3-(1H-imidazol-4-yl)propyl-carbamate,
N-Heptyl 3-(1H-imidazol-4-yl)propyl-carbamate,
3-(1H-Imidazol-4-yl)propyl N-octyl-carbamate,
3-(1H-Imidazol-4-yl)propyl N-(2-heptyl)carbamate,
3-(1H-Imidazol-4-yl)propyl N-(2-octyl)carbamate,
3-(1H-Imidazol-4-yl)propyl N-(3-methylbutyl)carbamate,
3-(1H-Imidazol-4-yl)propyl N-(2-methylbutyl)carbamate,
3-(1H-Imidazol-4-yl)propyl N-(2-pivalyl)-carbamate,
3-(1H-Imidazol-4-yl)propyl N,N-dipropyl-carbamate,
N-(3-(1H-Imidazol-4-yl)propyloxycarbonyl)piperidine,
N-(4-Fluorophenylmethyl) 2-(1H-imidazol-4-yl)ethyl-carbamate,
N-(3-Trifluoromethyl)phenylmethyl) 3-(1H-imidazol-4-yl)propyl-carbamate,
3-(1H-Imidazol-4-yl)propyl-N (2-thenyl)carbamate,
3-(1H-Imidazol-4-yl)-1-(4-methylphenyl)propanone,
Cyclohexylmethyl (1H-imidazol-4-yl)methyl-ether,
(Bicyclo[2.2.1]hept-2-yl)methyl 1H-imidazol-4-yl)methyl-ether,
3-(1H-Imidazol-4-yl)propyl 3-(4-methylphenyl)propyl-ether,
3-(1H-Imidazol-4-yl)propyl 2-naphthylmethyl-ether,
(3-(4-Trifluoromethyl)phenyl)propyl 3-(1H-imidazol-4-yl)propyl-ether,
3-(2,4-Dichlorophenyl)propyl 3-(1H-imidazol-4-yl)propyl-ether,
2-(Bicyclo[2.2.1]hept-2-yl)ethyl 3-(1H-imidazol-4-yl)propyl-ether,
3-(1H-Imidazol-4-yl)propyl 3-(4-methylphenyl)propyl-ether,
3-(1H-Imidazol-4-yl)propyl 2-naphthylmethyl-ether,
(3-(4-Trifluoromethyl)phenyl)propyl 3-(1H-imidazol-4-yl)propyl-ether,
3-(2,4-Dichlorophenyl)propyl-3-(1H-imidazol-4-yl)propyl-ether,
2-(Bicyclo[2.2.1]hept-2-yl)ethyl3-(1H-imidazol-4-yl)propyl-ether,
3-(1H-Imidazol-4-yl)propyl 3-(4-methoxyphenyl)propyl-ether,
3-(1H-Imidazol-4-yl)propyl 2-phenylethyl-ether,
3-(1H-Imidazol-4-yl)propyl heptyl-ether,
3-(1H-Imidazol-4-yl)propyl 2-methylpropyl-ether,
2-Cyclohexylethyl 3-(1H-Imidazol-4-yl)propyl-ether,
3-(1H-Imidazol-4-yl)propyl 2-(phenoxy)ethyl-ether,
3-(4-Fluorophenyl)propyl 3-(1H-imidazol-4-yl)-2-propenyl-ether,
1-(4-(3-(1H-Imidazol-4-yl)propyloxy)phenyl)ethanone,
3-1H(Imidazol-4-yl)-propyl-4-methoxyphenyl-ether,
N-(4-Acetylphenyl) (3-(1H-imidazol-4-yl)propyl-carbamate,
N-(3-Acetylphenyl) (3-(1H-imidazol-4-yl)propyl-carbamate,
3-(1H-Imidazol-4-yl)propyl 2-methoxyethyl-ether,
3-Cyclopentylpropyl 3-(1H-imidazol-4-yl)propyl-ether,
3-(1H-imidazol-4-yl)propyl N-isopropyl-carbamate,
3-(1H-Imidazol-4-yl)propyl N-(3-phenyl-3-pentyl) carbamate,
N-(3,5 Dimethylphenyl) 3-(1H-imidazol-4-yl)propyl-carbamate,
1,1-Dimethylethyl-2 (1H-imidazol-4-yl)ethyl-ether,
1,1-Dimethylethyl-3 (1H-imidazol-4-yl)propyl-ether,
4-Butylphenyl 3-(1H-imidazol-4-yl)propyl-ether,
1-(4-(3-(1H-Imidazol-4-yl)propyloxy)-2-methylphenyl) ethanone and
(2-Fluoro-4-(3-(1H-imidazol-4-yl)propyloxy)phenyl) ethanone.

73. A compound of claim 3 selected from the group consisting of
3-(1H-Imidazol-4-yl)propyl N-(diphenylmethyl)carbamate,
3-(1H-Imidazol-4-yl)propyl N-(2,2-diphenylethyl) carbamate,
2-(1H-Imidazol-4-yl) ethyl N-(2,2-diphenylethyl) carbamate,
4-[3-(3-(Trifluoromethoxy)phenoxy)propyl]-1H-Imidazole,
4-[3-(3-Propanoylphenoxy)propyl]-1H-imidazole,
4-[3-(3-(1-Hydroxypropyl)phenoxy)propyl]-1H-imidazole,
4-[3-(1,2,3,4,-Tetrahydro-6-naphthyloxy)propyl]-1H-imidazole,
4-[3-(5-Indanyloxy)propyl]-1H-imidazole,
4-[3-(3-(N,N-Dimethylsulphonamido)phenoxy)propyl]-1H-imidazole,
4-[3-(3-Hydroxyphenoxy)propyl]-1H-imidazole,
4-(3-[3-(2-Penten-3-yl)phenoxy]propyl)-1H-imidazole,
4-[3-(4-(Cyanomethyl)phenoxy)propyl]-1H-imidazole,
4-[3-(4-Phenoxyphenoxy)propyl]-1H-imidazole,
3-(1H-Imidazol-4-yl)propyl N-trans-(2-phenylcyclopropyl) carbamate,
3-(1H-Imidazol-4-yl)propyl N-(2-phenylpropyl)carbamate,
N-Fluoren-9-yl 3-(1H-imidazol-4-yl)propyl-carbamate,
N-(4-Trifluoromethoxy)phenyl) 3-(1H-imidazol-4-yl) propyl-carbamate,
3-(1H-Imidazol-4-yl)propyl (4-biphenyl)methyl-ether,
3-(1H-Imidazol-4-yl)propyl 2-quinoiylmethyl-ether,
3-(1H-Imidazol-4-yl)propyl 4-pentinyl-ether,
3-(1H-Imidazol-4-yl)propyl 4-(methoylthio)phenylmethyl-ether,
3-(1H-Imidazol-4-yl)propyl diphenylmethyl-ether,
((4-Fluorophenyl)phenylmethyl) 3-(1H-imidazol-4-yl) propyl-ether,
Bis(4-fluorophenyl)methyl 3-(1H-imidazol-4-yl)propyl-ether,
4-(4-(3-(1H-Imidazol-4-yl)propyloxy)phenyl)-2-butanone,
(4-(3-(1H-Imidazol-4-yl)propyloxy)phenyl)carbaldehyde,
1-(4-(3-(1H-Imidazol-4-yl)propyloxy)phenyl)propanone, 1-(4-(3-(1H-Imidazol-4-yl)propyloxy)phenyl)-2-methylpropanone,
Cyclopropyl 4-(3-(1H-imidazol-4-yl)propyloxy)phenyl-ketone,
Cyclobutyl 4-(3-(1H-imidazol-4-yl)propyloxy)phenyl-ketone,
Cyclopentyl 4-(3-(1H-imidazol-4-yl)propyloxy)phenyl-ketone,
Cyclohexyl 4-(3-(1H-imidazol-4-yl)propyloxy)phenyl-ketone,
4-(3-(1H-Imidazol-4-yl)propyloxy)phenyl phenyl-ketone
4-(3-(1H-Imidazol-4-yl)propyloxy)phenyl 4-fluorophenyl-ketone,
(4-(3-(1H-Imidazol-4-yl)propyloxy)phenyl)methanol,
1-(4-(3-(1H-Imidazol-4-yl)propyloxy)phenyl)ethanol,
1-(4-(3-(1H-Imidazol-4-yl)propyloxy)phenyl)-2-methylpropanol,
Cyclopropyl-(4-(3-(1H-imidazol-4-yl)propyloxy)phenyl)methanol,
1-(4-(3-(1H-imidazol-4-yl)propyloxy)phenyl)butanone,
1-(4-(3-(1H-Imidazol-4-yl)propyloxy)phenyl)ethanone oxime,
1-(4-(3-(1H-Imidazol-4-yl)propyloxy)phenyl)ethanone O-methyoxime,
1-(4-(3-(1H-Imidazol-4-yl)propyloxy)phenyl-2-propanone,
4-(3-(1H-Imidazol-4-yl)propyloxy)-2-butanone,
N-(3,3-Diphenylpropyl) 3-(1H-imidazol-4-yl)propyl-carbamate,
4-[3-(3-(Hydroxyiminomethylene)phenoxy)propyl]-1H-imidazole,
4-[3-(3-Formylphenoxy)propyl]-1H-imidazole and
4-[3-(4-(Benzyloxy)phenoxy)propyl]-1H-imidazole.

74. A compound of claim 71 selected from the group consisting of
3-(1H-Imidazol-4-yl)propyl N-(diphenylmethyl)carbamate,
3-(1H-Imidazol-4-yl)propyl N-(2,2-diphenylethyl)carbamate,
2-(1H-Imidazol-4-yl)ethyl N-(2,2-diphenylethyl)carbamate,
4-[3-(3-(Trifluoromethoxy)phenoxy)propyl]-1H-imidazole,
4-[3-(3-Propanoylphenoxy)propyl]-1H-imidazole,
4-[3-(3-(1-Hydroxypropyl)phenoxy)propyl]-1H-imidazole,
4-[3-(3-(Trifluoromethyl)phenylamino)propyl]-1H-imidazole,
4-[3-(3-Ethanoylphenylamino)propyl]-1H-imidazole,
4-[3-(3-Ethylphenylamino)propyl]-1H-imidazole,
4-[2-(3-Ethanoylphenylthio)ethyl]-1H-imidazole,
4-[3-(3-(1-Hydroximinoethyl)phenoxy)propyl]-1H-imidazole and
4-[2-(3-(Trifluoromethyl)phenylthio)propyl]-1H-imidazole.

75. A compound of claim 71 selected from the group consisting of
4-[3-(1,2,3,4-Tetrahydro-6-naphthyloxy)propyl]-1H-imidazole,
4-[3-(5-Indanyloxy)propyl]-1H-imidazole,
4-[3-(3-(N,N-Dimethylsulphonamido)phenoxy)propyl]-1H-imidazole,
4-[3-(3-Hydroxyphenoxy)propyl]-1H-imidazole,
4-(3-[3-(2-Penten-3-yl)phenoxyl]propyl)-1H-imidazole,
4-[3-(4-(Cyanomethyl)phenoxy)propyl]-1H-imidazole,
4-[3-(4-(Phenoxy)phenoxy)propyl]-1H-imidazole,
3-(1H-Imidazol-4-yl)propyl N-trans-(2-phenylcyclopropyl)carbamate,
3-(1H-Imidazol-4-yl)propyl N-(2-phenylpropyl)carbamate,
N-(4-Trifluoromethoxy)phenyl) 3-(1H-Imidazol-4-yl)propyl-carbamate,
3-(1H-Imidazol-4-yl)propyl (4-biphenyl)methyl-ether,
3-(1H-Imidazol-4-yl)propyl 2-quinolylmethyl-ether,
3-(1H-Imidazol-4-yl)propyl 4-pentinyl-ether,
3-(1H-imidazol-4-yl)propyl 4-(methylthio)phenylmethyl-ether,
3-(1H-Imidazol-4-yl)propyl diphenylmethyl-ether,
(4-Fluorophenyl)phenylmethyl 3-(1H-imidazol-4-yl)propyl-ether,
Bis-(4-fluorophenyl)methyl 3-(1H-imidazol-4-yl)propyl-ether,
4-(4-(3-1H-Imidazol-4-yl)propyloxy)phenyl)-2-butanone,
(4-(3-(1H-Imidazol-4-yl)propyloxy)phenyl)carbaldehyde,
1-(4-(3-(1H-Imidazol-4-yl)propyloxy)phenyl)propanone,
1-(4-(3-(1H-Imidazol-4-yl)propyloxy)phenyl)-2-methylpropanone,
Cyclopropyl 4-(3-(1H-imidazol-4-yl)propyloxy)phenyl-ketone,
Cyclobutyl 4-(3-(1H-Imidazol-4-yl)propyloxy)phenyl-ketone,
Cyclopentyl 4-(3-(1H-imidazol-4-yl)propyloxy)phenyl-ketone,
Cyclohexyl 4-(3-(1H-imidazol-4-yl)propyloxy)phenyl-ketone,
4-(3-(1H-Imidazol-4-yl)propyloxy)phenyl phenyl-ketone,
4-(3-(1H-Imidazol-4-yl)propyloxy)phenyl 4-fluorophenyl-ketone,
(4-(3-(1H-Imidazol-4-yl)propyloxy)phenyl)methanol,
1-(4-(3-(1H-Imidazol-4-yl)propyloxy)phenyl)ethanol,
1-(4-(3-(1H-Imidazol-4-yl)propyloxy)phenyl-2-methylpropanol,
Cyclopropyl-(4-(3-(1H-imidazol-4-yl)propyloxy)phenyl)methanol,
1-(4-(3-1H-Imidazol-4-yl)propyloxy)phenyl)butanone,
1-(4-(3-(1H-Imidazol-4-yl)propyloxy)phenyl)ethanone oxime,
1-(4-(3-(1H-Imidazol-4-yl)propyloxy)phenyl) ethanone-O-methyloxime,
1-(4-(3-(1H-Imidazol-4-yl)propyloxy)phenyl)-2-propanone,
4-(3-1H-Imidazol-4-yl)propyloxy)-2-butanone,
N-(3,3-Diphenylpropyl) 3-(1H-imidazol-4-yl)propyl-carbamate,
N-(3,3-Diphenylpropyl) 3-(1H-imidazol-4-yl)propyl-carbamate,
4-[3-(3-(Hydroxyiminomethylene)phenoxy)propyl]-1H-imidazole,
4-[3-(3-Formylphenoxy)propyl]-1H-imidazole,
4-[3-(4-(Benzyloxy)phenoxy)propyl]-1H-imidazole,
3-(1H-Imidazol-4-yl)propyl N-(2-propenyl)carbamate,
3-(1H-Imidazol-4-yl)propyl N-(3-phenyl-3-pentyl)carbamate,
N-(1,1-Diphenylethyl) 3-(1H-imidazol-4-yl)propyl-carbamate,
3-(1H-Imidazol-4-yl)propyl 2-propenyl-ether,
3-(1H-Imidazol-4-yl)propyl 4-pentenyl ether,
3-(1H-Imidazol-1-yl)propyl 2-propynyl-ether,
4-(1-Ethynyl)phenyl 3-(1H-imidazol-4-yl)propyl-ether,
3-(1H-Imidazol-4-yl)propyl 4-(1-pentynyl)phenyl-ether,
4-(3,3-Dimethyl-1-butynyl)phenyl 3-(1H-imidazol-4-yl)propyl-ether,
1-(4-Fluorophenyl)-4-(3-(1H-imidazol-4-yl)propyloxy)butanone,
Cyclopropyl-4-(2-(1H-imidazol-4-yl)ethyloxy)phenyl-ketone,
1-(4-(3-1H-Imidazol-4-yl)propyloxy)phenyl)pentanone,
1-(4-(3-(1H-Imidazol-4-yl)propyloxy)phenyl)hexanone,
3,3-Dimethyl-1-(4-(3-(1H-imidazol-4-yl)propyloxy)phenyl)butanone,
4-Hydroxy-1-(4-(3-1H-imidazol-4-yl)propyloxy)phenyl)butanone, 4-Hydroxy-1-(4-(3-(1H-imidazol-4-yl)propyloxy)phenyl) butanone ethylene acetal,
5-(3-(1H-Imidazol-4-yl)propyloxy)-1-indanone,
3,4-Dihydro-6-(3-(1H-imidazol-4-yl)propyloxy)-2H-naphthalen-1-one,
1-(2-Fluoro-4-(3-(1H-imidazol-4-yl)propyloxy)phenyl)-propanone,
4-(3-(1H-Imidazol-4-yl)propyloxy)phenyl 2-thienyl-ketone,
(4-(3-(1H-Imidazol-4-yl)propyloxy)phenyl)carbaldehyde oxime,
1-(4-(3-(1H-Imidazol-4-yl)propyloxy)phenyl)propanone oxime,
1-(4-(3-(1H-Imidazol-4-yl)propyloxy)phenyl)butanone oxime,
1-(4-(3-(1H-Imidazol-4-yl)propyloxy)phenyl)pentanone oxime,
1-(4-(3-(1H-Imidazol-4-yl)propyloxy)phenyl)hexanone oxide,
Cyclopropyl-4-(3-1H-imidazol-4-yl)propyloxy)phenyl-ketone oxime,
1-(4-(3-(1H-Imidazol-4-yl)propyloxy)-2-methylphenyl) ethanone oxime,
1-(2-Fluoro-4-(3-(1H-imidazol-4-yl)propyloxy)phenyl) ethanone oxime,
(4-(3-(1H-Imidazol-4-yl)propyloxy)phenyl)carbaldehyde O-methyloxime,
1-(4-(3-(1H-Imidazol-4-yl)propyloxy)phenyl) ethanonesemicarbazone,
6-(3-(1H-Imidazol-4-yl)propyloxy)-2H-1,3-benzoxathiol-2-one,
3-(1H-Imidazol-4-yl)propyl 4-(5-methyl-1,2,4,-oxadiazol-3-yl)phenyl ether,
4-Fluorophenyl-4-(3-(1H-imidazol-4-yl)propyloxy)phenyl-sulphone,
1-(4-(3-(1H-Imidazol-4-yl)propyloxy)phenyl-3-phenyl-2-propen-1-one,
1-(4-(3-(1H-Imidazol-4-yl)propyloxy)phenyl)heptanone,
1-(4-(3-(1H-Imidazol-4-yl)propyloxy)phenyl)-2-phenylethanone,
4-[2-(4-Methylphenoxy)ethyl]-1H-imidazole,
4-[2-(4-propionylphenoxy)ethyl]-1H-imidazole,
4-[3-(4-sec-Butylphenoxy)propyl]-1H-imidazole,
4-[3-(4-Ethylphenoxy)propyl]-1H-imidazole,
4-[3-(4-Imidazol-1)-yl-phenoxy)propyl]-1H-imidazole,
4-[3-(4-(N,N-Dimethylsulphamoyl)phenoxy)propyl]-1H-imidazole,
4-[3-(4-(methylthio)phenoxy)propyl]-1H-imidazole oxalate,
4-[3-(4-(benzylthio)phenoxy)propyl]-1H-imidazole-hydrochloride,
4-[3-(3-Acetylphenylthio)propyl]-1H-imidazole-oxalate,
4-[3-(4-Ethylphenylamino)propyl]-1H-imidazole-oxalate,
4-[3-(4-Chlorophenylamino)propyl]-1H-imidazole-oxalate,
3-(1H-Imidazol-4-yl)propyl-4-(2-(trimethylsilyl)-1-ethynyl)phenyl-ether,
3-(1H-Imidazol-4-yl)propyl 4-(1-propynyl)phenyl-ether,
3-(1H-Imidazol-4-yl)propyl 4-isopropylphenyl ether,
3-(1H-Imidazol-4-yl)propyl methyl-ether,
Ethyl-3-(1H-imidazol-4-yl)propyl-ether,
3-(1H-Imidazol)-4-yl)propyl-propyl-ether,
Cyclopropyl 3-(1H-imidazol-4-yl)propyl-ether,
Cyclopropylmethyl 3-(1H-imidazol-4-yl)propyl-ether,
N-[3,5-Di(trifluoromethyl)phenyl] 3-(1H-imidazol-4-yl) propyl-carbamate,
N-[1-t-Butyl-2-phenyl)ethyl] 3-(1H-imidazol-4-yl)propyl-carbamate and
N-(1-Ethylpropyl) 3-(1H-imidazol-4-yl)propyl-carbamate.

76. A compound of claim 1 wherein X is —OCONH—.
77. A compound of claim 1 wherein X is —OCON (alkyl)-.
78. A compound of claim 1 wherein X is —OCON (alkene)-.
79. A compound of claim 1 wherein X is —OCO—.
80. A compound of claim 1 wherein X is —CH$_2$—.
81. A compound of claim 1 wherein X is —O—.
82. A compound of claim 1 wherein X is —OCH$_2$CO—.
83. A compound of claim 1 wherein X is —S—.
84. A compound of claim 1 wherein X is —CO—.
85. A compound of claim 1 wherein X is —CS—.
86. A compound of claim 1 wherein X is —NH—.
87. A compound of claim 1 wherein A is —(CH$_2$)$_n$— and n is an integer from 1 to 4.
88. A compound of claim 1 wherein A is —CH═CH—CH$_2$—.
89. A compound according of claim 1 wherein the keto substituent is selected from the group consisting of unsubstituted aliphatic ketone of 1 to 8 carbon atoms or substituted with hydroxyl, cycloalkyl ketone, an aryl alkyl ketone, aryl alkenyl ketone and a heteroaryl ketone.
90. A compound of claim 2 wherein A is —(CH$_2$)—; X is —O— or —OCONH—; B is —(CH$_2$)$_n$— where n=0, 1, 2 or 3; and Y is selected from the group consisting of cyclopentyl, —CH(CH$_3$)$_2$, —CH(phenyl)$_2$, —(CH$_3$)$_3$ and phenyl p-substituted with a member selected from the group consisting of —COC$_3$H$_7$, —OCH$_3$, —CO(cyclopropyl), —C(CH$_3$)═N—OH, —C(cyclopropyl)═NOH, —C(CH$_3$)═NOCH$_3$, and —C(cyclopropyl)═N—OCH$_3$, or m-substituted with —COCH$_3$ or —CF$_3$.
91. A compound of according to claim 2 wherein A is —CH$_2$)$_3$—; X is —O— or —OCONH—; B is —(CH$_2$)$_2$— or —(CH$_2$)$_3$—; and Y is selected from the group consisting of cyclopentyl and phenyl p-substituted with a member selected from the group consisting of —CO(cyclopropyl), —COC$_3$H$_7$, —OCH$_3$, —CHOH(cyclopropyl), —(CH$_3$)═N—OH, —C(cyclopropyl)═N—OH, —C(CH$_3$)═N—OCH$_3$ and —C(cyclopropyl)═N—OCH$_3$.
92. A compound of claim 2 having formula Ib in which Y is phenyl at least monosubstituted with a ketone.
93. A compound of claim 43 wherein the substitutent is an aliphatic acetal of 1 to 8 carbon atoms, optionally bearing a hydroxyl.

* * * * *